(12) United States Patent
Houchen et al.

(10) Patent No.: US 11,655,307 B2
(45) Date of Patent: *May 23, 2023

(54) ANTI-DOUBLECORTIN-LIKE KINASE 1 ANTIBODIES AND METHODS OF USE

(71) Applicant: The Board of Regents of the University of Oklahoma, Norman, OK (US)

(72) Inventors: Courtney W. Houchen, Edmond, OK (US); Nathaniel Weygant, Mustang, OK (US); Dongfeng Qu, Edmond, OK (US); Randal May, Oklahoma City, OK (US); Parthasarathy Chandrakesan, Edmond, OK (US); William L. Berry, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 279 days.

This patent is subject to a terminal disclaimer.

(21) Appl. No.: 16/617,074

(22) PCT Filed: May 30, 2018

(86) PCT No.: PCT/US2018/035071
§ 371 (c)(1),
(2) Date: Nov. 26, 2019

(87) PCT Pub. No.: WO2018/222675
PCT Pub. Date: Dec. 6, 2018

(65) Prior Publication Data
US 2021/0189007 A1 Jun. 24, 2021

Related U.S. Application Data

(60) Provisional application No. 62/512,372, filed on May 30, 2017.

(51) Int. Cl.
*A61P 35/00* (2006.01)
*A61K 47/68* (2017.01)
*A61K 39/00* (2006.01)
*C07K 16/40* (2006.01)

(52) U.S. Cl.
CPC .......... *C07K 16/40* (2013.01); *A61K 47/6871* (2017.08); *A61P 35/00* (2018.01); *A61K 2039/505* (2013.01); *C07K 2317/24* (2013.01); *C07K 2317/33* (2013.01); *C07K 2317/52* (2013.01); *C07K 2317/565* (2013.01); *C07K 2317/92* (2013.01)

(58) Field of Classification Search
CPC ................ C07K 16/40; C07K 2317/24; C07K 2317/33; C07K 2317/52; A61K 47/6871; A61K 2039/505; A61P 35/00
See application file for complete search history.

(56) References Cited

U.S. PATENT DOCUMENTS

| 7,902,166 B2 | 3/2011 | Houchen et al. |
| 8,936,941 B2 | 1/2015 | Anant et al. |
| 9,663,585 B2 | 5/2017 | Houchen et al. |
| 2014/0056972 A1* | 2/2014 | Houchen ................ A61K 45/06 424/450 |
| 2014/0336360 A1 | 11/2014 | Hornbeck et al. |
| 2016/0311928 A1 | 10/2016 | Singh et al. |

FOREIGN PATENT DOCUMENTS

| WO | 2007094842 A2 | 8/2007 |
| WO | 2013148373 A1 | 10/2013 |
| WO | 2015031541 A1 | 3/2015 |
| WO | 2016075099 A1 | 5/2016 |
| WO | 2016166360 A1 | 10/2016 |
| WO | 2019112978 A2 | 6/2019 |

OTHER PUBLICATIONS

International Search Report, dated Oct. 12, 2018, in PCT/US2018/35071, filed May 30, 2018.
Written Opinion of the International Searching Authority, dated Oct. 12, 2018, in PCT/US2018/35071, filed May 30, 2018.
Weygant, et al.; "Systemic Delivery of CBT-15G DCLK1-Targeted Monoclonal Antibody Dramatically Decreases Tumorigenesis in a Xenograft Model of Pancreatic Cancer," Cancer Research (2016), 76(14):577.
Sarkar, et al. "A Novel Antibody Against Cancer Stem Cell Biomarker, DCLK1-S, is Potentially Useful for Assessing Colon Cancer Risk after Screening Colonoscopy," Laboratory Investigation (2017), 97(10):1245-1261.
Weygant, et al.; "DCLK1 is a Broadly Dysregulated Target Against Epithelial-Mesenchymal Transition, Focal Adhesion, and Stemness in Clear Cell Renal Carcinoma," Oncotarget, Impact Journals LLC, (2015), 6(4):2193-2205.
Whorton, et al.; "DCLK1 is Detectable in Plasma of Patients with Barrett's Esophagus and Esophageal Adenocarcinoma," Digestive Diseases and Sciences, (2014), 60:509-513.

(Continued)

*Primary Examiner* — Mark Halvorson
*Assistant Examiner* — Dennis J Sullivan
(74) *Attorney, Agent, or Firm* — Dunlap Codding, P.C.

(57) ABSTRACT

Antibodies and antigen-binding fragments thereof that specifically bind to human DCLK1 protein, hybridomas or other cell lines which express such antibodies and antigen-binding fragments thereof, nucleic acids, vectors, and host cells comprising nucleic acids which encode such antibodies and antigen-binding fragments thereof, and methods of use thereof are disclosed. In at least certain non-limiting embodiments, the antibodies or antigen-binding fragments thereof specifically bind to an epitope within isoform 2 or 4 of DCLK1 protein.

22 Claims, 28 Drawing Sheets
(13 of 28 Drawing Sheet(s) Filed in Color)
Specification includes a Sequence Listing.

(56) References Cited

OTHER PUBLICATIONS

Sureban, et al.; "Dclk1 Monoclonal Antibody-Based Car-T Cells a Novel Treatment Strategy Against Human Colorectal Cancers," Gastroenterology (2019) 156(6): S-96.
EP Application No. 18810790.8; Extended European Search Report dated Jan. 28, 2021.
KR Appl. No. 10-2019-7038154; Houchen, et al.; Office Action dated Mar. 10, 2021.
International Search Report dated Apr. 22, 2019, PCT/US2018/063702, filed Dec. 3, 2018.
Written Opinion of the international Searching Authority dated Apr. 22, 2019, in PCT/US2018/063702, filed Dec. 3, 2018.
Office Action dated Jan. 12, 2022, in U.S. Appl. No. 16/769,567, filed Jun. 3, 2020.
Response to Office Action dated Jun. 21, 2022, In U.S. Appl. No. 16/769,567, filed Jun. 3, 2020.
Office Action dated Aug. 5, 2022, in U.S. Appl. No. 16/769,567, filed Jun. 3, 2020.

\* cited by examiner

Caki-2

Caki-2-dsRed

Caki-2-dsRed-DCLK1

SEQUENCE LISTING

<160> NUMBER OF SEQ ID NOS: 32

<210> SEQ ID NO 1
<211> LENGTH: 740
<212> TYPE: PRT
<213> ORGANISM: Homo sapiens

<400> SEQUENCE: 1

```
Met Ser Phe Gly Arg Asp Met Glu Leu Glu His Phe Asp Glu Arg Asp
1               5                   10                  15

Lys Ala Gln Arg Tyr Ser Arg Gly Ser Arg Val Asn Gly Leu Pro Ser
            20                  25                  30

Pro Thr His Ser Ala His Cys Ser Phe Tyr Arg Thr Arg Thr Leu Gln
        35                  40                  45

Thr Leu Ser Ser Glu Lys Lys Ala Lys Lys Val Arg Phe Tyr Arg Asn
    50                  55                  60

Gly Asp Arg Tyr Phe Lys Gly Ile Val Tyr Ala Ile Ser Pro Asp Arg
65                  70                  75                  80

Phe Arg Ser Phe Glu Ala Leu Leu Ala Asp Leu Thr Arg Thr Leu Ser
                85                  90                  95

Asp Asn Val Asn Leu Pro Gln Gly Val Arg Thr Ile Tyr Thr Ile Asp
            100                 105                 110

Gly Leu Lys Lys Ile Ser Ser Leu Asp Gln Leu Val Glu Gly Glu Ser
        115                 120                 125

Tyr Val Cys Gly Ser Ile Glu Pro Phe Lys Lys Leu Glu Tyr Thr Lys
    130                 135                 140

Asn Val Asn Pro Asn Trp Ser Val Asn Val Lys Thr Thr Ser Ala Ser
145                 150                 155                 160

Arg Ala Val Ser Ser Leu Ala Thr Ala Lys Gly Ser Pro Ser Glu Val
                165                 170                 175

Arg Glu Asn Lys Asp Phe Ile Arg Pro Lys Leu Val Thr Ile Ile Arg
            180                 185                 190

Ser Gly Val Lys Pro Arg Lys Ala Val Arg Ile Leu Leu Asn Lys Lys
        195                 200                 205

Thr Ala His Ser Phe Glu Gln Val Leu Thr Asp Ile Thr Asp Ala Ile
    210                 215                 220

Lys Leu Asp Ser Gly Val Val Lys Arg Leu Tyr Thr Leu Asp Gly Lys
225                 230                 235                 240

Gln Val Met Cys Leu Gln Asp Phe Phe Gly Asp Asp Ile Phe Ile
                245                 250                 255

Ala Cys Gly Pro Glu Lys Phe Arg Tyr Gln Asp Asp Phe Leu Leu Asp
            260                 265                 270
```

-continued

```
Glu Ser Glu Cys Arg Val Val Lys Ser Thr Ser Tyr Thr Lys Ile Ala
            275                 280                 285

Ser Ser Ser Arg Arg Ser Thr Thr Lys Ser Pro Gly Pro Ser Arg Arg
290                 295                 300

Ser Lys Ser Pro Ala Ser Thr Ser Ser Val Asn Gly Thr Pro Gly Ser
305                 310                 315                 320

Gln Leu Ser Thr Pro Arg Ser Gly Lys Ser Pro Ser Pro Ser Pro Thr
            325                 330                 335

Ser Pro Gly Ser Leu Arg Lys Gln Arg Ser Ser Gln His Gly Gly Ser
            340                 345                 350

Ser Thr Ser Leu Ala Ser Thr Lys Val Cys Ser Ser Met Asp Glu Asn
    355                 360                 365

Asp Gly Pro Gly Glu Glu Val Ser Glu Glu Gly Phe Gln Ile Pro Ala
    370                 375                 380

Thr Ile Thr Glu Arg Tyr Lys Val Gly Arg Thr Ile Gly Asp Gly Asn
385                 390                 395                 400

Phe Ala Val Val Lys Glu Cys Val Glu Arg Ser Thr Ala Arg Glu Tyr
                405                 410                 415

Ala Leu Lys Ile Ile Lys Lys Ser Lys Cys Arg Gly Lys Glu His Met
            420                 425                 430

Ile Gln Asn Glu Val Ser Ile Leu Arg Arg Val Lys His Pro Asn Ile
    435                 440                 445

Val Leu Leu Ile Glu Glu Met Asp Val Pro Thr Glu Leu Tyr Leu Val
    450                 455                 460

Met Glu Leu Val Lys Gly Gly Asp Leu Phe Asp Ala Ile Thr Ser Thr
465                 470                 475                 480

Asn Lys Tyr Thr Glu Arg Asp Ala Ser Gly Met Leu Tyr Asn Leu Ala
                485                 490                 495

Ser Ala Ile Lys Tyr Leu His Ser Leu Asn Ile Val His Arg Asp Ile
            500                 505                 510

Lys Pro Glu Asn Leu Leu Val Tyr Glu His Gln Asp Gly Ser Lys Ser
            515                 520                 525

Leu Lys Leu Gly Asp Phe Gly Leu Ala Thr Ile Val Asp Gly Pro Leu
    530                 535                 540

Tyr Thr Val Cys Gly Thr Pro Thr Tyr Val Ala Pro Glu Ile Ile Ala
545                 550                 555                 560

Glu Thr Gly Tyr Gly Leu Lys Val Asp Ile Trp Ala Ala Gly Val Ile
                565                 570                 575

Thr Tyr Ile Leu Leu Cys Gly Phe Pro Pro Phe Arg Gly Ser Gly Asp
            580                 585                 590

Asp Gln Glu Val Leu Phe Asp Gln Ile Leu Met Gly Gln Val Asp Phe
            595                 600                 605

Pro Ser Pro Tyr Trp Asp Asn Val Ser Asp Ser Ala Lys Glu Leu Ile
    610                 615                 620

Thr Met Met Leu Leu Val Asp Val Asp Gln Arg Phe Ser Ala Val Gln
625                 630                 635                 640

Val Leu Glu His Pro Trp Val Asn Asp Gly Leu Pro Glu Asn Glu
                645                 650                 655

His Gln Leu Ser Val Ala Gly Lys Ile Lys His Phe Asn Thr Gly
            660                 665                 670

Pro Lys Pro Asn Ser Thr Ala Ala Gly Val Ser Val Ile Ala Thr Thr
    675                 680                 685

Ala Leu Asp Lys Glu Arg Gln Val Phe Arg Arg Arg Arg Asn Gln Asp
```

```
                690                 695                 700
Val Arg Ser Arg Tyr Lys Ala Gln Pro Ala Pro Glu Leu Asn Ser
705                 710                 715                 720

Glu Ser Glu Asp Tyr Ser Pro Ser Ser Glu Thr Val Arg Ser Pro
                725                 730                 735

Asn Ser Pro Phe
            740

<210> SEQ ID NO 2
<211> LENGTH: 433
<212> TYPE: PRT
<213> ORGANISM: Homo sapiens

<400> SEQUENCE: 2

Met Leu Glu Leu Ile Glu Val Asn Gly Thr Pro Gly Ser Gln Leu Ser
1               5                   10                  15

Thr Pro Arg Ser Gly Lys Ser Pro Ser Pro Ser Thr Ser Pro Gly
            20                  25                  30

Ser Leu Arg Lys Gln Arg Ser Ser Gln His Gly Gly Ser Ser Thr Ser
        35                  40                  45

Leu Ala Ser Thr Lys Val Cys Ser Ser Met Asp Glu Asn Asp Gly Pro
50                  55                  60

Gly Glu Glu Val Ser Glu Gly Phe Gln Ile Pro Ala Thr Ile Thr
65              70                  75                  80

Glu Arg Tyr Lys Val Gly Arg Thr Ile Gly Asp Gly Asn Phe Ala Val
                85                  90                  95

Val Lys Glu Cys Val Glu Arg Ser Thr Ala Arg Glu Tyr Ala Leu Lys
            100                 105                 110

Ile Ile Lys Lys Ser Lys Cys Arg Gly Lys Glu His Met Ile Gln Asn
        115                 120                 125

Glu Val Ser Ile Leu Arg Arg Val Lys His Pro Asn Ile Val Leu Leu
130                 135                 140

Ile Glu Glu Met Asp Val Pro Thr Glu Leu Tyr Leu Val Met Glu Leu
145                 150                 155                 160

Val Lys Gly Gly Asp Leu Phe Asp Ala Ile Thr Ser Thr Asn Lys Tyr
                165                 170                 175

Thr Glu Arg Asp Ala Ser Gly Met Leu Tyr Asn Leu Ala Ser Ala Ile
            180                 185                 190

Lys Tyr Leu His Ser Leu Asn Ile Val His Arg Asp Ile Lys Pro Glu
        195                 200                 205

Asn Leu Leu Val Tyr Glu His Gln Asp Gly Ser Lys Ser Leu Lys Leu
210                 215                 220

Gly Asp Phe Gly Leu Ala Thr Ile Val Asp Gly Pro Leu Tyr Thr Val
225                 230                 235                 240

Cys Gly Thr Pro Thr Tyr Val Ala Pro Glu Ile Ile Ala Glu Thr Gly
                245                 250                 255

Tyr Gly Leu Lys Val Asp Ile Trp Ala Ala Gly Val Ile Thr Tyr Ile
            260                 265                 270

Leu Leu Cys Gly Phe Pro Pro Phe Arg Gly Ser Gly Asp Asp Gln Glu
        275                 280                 285

Val Leu Phe Asp Gln Ile Leu Met Gly Gln Val Asp Phe Pro Ser Pro
290                 295                 300

Tyr Trp Asp Asn Val Ser Asp Ser Ala Lys Glu Leu Ile Thr Met Met
305                 310                 315                 320
```

-continued

```
Leu Leu Val Asp Val Asp Gln Arg Phe Ser Ala Val Gln Val Leu Glu
            325                 330                 335

His Pro Trp Val Asn Asp Gly Leu Pro Glu Asn Glu His Gln Leu
        340                 345                 350

Ser Val Ala Gly Lys Ile Lys Lys His Phe Asn Thr Gly Pro Lys Pro
            355                 360                 365

Asn Ser Thr Ala Ala Gly Val Ser Val Ile Ala Thr Ala Leu Asp
    370                 375                 380

Lys Glu Arg Gln Val Phe Arg Arg Arg Asn Gln Asp Val Arg Ser
385                 390                 395                 400

Arg Tyr Lys Ala Gln Pro Ala Pro Glu Leu Asn Ser Glu Ser Glu
            405                 410                 415

Asp Tyr Ser Pro Ser Ser Ser Glu Thr Val Arg Ser Pro Asn Ser Pro
            420                 425                 430

Phe

<210> SEQ ID NO 3
<211> LENGTH: 14
<212> TYPE: PRT
<213> ORGANISM: Homo sapiens

<400> SEQUENCE: 3

Arg Arg Arg Asn Gln Asp Val Arg Ser Arg Tyr Lys Ala Gln
1               5                   10

<210> SEQ ID NO 4
<211> LENGTH: 12
<212> TYPE: PRT
<213> ORGANISM: Homo sapiens

<400> SEQUENCE: 4

Glu Leu Asn Ser Glu Ser Glu Asp Tyr Ser Pro Ser
1               5                   10

<210> SEQ ID NO 5
<211> LENGTH: 11
<212> TYPE: PRT
<213> ORGANISM: Homo sapiens

<400> SEQUENCE: 5

Asp Val Arg Ser Arg Tyr Lys Ala Gln Pro Ala
1               5                   10

<210> SEQ ID NO 6
<211> LENGTH: 15
<212> TYPE: PRT
<213> ORGANISM: Homo sapiens

<400> SEQUENCE: 6

Pro Glu Leu Asn Ser Glu Ser Glu Asp Tyr Ser Pro Ser Ser Ser
1               5                   10                  15

<210> SEQ ID NO 7
<211> LENGTH: 15
<212> TYPE: PRT
<213> ORGANISM: Homo sapiens

<400> SEQUENCE: 7

Arg Ser Arg Tyr Lys Ala Gln Pro Ala Pro Glu Leu Asn Ser
1               5                   10                  15
```

```
<210> SEQ ID NO 8
<211> LENGTH: 14
<212> TYPE: PRT
<213> ORGANISM: Homo sapiens

<400> SEQUENCE: 8

Asp Val Arg Ser Arg Tyr Lys Ala Gln Pro Ala Pro Pro Glu
1               5                   10

<210> SEQ ID NO 9
<211> LENGTH: 15
<212> TYPE: PRT
<213> ORGANISM: Homo sapiens

<400> SEQUENCE: 9

Arg Tyr Lys Ala Gln Pro Ala Pro Pro Glu Leu Asn Ser Glu Ser
1               5                   10                  15

<210> SEQ ID NO 10
<211> LENGTH: 17
<212> TYPE: PRT
<213> ORGANISM: Homo sapiens

<400> SEQUENCE: 10

Asp Tyr Ser Pro Ser Ser Ser Glu Thr Val Arg Ser Pro Asn Ser Pro
1               5                   10                  15

Phe

<210> SEQ ID NO 11
<211> LENGTH: 15
<212> TYPE: PRT
<213> ORGANISM: Homo sapiens

<400> SEQUENCE: 11

Glu Asp Tyr Ser Pro Ser Ser Ser Glu Thr Val Arg Ser Pro Asn
1               5                   10                  15

<210> SEQ ID NO 12
<211> LENGTH: 14
<212> TYPE: PRT
<213> ORGANISM: Homo sapiens

<400> SEQUENCE: 12

Glu Ser Glu Asp Tyr Ser Pro Ser Ser Ser Glu Thr Val Arg
1               5                   10

<210> SEQ ID NO 13
<211> LENGTH: 357
<212> TYPE: DNA
<213> ORGANISM: Artificial Sequence
<220> FEATURE:
<223> OTHER INFORMATION: Synthetic nucleotide; HC variable cDNA sequence
      of CBT-15A

<400> SEQUENCE: 13
gacgtgaagc tcgtggagtc tgggggaggc ttagtgaagc ttggagggtc cctgaaactc      60
tcctgtgcag cctctggatt cactttcagt agctattaca tgtcttgggt tcgccagact     120
ccagagaaga ggctggagtt ggtcgcagcc attaatagta tggtggtag cacctactat      180 ccagacactg tgaagggccg attcaccatc tccagagaca tgccaagaa caccctgtac      240 ctgcaaatga gcagtctgaa gtctgaggac acagccttgt attactgtgc aagacatggg     300
ggtaactact ggtacttcga tgtctggggc gcagggacca cggtcaccgt ctcctca        357
```

<210> SEQ ID NO 14
<211> LENGTH: 119
<212> TYPE: PRT
<213> ORGANISM: Artificial Sequence
<220> FEATURE:
<223> OTHER INFORMATION: Synthetic peptide; HC variable AA sequence of
      CBT-15A

<400> SEQUENCE: 14

Asp Val Lys Leu Val Glu Ser Gly Gly Gly Leu Val Lys Leu Gly Gly
1               5                   10                  15

Ser Leu Lys Leu Ser Cys Ala Ala Ser Gly Phe Thr Phe Ser Ser Tyr
            20                  25                  30

Tyr Met Ser Trp Val Arg Gln Thr Pro Glu Lys Arg Leu Glu Leu Val
        35                  40                  45

Ala Ala Ile Asn Ser Asn Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Leu Tyr Tyr Cys
                85                  90                  95

Ala Arg His Gly Gly Asn Tyr Trp Tyr Phe Asp Val Trp Gly Ala Gly
            100                 105                 110

Thr Thr Val Thr Val Ser Ser
        115

<210> SEQ ID NO 15
<211> LENGTH: 339
<212> TYPE: DNA
<213> ORGANISM: Artificial Sequence
<220> FEATURE:
<223> OTHER INFORMATION: Synthetic nucleotide; LC variable cDNA sequence
      of CBT-15A

<400> SEQUENCE: 15
gacattgtga tgtcacagtc tccatcctcc ctagctgtgt cagttggaga agaggttact      60
atgagctgca agtccagtca gagccttttta tatagtagca atcaaaagaa ctacttggcc     120
tggtaccagc agaaaccagg gcagtctcct aaactgctga tttactgggc atccactagg    180
gaatctgggg tccctgatcg cttcacaggc agtggatctg ggacagattt cactctcacc    240
atcagcagtg tgaaggctga agacctggca gtttattact gtcagcaata ttatagctat    300
ccgtacacgt tcggaggggg gaccaagctg gaaataaaa                            339

<210> SEQ ID NO 16
<211> LENGTH: 113
<212> TYPE: PRT
<213> ORGANISM: Artificial Sequence
<220> FEATURE:
<223> OTHER INFORMATION: Synthetic peptide; LC variable AA sequence of
      CBT-15A

<400> SEQUENCE: 16

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val

```
                  50                  55                  60
Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                 85                  90                  95

Tyr Tyr Ser Tyr Pro Tyr Thr Phe Gly Gly Gly Thr Lys Leu Glu Ile
                100                 105                 110
Lys

<210> SEQ ID NO 17
<211> LENGTH: 8
<212> TYPE: PRT
<213> ORGANISM: Artificial Sequence
<220> FEATURE:
<223> OTHER INFORMATION: Synthetic peptide; VH CDR1 of CBT-15A

<400> SEQUENCE: 17

Gly Phe Thr Phe Ser Ser Tyr Tyr
 1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide; VH CDR2 of CBT-15A

<400> SEQUENCE: 18

Ile Asn Ser Asn Gly Gly Ser Thr
 1               5

<210> SEQ ID NO 19
<211> LENGTH: 12
<212> TYPE: PRT
<213> ORGANISM: Artificial Sequence
<220> FEATURE:
<223> OTHER INFORMATION: Synthetic peptide; VH CDR3 of CBT-15A

<400> SEQUENCE: 19

Ala Arg His Gly Gly Asn Tyr Trp Tyr Phe Asp Val
 1               5                  10

<210> SEQ ID NO 20
<211> LENGTH: 12
<212> TYPE: PRT
<213> ORGANISM: Artificial Sequence
<220> FEATURE:
<223> OTHER INFORMATION: Synthetic peptide; VL CDR1 of CBT-15A

<400> SEQUENCE: 20

Gln Ser Leu Leu Tyr Ser Ser Asn Gln Lys Asn Tyr
 1               5                  10

<210> SEQ ID NO 21
<211> LENGTH: 3
<212> TYPE: PRT
<213> ORGANISM: Artificial Sequence
<220> FEATURE:
<223> OTHER INFORMATION: Synthetic peptide; VL CDR2 of CBT-15A

<400> SEQUENCE: 21

Trp Ala Ser
 1
```

<210> SEQ ID NO 22
<211> LENGTH: 9
<212> TYPE: PRT
<213> ORGANISM: Artificial Sequence
<220> FEATURE:
<223> OTHER INFORMATION: Synthetic peptide; VL CDR3 of CBT-15A

<400> SEQUENCE: 22

```
Gln Gln Tyr Tyr Ser Tyr Pro Tyr Thr
1               5
```

<210> SEQ ID NO 23
<211> LENGTH: 351
<212> TYPE: DNA
<213> ORGANISM: Artificial Sequence
<220> FEATURE:
<223> OTHER INFORMATION: Synthetic nucleotide; HC variable cDNA sequence
      of CBT-15G

<400> SEQUENCE: 23

```
gaggtccagc tgcagcagtc tgggactgcg ctggcaaggc ctggggcttc cgtgaagatg      60
tcctgcaagg cttctggcta cagctttacc agctactgga tgcactgggt aaaacagagg     120
cctggacagg gtctagaatg gattggtgct atttatcctg gaaaaagtga tactagctac     180
aaccagaagt tcaagggcaa ggccaaactg actgcagtca catccgccag cactgcctac     240
atggagctca gcagcctgac aaatgaggac tctgcggtct attactgtac aagatatggt     300
aagggtgcta tggactactg gggtcaagga acctcagtca ccgtctcctc a              351
```

<210> SEQ ID NO 24
<211> LENGTH: 117
<212> TYPE: PRT
<213> ORGANISM: Artificial Sequence
<220> FEATURE:
<223> OTHER INFORMATION: Synthetic peptide; HC variable AA sequence of
      CBT-15G

<400> SEQUENCE: 24

```
Glu Val Gln Leu Gln Gln Ser Gly Thr Ala Leu Ala Arg Pro Gly Ala
1               5                   10                  15

Ser Val Lys Met Ser Cys Lys Ala Ser Gly Tyr Ser Phe Thr Ser Tyr
            20                  25                  30

Trp Met His Trp Val Lys Gln Arg Pro Gly Gln Gly Leu Glu Trp Ile
        35                  40                  45

Gly Ala Ile Tyr Pro Gly Lys Ser Asp Thr Ser Tyr Asn Gln Lys Phe
    50                  55                  60

Lys Gly Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95

Thr Arg Tyr Gly Lys Gly Ala Met Asp Tyr Trp Gly Gln Gly Thr Ser
            100                 105                 110

Val Thr Val Ser Ser
        115
```

<210> SEQ ID NO 25
<211> LENGTH: 321
<212> TYPE: DNA
<213> ORGANISM: Artificial Sequence
<220> FEATURE:
<223> OTHER INFORMATION: Synthetic nucleotide; LC variable cDNA sequence
      of CBT-15G

<400> SEQUENCE: 25

```
gacattgtgc tgacccaatc tcacaaattc atgtccacat cagtaggaga cagggtcacc      60
atcacctgca aggccagtca ggatgtgaat actgctgtag cctggtatca aaaaaaacca     120
gggcaatctc ctaaactgct gatttactgg gcatccaccc ggctcactgg agtccctgat     180
cgcttcacag gcagtggatc tgggacagat tatactctca ccatcagcag tgtgcaggct     240
gaagacctgg cactttatta ctgtcagcaa cattatagta ctccgtacac gttcggaggg     300
gggaccaagc tggaaataaa a                                                321
```

<210> SEQ ID NO 26
<211> LENGTH: 107
<212> TYPE: PRT
<213> ORGANISM: Artificial Sequence
<220> FEATURE:
<223> OTHER INFORMATION: Synthetic peptide; LC variable AA sequence of
      CBT-15G

<400> SEQUENCE: 26

```
Asp Ile Val Leu Thr Gln Ser His Lys Phe Met Ser Thr Ser Val Gly
1               5                   10                  15

Asp Arg Val Thr Ile Thr Cys Lys Ala Ser Gln Asp Val Asn Thr Ala
            20                  25                  30

Val Ala Trp Tyr Gln Lys Lys Pro Gly Gln Ser Pro Lys Leu Leu Ile
        35                  40                  45

Tyr Trp Ala Ser Thr Arg Leu Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ser Thr Pro Tyr
                85                  90                  95

Thr Phe Gly Gly Gly Thr Lys Leu Glu Ile Lys
            100                 105
```

<210> SEQ ID NO 27
<211> LENGTH: 5
<212> TYPE: PRT
<213> ORGANISM: Artificial Sequence
<220> FEATURE:
<223> OTHER INFORMATION: Synthetic peptide; VH CDR1 of CBT-15G

<400> SEQUENCE: 27

```
Ser Tyr Trp Met His
1               5
```

<210> SEQ ID NO 28
<211> LENGTH: 17
<212> TYPE: PRT
<213> ORGANISM: Artificial Sequence
<220> FEATURE:
<223> OTHER INFORMATION: Synthetic peptide; VH CDR2 of CBT-15G

<400> SEQUENCE: 28

```
Ala Ile Tyr Pro Gly Lys Ser Asp Thr Ser Tyr Asn Gln Lys Phe Lys
1               5                   10                  15

Gly
```

<210> SEQ ID NO 29
<211> LENGTH: 8
<212> TYPE: PRT
<213> ORGANISM: Artificial Sequence

```
<220> FEATURE:
<223> OTHER INFORMATION: Synthetic peptide; VH CDR3 of CBT-15G

<400> SEQUENCE: 29

Tyr Gly Lys Gly Ala Met Asp Tyr
1               5

<210> SEQ ID NO 30
<211> LENGTH: 11
<212> TYPE: PRT
<213> ORGANISM: Artificial Sequence
<220> FEATURE:
<223> OTHER INFORMATION: Synthetic peptide; VL CDR1 of CBT-15G

<400> SEQUENCE: 30

Lys Ala Ser Gln Asp Val Asn Thr Ala Val Ala
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Synthetic peptide; VL CDR2 of CBT-15G

<400> SEQUENCE: 31

Trp Ala Ser Thr Arg Leu Thr
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic peptide; VL CDR3 of CBT-15G

<400> SEQUENCE: 32

Gln Gln His Tyr Ser Thr Pro Tyr Thr
1               5
```

ANTI-DOUBLECORTIN-LIKE KINASE 1 ANTIBODIES AND METHODS OF USE

BACKGROUND

Renal cell carcinoma (RCC) is the 8th most common cancer in the world and in the US it accounted for approximately 7% of all malignancies in men and 4% in women. Of note, nearly 48% of RCC patients present with regional spread or distant metastases leading to high mortality. Moreover, there is a strong predilection for recurrence in 40% of patients following surgical resection. To complicate matters, RCC is a highly intractable tumor because of its strong resistance to chemotherapies and radiation. Currently, targeted treatments include immunotherapy and receptor tyrosine kinase (RTK) and mTOR inhibitors. However, these do not result in complete responses, and additional research into the molecular and cellular drivers of RCC is needed to improve patient outcomes.

Renal cell cancer is characterized by slow-growth, a hypoxic microenvironment, and devastating resistance to drug and radiation therapy. These characteristics are consistent with the presence of tumor stem or stem-like cells. Previous findings demonstrated that the gastrointestinal tumor stem cell (TSC) marker Doublecortin-like kinase 1 (DCLK1) is epigenetically dysregulated and overexpressed in RCC. Moreover, the targeted downregulation of DCLK1 in RCC cell lines leads to significant decreases in molecular and functional hallmarks of tumorigenesis and metastasis.

The significant proportion of patients diagnosed with metastatic disease on presentation and the tendency for recurrence may be explained by intra-tumor heterogeneity and by the presence of strong epithelial to mesenchymal transition (EMT) characteristics in RCC. Inactivation of the Von-Hippel Lindau (VHL) tumor suppressor gene plays an important role in RCC tumorigenesis by interfering with proteasomal degradation of hypoxia-inducible transcription factors (HIF). HIF is involved in the response to hypoxia which in turn provides a supportive environment for tumor stem cells (TSCs). TSCs are known to confer an EMT phenotype and resistance to therapy, which are key characteristics of RCC. These findings suggest that the development and progression of RCC may be tightly associated with tumor stem or stem-like cells.

DCLK1 is a member of the calmodulin-dependent kinase family and is expressed in many cancers including colon, pancreas, liver, and esophagus. DCLK1 is a TSC-specific marker and is highly correlated to cancer initiation, EMT, and progression of gastrointestinal tumors. Studies of DCLK1's role in tumorigenesis in non-gastrointestinal tumors are limited. However, we recently reported DCLK1's epigenetic dysregulation and overexpression at the gene and protein level in RCC tumors (Weygant N, Qu D, May R, Tierney R M, Berry W L, Zhao L, et al. DCLK1 is a broadly dysregulated target against epithelial-mesenchymal transition, focal adhesion, and sternness in clear cell renal carcinoma. Oncotarget. 2015; 6(4):2193-205). DCLK1 comprises four primary human isoforms from two promoters termed alpha and beta. Evidence indicates that these isoforms have differing functions and expression levels in cancers. All isoforms have a shared kinase domain and autophosphorylation region. The alpha promoter produces two doublecortin-binding 82 kDa isoforms (1 and 2) with differing C-terminal regions. The beta promoter produces two shortened primarily kinase domain 52 kDa isoforms (3 and 4) with equivalent but differing C-terminal regions.

BRIEF DESCRIPTION OF THE DRAWINGS

This patent or application file contains at least one drawing executed in color. Copies of this patent or patent application publication with color drawings will be provided by the Office upon request and payment of the necessary fee.

DETAILED DESCRIPTION

Figure 1:
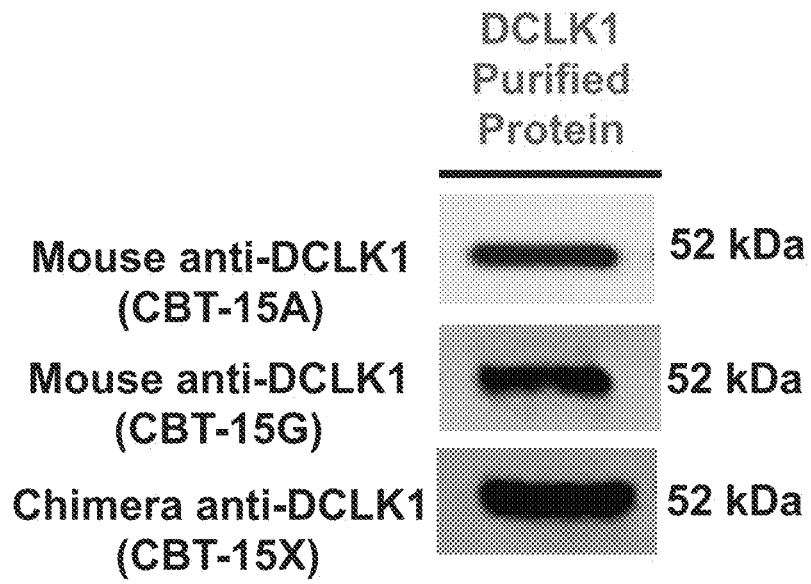
FIG. 1 shows Western blots demonstrating that CBT-15 monoclonal antibodies (A, G, and X) detect purified DCLK1 isoform 4 protein.

The present disclosure is directed to antibodies and antigen-binding fragments thereof that specifically bind to human DCLK1 protein, and to hybridomas or other cell lines which express such antibodies and antigen-binding fragments thereof, and to nucleic acids, vectors, and host cells comprising nucleic acids which encode such antibodies and antigen-binding fragments thereof. In at least certain embodiments, the antibodies or antigen-binding fragments thereof specifically bind to an epitope within DCLK1 isoform 2 (SEQ ID NO:1) or DCLK1 isoform 4 (SEQ ID NO:2). In particular embodiments the isoform 2 or 4 epitopes comprise the amino acid sequences SEQ ID NOS: 3-12, more particularly SEQ ID NO:10. The disclosed antibodies and antigen-binding fragments thereof can be used in the treatment and diagnoses of DCLK1-expressing cancers, as well as for detecting the DCLK1 protein and cells which express the DCLK1 protein. DCLK1 is not only a factor in development of certain cancers such as RCC, but as demonstrated herein, is also a therapeutic target for the treatment of cancers which express DCLK1. Examples of such cancers include but are not limited to, gastrointestinal cancers (i.e., colon, rectum, intestinal, stomach, esophagus), breast cancer, lung cancer, renal cancer, pancreatic cancer, liver cancer, bladder cancer, uterine cancer, and ovarian cancer. The present disclosure is thus directed in certain embodiments to methods of treating subjects afflicted with such cancers.

Before further describing various embodiments of the present disclosure in more detail by way of exemplary description, examples, and results, it is to be understood that the compounds, compositions, and methods of present disclosure are not limited in application to the details of specific embodiments and examples as set forth in the following description. The description provided herein is intended for purposes of illustration only and is not intended to be construed in a limiting sense. As such, the language used herein is intended to be given the broadest possible scope and meaning; and the embodiments and examples are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the present disclosure. However, it will be apparent to a person having ordinary skill in the art that the present disclosure may be practiced without these specific details. In other instances, features which are well known to persons of ordinary skill in the art have not been described in detail to avoid unnecessary complication of the description. It is intended that all alternatives, substitutions, modifications and equivalents apparent to those having ordinary skill in the art are included within the scope of the present disclosure. All of the compounds, compositions, and methods and application and uses thereof disclosed herein can be made and executed without undue experimentation in light of the present disclosure. Thus, while the compounds, compositions, and methods of the present disclosure have been described in terms of particular embodiments, it will be apparent to those of skill in the art that variations may be applied to the compounds, compositions, and methods and in the steps or in the sequence of steps of the methods described herein without departing from the concept, spirit, and scope of the inventive concepts.

All patents, published patent applications, and non-patent publications including published articles mentioned in the specification or referenced in any portion of this application, are herein expressly incorporated by reference in their entirety to the same extent as if each individual patent or publication was specifically and individually indicated to be incorporated by reference.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular. Where used herein, the specific term "single" is limited to only "one."

As utilized in accordance with the methods, compounds, and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example. Reference to an integer with more (greater) or less than includes any number greater or less than the reference number, respectively. Thus, for example, reference to less than 100 includes 99, 98, 97, etc. all the way down to the number one (1); and less than 10 includes 9, 8, 7, etc. all the way down to the number one (1).

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately," where used herein when referring to a measurable value such as an amount, a temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment and may be included in other embodiments. The appearances of the phrase "in one embodiment" in various places in the specification are not necessarily all referring to the same embodiment and are not necessarily limited to a single or particular embodiment.

The term "pharmaceutically acceptable" refers to compounds and compositions which are suitable for administration to humans and/or animals without undue adverse side effects such as toxicity, irritation and/or allergic response commensurate with a reasonable benefit/risk ratio. The compounds or conjugates of the present disclosure may be combined with one or more pharmaceutically-acceptable excipients, including carriers, vehicles, and diluents which may improve solubility, deliverability, dispersion, stability, and/or conformational integrity of the compounds or conjugates thereof.

By "biologically active" is meant the ability to modify the physiological system of an organism without reference to how the active agent has its physiological effects.

As used herein, "pure," or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

Non-limiting examples of animals or subjects within the scope and meaning of this term include dogs, cats, rats, mice, guinea pigs, chinchillas, horses, goats, cattle, sheep, zoo animals, Old and New World monkeys, non-human primates, and humans.

"Treatment" refers to therapeutic treatments. "Prevention" refers to prophylactic or preventative treatment measures or reducing the onset of a condition or disease. The term "treating" refers to administering the composition to a subject for therapeutic purposes and/or for prevention.

The terms "therapeutic composition" and "pharmaceutical composition" refer to an active agent-containing composition that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "effective amount" refers to an amount of an active agent which is sufficient to exhibit a detectable therapeutic or treatment effect in a subject without excessive adverse side effects (such as substantial toxicity, irritation and allergic response) commensurate with a reasonable benefit/risk ratio when used in the manner of the present disclosure. The effective amount for a subject will depend upon the subject's type, size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "ameliorate" means a detectable or measurable improvement in a subject's condition, disease or symptom thereof. A detectable or measurable improvement includes a subjective or objective decrease, reduction, inhibition, suppression, limit or control in the occurrence, frequency, severity, progression, or duration of the condition or disease, or an improvement in a symptom or an underlying cause or a consequence of the disease, or a reversal of the disease. A successful treatment outcome can lead to a "therapeutic effect," or "benefit" of ameliorating, decreasing, reducing, inhibiting, suppressing, limiting, controlling or preventing the occurrence, frequency, severity, progression, or duration of a disease or condition, or consequences of the disease or condition in a subject.

A decrease or reduction in worsening, such as stabilizing the condition or disease, is also a successful treatment outcome. A therapeutic benefit therefore need not be complete ablation or reversal of the disease or condition, or any one, most or all adverse symptoms, complications, consequences or underlying causes associated with the disease or condition. Thus, a satisfactory endpoint may be achieved when there is an incremental improvement such as a partial decrease, reduction, inhibition, suppression, limit, control or prevention in the occurrence, frequency, severity, progression, or duration, or inhibition or reversal of the condition or disease (e.g., stabilizing), over a short or long duration of time (hours, days, weeks, months, etc.). Effectiveness of a method or use, such as a treatment that provides a potential therapeutic benefit or improvement of a condition or disease, can be ascertained by various methods and testing assays.

The terms DCLK1 isoform 2 and DCLK1 isoform 4 refer to polypeptide isoforms produced from transcript sequences represented in RefSeq NM_001330072.1 (isoform 2) and NM_001195416.1 (isoform 4). DCLK1 isoform 2 is further defined as having the amino acid sequence SEQ ID NO:1 (Table 1) and DCLK1 isoform 4 is further defined as having the amino acid sequence SEQ ID NO:2 (Table 2).

TABLE 1

Amino acid sequence of DCLK1 isoform 2

MSFGRDMELEHFDERDKAQRYSRGSRVNGLPSPTHSAHCSFYRTRTLQTL

SSEKKAKKVRFYRNGDRYFKGIVYAISPDRFRSFEALLADLTRTLSDNVN

LPQGVRTIYTIDGLKKISSLDQLVEGESYVCGSIEPFKKLEYTKNVNPNW

SVNVKTTSASRAVSSLATAKGSPSEVRENKDFIRPKLVTIIRSGVKPRKA

VRILLNKKTAHSFEQVLTDITDAIKLDSGVVKRLYTLDGKQVMCLQDFFG

DDDIFIACGPEKFRYQDDFLLDESECRVVKSTSYTKIASSSRRSTTKSPG

PSRRSKSPASTSSVNGTPGSQLSTPRSGKSPSPSPTSPGSLRKQRSSQHG

GSSTSLASTKVCSSMDENDGPGEEVSEEGFQIPATITERYKVGRTIGDGN

FAVVKECVERSTAREYALKIIKKSKCRGKEHMIQNEVSILRRVKHPNIVL

LIEEMDVPTELYLVMELVKGGDLFDAITSTNKYTERDASGMLYNLASAIK

YLHSLNIVHRDIKPENLLVYEHQDGSKSLKLGDFGLATIVDGPLYTVCGT

PTYVAPEIIAETGYGLKVDIWAAGVITYILLCGFPPFRGSGDDQEVLFDQ

ILMGQVDFPSPYWDNVSDSAKELITMMLLVDVDQRFSAVQVLEHPWVNDD

GLPENEHQLSVAGKIKKHFNTGPKPNSTAAGVSVIATTALDKERQVFRRR

RNQDVRSRYKAQPAPPELNSESEDYSPSSSETVRSPNSPF.

TABLE 2

Amino acid sequence of DCLK1 isoform 4

MLELIEVNGTPGSQLSTPRSGKSPSPSPTSPGSLRKQRSSQHGGSSTSLA

STKVCSSMDENDGPGEEVSEEGFQIPATITERYKVGRTIGDGNFAVVKEC

VERSTAREYALKIIKKSKCRGKEHMIQNEVSILRRVKHPNIVLLIEEMDV

PTELYLVMELVKGGDLFDAITSTNKYTERDASGMLYNLASAIKYLHSLNI

TABLE 2-continued

Amino acid sequence of DCLK1 isoform 4

VHRDIKPENLLVYEHQDGSKSLKLGDFGLATIVDGPLYTVCGTPTYVAPE

IIAETGYGLKVDIWAAGVITYILLCGFPPFRGSGDDQEVLFDQILMGQVD

FPSPYWDNVSDSAKELITMMLLVDVDQRFSAVQVLEHPWVNDDGLPENEH

QLSVAGKIKKHFNTGPKPNSTAAGVSVIATTALDKERQVFRRRRNQDVRS

RYKAQPAPPELNSESEDYSPSSSETVRSPNSPF.

The term "antibody" as used herein can refer to both intact, "full length" antibodies as well as to DCLK1-binding fragments (also referred to herein as antigen binding fragments, antigen binding portions, binding fragments, or binding portions) thereof. As used herein, the term "antibody" includes, but is not limited to, synthetic antibodies, monoclonal antibodies, recombinantly produced antibodies, intrabodies, multispecific antibodies (including bi-specific antibodies), human antibodies, humanized antibodies, chimeric antibodies, recombinant single chain polypeptide molecules in which light and heavy chain variable regions are connected by a peptide linker, i.e., single-chain Fv (scFv) fragments, bivalent scFv (bi-scFv), trivalent scFv (tri-scFv), Fab fragments, Fab' fragments, F(ab') fragments, F(ab')$_2$ fragments, F(ab)$_2$ fragments, disulfide-linked Fvs (sdFv) (including bi-specific sdFvs), and anti-idiotypic (anti-Id) antibodies, diabodies, dAb fragments, nanobodies, diabodies, triabodies, tetrabodies, linear antibodies, isolated CDRs, and epitope-binding fragments of any of the above. Regardless of structure, an antibody fragment binds with the same antigen that is recognized by the intact antibody. For example, an anti-DCLK1 antibody fragment binds with an epitope of DCLK1. Fragments can be produced by recombinant DNA techniques, or by enzymatic or chemical separation of intact immunoglobulins.

The antibodies of several embodiments provided herein may be monospecific, bispecific, trispecific or of greater multispecificity, such as multispecific antibodies formed from antibody fragments. The term "antibody" also includes a diabody (homodimeric Fv fragment) or a minibody (V$_L$-V$_H$-C$_{H3}$), a bispecific antibody or the like. A bispecific or bifunctional antibody is an artificial hybrid antibody having two different heavy/light chain pairs and two different binding sites. Multispecific antibodies may be specific for different epitopes of a polypeptide or may be specific for both a polypeptide as well as for a heterologous epitope, such as a heterologous polypeptide or solid support material. Single chain antibodies produced by joining antibody fragments using recombinant methods, or a synthetic linker, are also encompassed by the present disclosure (e.g., see International Patent Application Publication Nos. WO 93/17715; WO 92/08802; WO 91/00360; and WO 92/05793; and U.S. Pat. Nos. 4,474,893; 4,714,681; 4,925,648; 5,573,920; and 5,601,819).

The term "monoclonal antibody" as used herein refers to an antibody obtained from a population of substantially homogeneous antibodies, i.e., the individual antibodies comprising the population are identical except for possible naturally occurring mutations that may be present in minor amounts. The modifier "monoclonal" indicates the character of the antibody as being obtained from a substantially homogeneous population of antibodies, and is not to be construed as requiring production of the antibody by any particular method. For example, the monoclonal antibodies to DCLK1 isoforms 2 and 4 used in accordance with the present disclosure can be made by the hybridoma method first described by Kohler et al. Nature 256:495 (1975), or may be made by recombinant DNA methods (see, for example, U.S. Pat. No. 4,816,567).

The compositions, formulations and methods described herein may include monoclonal antibodies. Rodent monoclonal antibodies to specific antigens may be obtained by methods known to those skilled in the art (e.g., see Kohler and Milstein, op.cit., and Coligan et al. (eds.), Current Protocols in Immunology, Vol. 1, pages 2.5.1-2.6.7 (John Wiley & Sons 1991)). General techniques for cloning murine immunoglobulin variable domains have been disclosed, for example, by the publication of Orlandi et al., Proc. Nat'l Acad. Sci. USA 86: 3833 (1989).

An "isolated" antibody refers to an antibody that has been identified and separated and/or recovered from components of its natural environment and/or an antibody that is recombinantly produced. A "purified antibody" is an antibody that is typically at least 50% w/w pure of interfering proteins and other contaminants arising from its production or purification but does not exclude the possibility that the monoclonal antibody is combined with an excess of pharmaceutical acceptable carrier(s) or other vehicle intended to facilitate its use. Interfering proteins and other contaminants can include, for example, cellular components of the cells from which an antibody is isolated or recombinantly produced. Sometimes monoclonal antibodies are at least 60%, 70%, 80%, 90%, 95 or 99% w/w pure of interfering proteins and contaminants from production or purification. The antibodies described herein, including murine, chimeric, and humanized antibodies can be provided in isolated and/or purified form.

A "therapeutic agent" is an atom, molecule, or compound that is useful in the treatment of a disease. Examples of therapeutic agents include but are not limited to antibodies, antibody fragments, drugs, cytokine or chemokine inhibitors, pro-apoptotic agents, tyrosine kinase inhibitors, toxins, enzymes, nucleases, hormones, immunomodulators, antisense oligonucleotides, siRNA, RNAi, chelators, boron compounds, photoactive agents, dyes and radioisotopes.

A "diagnostic agent" is an atom, molecule, or compound that is useful in diagnosing a disease. Useful diagnostic agents include, but are not limited to, radioisotopes, dyes, contrast agents, fluorescent compounds or molecules and enhancing agents (e.g., paramagnetic ions). In certain particular (but non-limiting) embodiments, the diagnostic agents are selected from the group comprising radioisotopes, enhancing agents, and fluorescent compounds.

An "immunoconjugate" or "antibody-drug conjugate" is a conjugate of an antibody with an atom, molecule, or a higher-ordered structure (e.g., with a liposome), a therapeutic agent, or a diagnostic agent. The term "antibody" as used herein can also refer to both intact antibodies, and to DCLK1-binding fragments, which are conjugated to a therapeutic agent (e.g., a cytotoxic or cytostatic drug) or to a diagnostic agent.

As used herein, the term "antibody fusion protein" is a recombinantly produced antigen-binding molecule in which an antibody or antibody fragment is linked to another protein or peptide, such as the same or different antibody or antibody fragment. The fusion protein may comprise a single antibody component, a multivalent or multispecific combination of different antibody components or multiple copies of the same antibody component. The fusion protein may additionally comprise an antibody or an antibody fragment and a therapeutic agent.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 120 or more amino acids, including portions called complementarity determining regions as described below, primarily responsible for antigen recognition. This variable region is initially expressed linked to a cleavable signal peptide. The variable region without the signal peptide is sometimes referred to as a mature variable region. Thus, for example, a light chain mature variable region, means a light chain variable region without the light chain signal peptide. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. (See generally, Fundamental Immunology (Paul, W, ed., 2nd ed. Raven Press, N.Y., 1989, Ch. 7, incorporated by reference in its entirety for all purposes).

The mature variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md., 1987 and 1991), or Chothia & Lesk, J. Mol. Biol. 196:901-917 (1987); Chothia et al., Nature 342:878-883 (1989). Kabat also provides a widely used numbering convention (Kabat numbering) in which corresponding residues between different heavy chains or between different light chains are assigned the same number.

In certain embodiments, the presently disclosed antibodies, or antigen-binding portions thereof, contain at least one heavy chain variable region and/or at least one light chain variable region. The heavy chain variable region (or light chain variable region) may contain three CDRs and four framework regions (FRs), arranged from amino-terminus to carboxy-terminus in the following order: FR1, CDR1, FR2, CDR2, FR3, CDR3, FR4.

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Also within the scope of the present disclosure are antibodies or antigen-binding portions thereof in which specific amino acids have been substituted, deleted or added. These alternations do not have a substantial effect on the peptide's biological properties such as binding activity. For example, antibodies may have amino acid substitutions in the framework region, such as to improve binding to the antigen. In another example, a selected, small number of acceptor framework residues can be replaced by the corresponding donor amino acids. The donor framework can be a mature or germline human antibody framework sequence or a consensus sequence. Guidance concerning how to make phenotypically silent amino acid substitutions is provided in Bowie et al., Science, 247: 1306-1310 (1990). Cunningham et al., Science, 244: 1081-1085 (1989). Ausubel (ed.), Current Protocols in Molecular Biology, John Wiley and Sons, Inc. (1994). T. Maniatis, E. F. Fritsch and J. Sambrook, Molecular Cloning: A Laboratory Manual, Cold Spring Harbor laboratory, Cold Spring Harbor, N.Y. (1989). Pearson, Methods Mol. Biol. 243:307-31 (1994). Gonnet et al., Science 256:1443-45 (1992).

For purposes of classifying amino acids substitutions as conservative or nonconservative, amino acids are grouped in one embodiment as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same group. Nonconservative substitutions constitute exchanging a member of one of these groups for a member of another.

Tables of conservative amino acid substitutions have been constructed and are known in the art. In other embodiments, examples of interchangeable amino acids include, but are not limited to the following: arginine and lysine; glutamate and aspartate; serine and threonine; glutamine and asparagine; and valine, leucine and isoleucine. In other embodiments, the following substitutions can be made: Ala (A) by leu, ile, or val; Arg (R) by gln, asn, or lys; Asn (N) by his, asp, lys, arg, or gln; Asp (D) by asn, or glu; Cys (C) by ala, or ser; Gln (Q) by glu, or asn; Glu (E) by gln, or asp; Gly (G) by ala; His (H) by asn, gln, lys, or arg; Ile (I) by val, met, ala, phe, or leu; Leu (L) by val, met, ala, phe, or ile; Lys (K) by gln, asn, or arg; Met (M) by phe, ile, or leu; Phe (F) by leu, val, ile, ala, or tyr; Pro (P) by ala; Ser (S) by thr; Thr (T) by ser; Trp (W) by phe, or tyr; Tyr (Y) by trp, phe, thr, or ser; and Val (V) by ile, leu, met, phe, or ala.

Other considerations for amino acid substitutions include whether or not the residue is located in the interior of a protein or is solvent—(i.e., externally) exposed. For interior residues, conservative substitutions include for example: Asp and Asn; Ser and Thr; Ser and Ala; Thr and Ala; Ala and Gly; Ile and Val; Val and Leu; Leu and Ile; Leu and Met; Phe and Tyr; and Tyr and Trp. For solvent-exposed residues, conservative substitutions include for example: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; and Phe and Tyr.

Percentage sequence identities can be determined with antibody sequences maximally aligned by the Kabat numbering convention. After alignment, if a particular antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" one or more recited elements may include other elements not specifically recited. For example, a composition that comprises antibody may contain the antibody alone or in combination with other ingredients. The phrase "pharmaceutically acceptable salt," refers to pharmaceutically acceptable organic or inorganic salts of an anti-DCLK1 antibody, or binding fragment, or conjugate thereof or agent administered with an anti-DCLK1 antibody. Exemplary salts include sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate, and pamoate (i.e., 1,1' methylene bis-(2 hydroxy 3 naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterions. A chimeric antibody is a molecule in which different portions are derived from different animal species. For example, an antibody may contain a variable region derived from a murine mAb and a human immunoglobulin constant region. Chimeric antibodies can be produced by recombinant DNA techniques, e.g., see Morrison, et al., Proc Natl Acad Sci, 81:6851-6855 (1984). For example, a gene encoding a murine (or other species) monoclonal antibody molecule is digested with restriction enzymes to remove the region encoding the murine Fc, and the equivalent portion of a gene encoding a human Fc constant region is substituted. Chimeric antibodies can also be created by recombinant DNA techniques where DNA encoding murine variable regions can be ligated to DNA encoding the human constant regions, e.g., see International Patent Publication Nos. WO 87/002671 and WO 86/01533, and U.S. Pat. No. 4,816,567.

A chimeric antibody is a recombinant protein that contains the variable domains including the complementarity determining regions (CDRs) of an antibody derived from one species, for example a rodent or rabbit antibody, while the constant domains of the antibody molecule are generally derived from those of a human antibody. For veterinary applications, the constant domains of the chimeric antibody may be derived from that of other species, such as but not limited to, a cat, dog, or horse.

A chimeric antibody can be humanized by replacing the sequences of, for example, a murine framework sequence (FR) in the variable domains of the chimeric antibody with one or more different human FR sequences. Specifically, mouse CDRs are transferred from heavy and light variable chains of the mouse immunoglobulin into the corresponding variable domains of a human antibody. As simply transferring mouse CDRs into human FRs may result in a reduction of antibody affinity, additional modifications might be required in order to restore the original affinity of the murine antibody. This can be accomplished by the replacement of one or more some human residues in the FR regions with their murine counterparts to obtain an antibody with enhanced binding affinity to the DCLK1 epitope (e.g., see Tempest et al., Biotechnology 9:266 (1991) and Verhoeyen et al., Science 239: 1534 (1988)). Techniques for producing humanized antibodies are disclosed, for example, by Jones et al., Nature 321: 522 (1986), Riechmann et al., Nature 332: 323 (1988), Verhoeyen et al., Science 239: 1534 (1988), Carter et al., Proc. Nat'l Acad. Sci. USA 89: 4285 (1992), Sandhu, Crit. Rev. Biotech. 12:437 (1992), and Singer et al., J. Immun. 150: 2844 (1993).

As noted, an antibody light or heavy chain variable region consists of a framework region interrupted by three hypervariable regions, referred to as complementarity determining regions (CDRs). In one embodiment, humanized antibodies are antibody molecules from non-human species having one, two or all CDRs from the non-human species and a framework region from a human immunoglobulin molecule.

A humanized antibody is a genetically engineered antibody in which the variable heavy and variable light CDRs from a non-human "donor" antibody are grafted into human "acceptor" antibody sequences (see for example, U.S. Pat. Nos. 5,530,101; 5,585,089; 5,225,539; 6,407,213; 5,859,205; and 6,881,557). The acceptor antibody sequences can be, for example, a mature human antibody sequence, a composite of such sequences, a consensus sequence of human antibody sequences, or a germline region sequence. Thus, a humanized antibody is an antibody having some or all CDRs entirely or substantially from a non-human donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly, a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain.

As noted, humanized antibodies can be generated by replacing framework sequences of the variable region that are not directly involved in antigen binding with equivalent sequences from human variable regions. Those methods include isolating, manipulating, and expressing the nucleic acid sequences that encode all or part of variable regions from at least one of a heavy or light chain. Sources of such nucleic acid may be obtained from a hybridoma producing an antibody against DCLK1 isoform 2 or 4, for example as described herein. The recombinant DNA encoding the humanized antibody, or fragment thereof, can then be cloned into an appropriate expression vector. An antibody light or heavy chain variable region consists of a framework region interrupted by three hypervariable regions (CDRs). In one embodiment, humanized antibodies are antibody molecules from non-human species having one, two or all CDRs from the non-human species and a framework region from a human immunoglobulin molecule.

Humanized antibodies can be generated by replacing framework sequences of the variable region that are not directly involved in antigen binding with equivalent sequences from human variable regions. Those methods include isolating, manipulating, and expressing the nucleic acid sequences that encode all or part of variable regions from at least one of a heavy or light chain. Sources of such nucleic acid are well known to those skilled in the art and, for example, may be obtained from a hybridoma producing an antibody against DCLK1 isoform 2 or 4, for example as described herein. The recombinant DNA encoding the humanized antibody, or fragment thereof, can then be cloned into an appropriate expression vector.

The humanized antibodies of the present disclosure can be produced by methods known in the art. For example, once non-human (e.g., murine) antibodies are obtained, variable regions can be sequenced, and the location of the CDRs and framework residues determined. Kabat, E. A., et al. (1991) Sequences of Proteins of Immunological Interest, Fifth Edition, U.S. Department of Health and Human Services, NIH Publication No. 91-3242. Chothia, C. et al. (1987) J. Mol. Biol., 196:901-917. The light and heavy chain variable regions can, optionally, be ligated to corresponding constant regions. CDR-grafted antibody molecules can be produced by CDR-grafting or CDR substitution. One, two, or all CDRs of an immunoglobulin chain can be replaced. For example, all of the CDRs of a particular antibody may be from at least a portion of a non-human animal (e.g., mouse such as CDRs shown in herein) or only some of the CDRs may be replaced. It is only necessary to keep the CDRs which are required for specific and high binding affinity of the antibody to DCLK1 isoform 2 or 4.

A fully human antibody can be obtained from a transgenic non-human animal. (See, e.g., Mendez et al., Nature Genetics, 15: 146-156, 1997; U.S. Pat. No. 5,633,425.) Methods for producing fully human antibodies using either combinatorial approaches or transgenic animals transformed with human immunoglobulin loci are known in the art (e.g., Mancini et al., 2004, New Microbiol. 27:315-28; Conrad and Scheller, 2005, Comb. Chem. High Throughput Screen. 8:117-26; Brekke and Loset, 2003, Curr. Opin. Pharmacol. 3:544-50). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

A CDR in a humanized or human antibody is substantially derived from or substantially identical to a corresponding CDR in a non-human antibody when at least 60%, at least 65%, at least 70%, at least 75%, at least 80%, at least 85%, at least 90%, at least 95%, or 100% of corresponding residues (as defined by Kabat) are identical between the respective CDRs. In some embodiments, a CDR in a humanized antibody or human antibody is substantially from or substantially identical to a corresponding CDR in a non-human antibody when there are no more than one, two, or three conservative amino acid substitutions in any given CDR. The variable region framework sequences of an antibody chain or the constant region of an antibody chain are substantially from a human variable region framework sequence or human constant region respectively when at least 60%, at least 65%, at least 70%, at least 75%, at least 80%, at least 85%, at least 90%, at least 95%, or 100% of corresponding residues as defined by Kabat numbering are identical. Although humanized antibodies often incorporate all six CDRs (e.g., as defined by Kabat) from a non-human (e.g., mouse or rabbit) antibody, they can also be made with less than all of the non-human CDRs (e.g., at least 2, 3, 4, or 5).

The humanized antibodies of the present disclosure can be produced by methods known in the art. For example, once non-human (e.g., murine) antibodies are obtained, variable regions can be sequenced, and the location of the CDRs and framework residues determined. Kabat, E. A., et al. (1991) Sequences of Proteins of Immunological Interest, Fifth Edition, U.S. Department of Health and Human Services, NIH Publication No. 91-3242. Chothia, C. et al. (1987) J. Mol. Biol., 196:901-917. The light and heavy chain variable regions can, optionally, be ligated to corresponding constant regions. CDR-grafted antibody molecules can be produced by CDR-grafting or CDR substitution. One, two, or all CDRs of an immunoglobulin chain can be replaced. For example, all of the CDRs of a particular antibody may be from at least a portion of a non-human animal (e.g., mouse such as CDRs shown in herein) or only some of the CDRs may be replaced. It is only necessary to keep the CDRs which are required for specific and high binding affinity of the antibody to DCLK1 isoform 2 or 4.

The present disclosure provides, in certain embodiments, anti-DCLK1 antibodies in which the heavy chain variable region has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable sequence disclosed herein, and the light chain variable region has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable sequence disclosed herein. In some aspects, the antibody is a humanized antibody and there is at least one murine backmutation in the heavy chain variable framework region. In other aspects, the antibody is a humanized antibody and there is at least one murine backmutation in the light chain variable framework region. Additionally, the disclosure provides antibodies in which the humanized heavy chain variable region comprises CDRs having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the CDRs of a heavy chain variable sequence disclosed herein, and the humanized light chain variable region comprises CDRs having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the CDRs of a light chain variable sequence disclosed herein.

Heavy and light chain variable regions of humanized antibodies can be linked to at least a portion of a human constant region, for example, for human antibody isotypes IgG1, IgG2, IgG3, or IgG4. Light chain constant regions can be lambda or kappa. Antibodies can be expressed as tetramers containing two light and two heavy chains, as separate heavy chains, light chains, as Fab, Fab', F(ab')$_2$, and Fv, or as single chain antibodies in which heavy and light chain variable domains are linked through a spacer. All antibody isotypes are encompassed by the present disclosure, including IgG (e.g., IgG1, IgG2, IgG3, IgG4), IgM, IgA (IgA1, IgA2), IgD or IgE. The antibodies or antigen-binding portions thereof may be mammalian (e.g., mouse, rabbit, human) antibodies or antigen-binding portions thereof.

Humanized or chimeric antibodies are typically produced by recombinant expression. Recombinant polynucleotide constructs typically include an expression control sequence operably linked to the coding sequences of antibody chains, including naturally-associated or heterologous promoter regions. The expression control sequences may be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

Mammalian cells may be used as hosts for expressing nucleotide segments encoding immunoglobulins or fragments thereof (e.g., see Winnacker, From Genes to Clones, (VCH Publishers, N Y, 1987). A number of suitable host cell lines capable of secreting intact heterologous proteins have been developed in the art, and include CHO cell lines (e.g., DG44), various COS cell lines, HeLa cells, HEK293 cells, L cells, and non-antibody-producing myelomas including Sp2/0 and NS0. In certain particular (but non-limiting) embodiments, the cells are nonhuman. Expression vectors for these cells can include expression control sequences, such as an origin of replication, a promoter, an enhancer (e.g., Queen et al., Immunol. Rev. 89:49 (1986)), and necessary processing information sites, such as ribosome binding sites, RNA splice sites, polyadenylation sites, and transcriptional terminator sequences. Examples of expression control sequences include, but are not limited to, promoters derived from endogenous genes, cytomegalovirus, SV40, adenovirus, or bovine papillomavirus (e.g., see Co et al., J. Immunol. 148:1149 (1992)).

Human antibodies against DCLK1 protein can be provided by a variety of techniques described below. Once expressed, antibodies can be purified according to standard procedures of the art, including but not limited to HPLC purification, column chromatography, and gel electrophoresis. Methods for producing human antibodies include, but are not limited to, those shown in U.S. Pat. Nos. 4,634,664; 4,634,666; 5,877,397; 5,874,299; 5,814,318; 5,789,650; 5,770,429; 5,661,016; 5,633,425; 5,625,126; 5,569,825; 5,545,806; 5,877,218; 5,871,907; 5,858,657; 5,837,242; 5,733,743; and 5,565,332; and published PCT applications WO 91/17271; WO 92/01047; and WO93/12227.

The present disclosure also encompasses a nucleic acid encoding the present antibody or antigen-binding portions thereof that specifically bind to DCLK1 protein. The nucleic acid may be expressed in a cell to produce the presently disclosed antibody or antigen-binding portion thereof. The isolated nucleic acid of the present disclosure comprises, for example, a sequence encoding a peptide that is at least about 70%, at least about 75%, at least about 80%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% homologous to SEQ ID NOs: 3-12, 14, 16-22, 24, and 26-32.

A nucleic acid encoding the present antibody or antigen-binding portion thereof may be introduced into an expression vector that can be expressed in a suitable expression system, followed by isolation or purification of the expressed antibody or antigen-binding portion thereof. Optionally, a nucleic acid encoding the present antibody or antigen-binding portion thereof can be translated in a cell-free translation system, e.g., see U.S. Pat. No. 4,816,567.

Anti-DCLK1 antibodies or antigen binding portions thereof can be produced by host cells transformed with DNA encoding light and heavy chains (or CDR portions thereof) of a desired antibody. Antibodies can be isolated and purified from these culture supernatants and/or cells using standard techniques. For example, a host cell may be transformed with DNA encoding the light chain, the heavy chain, or both, of an antibody. Recombinant DNA technology may also be used to remove some or all of the DNA encoding either or both of the light and heavy chains that is not necessary for binding, e.g., the constant region.

The present nucleic acids can be expressed in various suitable cells, including prokaryotic and eukaryotic cells, e.g., bacterial cells, (e.g., E. coli), yeast cells, plant cells, insect cells, and mammalian cells. A number of mammalian cell lines are known in the art and include immortalized cell lines available from the American Type Culture Collection (ATCC). Non-limiting examples of the cells include all cell lines of mammalian origin or mammalian-like characteristics, including but not limited to, parental cells, derivatives and/or engineered variants of monkey kidney cells (COS, e.g., COS-1, COS-7), HEK293, baby hamster kidney (BHK, e.g., BHK21), Chinese hamster ovary (CHO), NS0, PerC6, BSC-1, human hepatocellular carcinoma cells (e.g., Hep G2), SP2/0, HeLa, Madin-Darby bovine kidney (MDBK), myeloma and lymphoma cells. The engineered variants include, e.g., glycan profile modified and/or site-specific integration site derivatives.

The present disclosure also provides for cells comprising the nucleic acids described herein. The cells may be a hybridoma or transfectant. Examples of the types of the cells are discussed above.

Various techniques, such as production of chimeric or humanized antibodies, may involve procedures of antibody cloning and construction. The antigen-binding $V_L$ (variable light chain) and $V_H$ (variable heavy chain) sequences for an antibody of interest may be obtained by a variety of molecular cloning procedures, such as RT-PCR, 5'-RACE, and cDNA library screening. The $V_L$ and $V_H$ genes of an antibody from a cell that expresses a murine antibody can be cloned by PCR amplification and sequenced. To confirm their authenticity, the cloned $V_L$ and $V_H$ genes can be expressed in cell culture as a chimeric antibody, for example as described by Orlandi et al., (Proc. Natl. Acad. Sci., USA, 86: 3833 (1989)). Based on the $V_L$ and $V_H$ gene sequences, a humanized antibody can then be designed and constructed as described by Leung et al. (Mol. Immunol., 32: 1413 (1995)).

The present disclosure further provides nucleic acids encoding any of the humanized heavy and light chains described herein. Typically, the nucleic acids also encode a signal peptide fused to the mature heavy and light chains. Coding sequences on nucleic acids can be in operable linkage with regulatory sequences to ensure expression of the coding sequences, such as a promoter, enhancer, ribosome binding site, transcription termination signal and the like. The present disclosure in further embodiments includes vectors which comprise the nucleic acids encoding heavy and light chains, and hosts cells which have been transfected with such vectors. The nucleic acids can be synthesized by for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

In one embodiment, this disclosure provides an isolated polynucleotide encoding an antibody heavy chain variable region comprising the amino acid sequence of SEQ ID NO:14 or SEQ ID NO:24. This isolated polynucleotide can further encode a human IgG heavy chain constant region (e.g., IgG1, IgG2, IgG3, or IgG4). In one embodiment, the amino acid sequence of the IgG constant region comprises one or more substitutions. The disclosure also provides an expression vector comprising said polynucleotide encoding the antibody heavy chain variable region comprising the amino acid sequence of SEQ ID NO:14 or SEQ ID NO:24, and further, a host cell comprising that expression vector. In some embodiments, the host cell is a mammalian host cell, e.g., a CHO cell.

In another embodiment, this disclosure provides an isolated polynucleotide encoding an antibody light chain variable region comprising the amino acid sequence of SEQ ID NO:16 or SEQ ID NO:26. This isolated polynucleotide can further encode a human IgG light chain constant region, e.g., a kappa constant region. The amino acid sequence of the kappa constant region may comprise one or more substitutions. The disclosure also provides an expression vector comprising said polynucleotide encoding the antibody light chain variable region comprising the amino acid sequence of SEQ ID NO:16 or SEQ ID NO:26, and further, a host cell comprising that expression vector. In some embodiments, the host cell is a mammalian host cell, e.g., a CHO cell.

In one embodiment, this disclosure provides an isolated heavy chain polynucleotide encoding an antibody heavy chain variable region comprising the amino acid sequence of SEQ ID NO:14 or SEQ ID NO:24, and an isolated light chain polynucleotide encoding an antibody light chain variable region comprising the amino acid sequence of SEQ ID NO:16 or SEQ ID NO:26. The heavy chain polynucleotide can further encode a human IgG heavy chain constant region (e.g., IgG1, IgG2, IgG3, or IgG4). In one embodiment, the amino acid sequence of the IgG constant region comprises one or more substitutions. The light chain polynucleotide can further encode a human IgG light chain constant region, e.g., a kappa constant region. The amino acid sequence of the IgG constant region may comprise one or more substitutions. The amino acid sequence of the kappa constant region may comprise one or more substitutions. The disclosure also provides an expression vector comprising said polynucleotide encoding the antibody heavy chain variable region comprising the amino acid sequence of SEQ ID NO:14 or SEQ ID NO:24, and the antibody light chain variable region comprising the amino acid sequence of SEQ ID NO:16 or SEQ ID NO:26. The disclosure also provides a host cell comprising the expression vector. In some embodiments, the host cell is a mammalian host cell, e.g., a CHO cell.

In one embodiment, this disclosure provides an isolated polynucleotide encoding an antibody heavy chain variable region comprising the amino acid sequences of one or more of SEQ ID NOS:17, 18, and 19, or one or more of SEQ ID NOS:27, 28, and 29. This isolated polynucleotide can further encode a human IgG heavy chain constant region (e.g., IgG1, IgG2, IgG3, or IgG4). In one embodiment, the amino acid sequence of the IgG constant region comprises one or more substitutions. The disclosure also provides an expression vector comprising the polynucleotide encoding said heavy chain variable region, and further, a host cell comprising that expression vector. In some embodiments, the host cell is a mammalian host cell, e.g., a CHO cell.

In another embodiment, this disclosure provides an isolated polynucleotide encoding an antibody light chain variable region comprising the amino acid sequence of one or more of SEQ ID NO:20, 21, and 22, or one or more of SEQ ID NO:30, 31, and 32. This isolated polynucleotide can further encode a human IgG light chain constant region, e.g., a kappa constant region. The amino acid sequence of the kappa constant region may comprise one or more substitutions. The disclosure also provides an expression vector comprising the polynucleotide encoding said light chain variable region, and further, a host cell comprising that expression vector. In some embodiments, the host cell is a mammalian host cell, e.g., a CHO cell.

In one embodiment, this disclosure provides an isolated heavy chain polynucleotide encoding an antibody heavy chain variable region comprising one or more of SEQ ID NOS:17, 18, and 19, and an isolated light chain polynucleotide encoding an antibody light chain variable region comprising one or more of SEQ ID NOS:20, 21, and 22. The heavy chain polynucleotide can further encode a human IgG heavy chain constant region (e.g., IgG1, IgG2, IgG3, or IgG4). In one embodiment, the amino acid sequence of the IgG constant region comprises one or more substitutions. The light chain polynucleotide can further encode a human IgG light chain constant region, e.g., a kappa constant region. The amino acid sequence of the IgG constant region may comprise one or more substitutions. The amino acid sequence of the kappa constant region may comprise one or more substitutions. The disclosure also provides an expression vector comprising said polynucleotide encoding the heavy chain variable region comprising one or more of SEQ ID NOS:17, 18, and 19, and an isolated light chain polynucleotide encoding an antibody light chain variable region comprising one or more of SEQ ID NOS:20, 21, and 22. The disclosure also provides a host cell comprising the expression vector. In some embodiments, the host cell is a mammalian host cell, e.g., a CHO cell.

In one embodiment, this disclosure provides an isolated heavy chain polynucleotide encoding an antibody heavy chain variable region comprising one or more of SEQ ID NOS:27, 28, and 29, and an isolated light chain polynucleotide encoding an antibody light chain variable region comprising one or more of SEQ ID NOS:30, 31, and 32. The heavy chain polynucleotide can further encode a human IgG heavy chain constant region (e.g., IgG1, IgG2, IgG3, or IgG4). In one embodiment, the amino acid sequence of the IgG constant region comprises one or more substitutions. The light chain polynucleotide can further encode a human IgG light chain constant region, e.g., a kappa constant region. The amino acid sequence of the IgG constant region may comprise one or more substitutions. The amino acid sequence of the kappa constant region may comprise one or more substitutions. The disclosure also provides an expression vector comprising said polynucleotide encoding the heavy chain variable region comprising one or more of SEQ ID NOS:27, 28, and 29, and an isolated light chain polynucleotide encoding an antibody light chain variable region comprising one or more of SEQ ID NOS:30, 31, and 32. The disclosure also provides a host cell comprising the expression vector. In some embodiments, the host cell is a mammalian host cell, e.g., a CHO cell.

In certain embodiments, the present antibody or antigen-binding portion thereof can be synthesized by solid phase procedures well known in the art (such as, but not limited to, processes disclosed in Solid Phase Peptide Synthesis: A Practical Approach by E. Atherton and R. C. Sheppard, published by IRL at Oxford University Press (1989); Methods in Molecular Biology, Vol. 35: Peptide Synthesis Protocols (ed. M. W. Pennington and B. M. Dunn), chapter 7. Solid Phase Peptide Synthesis, 2nd Ed., Pierce Chemical Co., Rockford, Ill. (1984); G. Barany and R. B. Merrifield, The Peptides: Analysis, Synthesis, Biology, editors E. Gross and J. Meienhofer, Vol. 1 and Vol. 2, Academic Press, New York, (1980), pp. 3-254; and M. Bodansky, Principles of Peptide Synthesis, Springer-Verlag, Berlin (1984)).

The present disclosure provides for methods for making an antibody or antigen-binding portion thereof that specifically binds to DCLK1 isoform 2 or 4. For example, a non-human animal is immunized with a composition that includes a portion of DCLK1 isoform 2 or 4 (e.g., SEQ ID NOS:3-12), and then a specific antibody is isolated from the animal. The method can further include evaluating binding of the antibody to the antigenic portion of DCLK1 isoform 2 or 4.

Antibody fragments which recognize specific epitopes can be generated by known techniques. The antibody fragments are antigen binding portions of an antibody, such as $F(ab)_2$, Fab', Fab, Fv, scFv, and other fragments described herein. Other antibody fragments include, but are not limited to: the F(ab')2 fragments which can be produced by pepsin digestion of the antibody molecule and the Fab' fragments, which can be generated by reducing disulfide bridges of the F(ab')2 fragments. Alternatively, Fab' expression libraries can be constructed to allow rapid and easy identification of monoclonal Fab' fragments with the desired specificity. In certain embodiments, the antibody fragment may be a fragment that is not an scFv fragment.

A single chain Fv molecule (scFv) comprises a VL domain and a VH domain. The VL and VH domains associate to form a target binding site. These two domains are further covalently linked by a peptide linker (L). Methods for making scFv molecules and designing suitable peptide linkers are disclosed in U.S. Pat. Nos. 4,704,692 and 4,946,778, for example. An antibody fragment can be prepared by known methods, for example, as disclosed by U.S. Pat. Nos. 4,036,945 and 4,331,647.

A CDR is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest.

Another form of an antibody fragment is a single-domain antibody (dAb), sometimes referred to as a single chain antibody. Techniques for producing single-domain antibodies are well known in the art (see, e.g., Cossins et al., Protein Expression and Purification, 2007, 51:253-59; Shuntao et al., Molec. Immunol 2006, 43:1912-19; Tanha et al., J. Biol. Chem. 2001, 276:24774-780).

In certain embodiments, the sequences of antibodies, such as the Fc portions of antibodies, may be varied to optimize the physiological characteristics of the conjugates, such as the half-life in serum. Methods of substituting amino acid sequences in proteins are widely known in the art, such as by site-directed mutagenesis (e.g. Sambrook et al., Molecular Cloning, A laboratory manual, 2ndEd, 1989). In certain embodiments, the variation may involve the addition or removal of one or more glycosylation sites in the Fc sequence (see e.g., U.S. Pat. No. 6,254,868).

The presently disclosed antibodies or antigen-binding fragments thereof have specific binding $K_D$ to DCLK1 isoform 2 or 4 of less than $10^{-6}$ M, less than $10^{-7}$ M, less than $10^{-8}$ M, less than $10^{-9}$M, less than $10^{-10}$ M, less than $10^{-11}$M, or less than $10^{-12}$M. Specific binding is detectably higher in magnitude and distinguishable from non-specific binding occurring to at least one unrelated target. The presently disclosed antibodies or antigen-binding fragments thereof have specific binding $K_D$ to an epitope comprising SEQ ID NO:10 of less than $10^{-6}$ M, less than $10^{-7}$ M, less than $10^{-8}$ M, less than $10^{-9}$ M, less than $10^{-10}$ M, less than $10^{-11}$M, or less than $10^{-12}$ M.

The presently disclosed anti-DCLK1 antibodies and binding fragments thereof can be derivatized or linked to, e.g., conjugated to, therapeutic agents and/or diagnostic agents to form antibody-drug conjugates (ADCs). For example, an antibody can be functionally linked, directly or indirectly, by covalent bonding or by noncovalent interactions to one or more other molecular entities, such as another antibody, antibody fragment, a detectable agent, a cytotoxic agent, a pharmaceutical agent, a protein or peptide that can mediate association with another molecule (such as a streptavidin core region or a polyhistidine tag), amino acid linkers, spacers, bridges, signal sequences, immunogenic carriers, or ligands useful in protein purification, such as glutathione-S-transferase, histidine tag, and staphylococcal protein A. Useful detectable agents with which a protein can be derivatized (or labeled) include fluorescent compounds, various enzymes, prosthetic groups, luminescent materials, bioluminescent materials, and radioactive materials. Non-limiting, exemplary fluorescent detectable agents include fluorescein, fluorescein isothiocyanate, rhodamine, and, phycoerythrin. A protein or antibody can also be derivatized with detectable enzymes, such as alkaline phosphatase, horseradish peroxidase, beta-galactosidase, acetylcholinesterase, glucose oxidase and the like. A protein can also be derivatized with a prosthetic group (e.g., streptavidin/biotin and avidin/biotin).

Particularly suitable moieties for conjugation to antibodies are cytotoxic agents (e.g., chemotherapeutic agents), prodrug converting enzymes, radionuclides such as radioactive isotopes or compounds, an immunomodulator, an anti-angiogenic agent, a pro-apoptotic agent, a cytokine, a chemokine, a drug, a hormone, an siRNA, an enzyme, a growth factor, a prodrug, an oligonucleotide, a pro-apoptotic agent, an interference RNA, a photoactive therapeutic agent, a tyrosine kinase inhibitor, a Bruton kinase inhibitor, a sphingosine inhibitor, a cytotoxic agent or toxins (these moieties being collectively referred to as therapeutic agents or drugs). For example, an anti-DCLK1 antibody can be conjugated to a cytotoxic agent such as a chemotherapeutic agent, or a toxin (e.g., a cytostatic or cytocidal agent such as, e.g., abrin, ricin A, *pseudomonas* exotoxin, or diphtheria toxin). Examples of useful classes of cytotoxic agents include, for example, DNA minor groove binders, DNA alkylating agents, and tubulin inhibitors. Exemplary cytotoxic agents include, for example, auristatins, camptothecins, duocarmycins, etoposides, maytansines and maytansinoids (e.g., DM1 and DM4), taxanes, benzodiazepines (e.g., pyrrolo[1,4]benzodiazepines (PBDs), indolinobenzodiazepines, and oxazolidinobenzodiazepines) and vinca alkaloids. Techniques for conjugating therapeutic agents to proteins, and in particular to antibodies, are well-known (e.g., see, Carter, P J and Senter P D, Antibody-Drug Conjugates for Cancer Therapy. Cancer J., 2008, 14(3):154-169).

Examples of toxins include but are not limited to ricin, abrin, alpha toxin, saporin, ribonuclease (RNase), DNase I, Staphylococcal enterotoxin-A, pokeweed antiviral protein, gelonin, diphtheria toxin, *Pseudomonas* exotoxin, and *Pseudomonas* endotoxin.

Examples of radionuclides include but are not limited to $^{111}$In, $^{111}$At, $^{177}$Lu, $^{211}$Bi, $^{212}$Bi, $^{213}$Bi, $^{211}$At, $^{62}$Cu, $^{67}$Cu, $^{90}$Y, $^{125}$I, $^{131}$I, $^{133}$I, $^{32}$P, $^{33}$P, $^{47}$Sc, $^{111}$Ag, $^{67}$Ga, $^{153}$Sm, $^{161}$Tb, $^{152}$Dy, $^{166}$Dy, $^{161}$Ho, $^{166}$Ho, $^{186}$Re, $^{188}$Re, $^{189}$Re, $^{211}$Pb, $^{212}$Pb, $^{223}$Ra, $^{225}$Ac, $^{227}$Th, $^{77}$As, $^{89}$Sr, $^{99}$Mo, $^{105}$Rh, $^{149}$Pm, $^{169}$Er, $^{194}$Ir, $^{58}$Co, $^{80m}$Br, $^{99m}$Tc, $^{103m}$Rh, $^{109}$Pt, $^{119}$Sb, $^{125}$I, $^{189m}$Os, $^{192}$Ir, $^{219}$Rn, $^{215}$Po, $^{221}$Fr, $^{255}$Fm, $^{11}$C, $^{13}$N, $^{15}$O, $^{75}$Br, $^{198}$Au, $^{199}$Au, $^{224}$Ac, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{227}$Th, $^{125m}$Te, $^{165}$Tm, $^{167}$Tm, $^{168}$Tm, $^{197}$Pt, $^{109}$Pd, $^{142}$Pr, $^{143}$Pr, $^{161}$Tb, $^{57}$Co, $^{58}$Co, $^{51}$Cr, $^{59}$Fe, $^{75}$Se, $^{201}$Tl, $^{76}$Br, and $^{169}$Yb.

Examples of diagnostic agents include but are not limited to radionuclide, a contrast agent, a fluorescent agent, a chemiluminescent agent, a bioluminescent agent, a paramagnetic ion, an enzyme, and a photoactive diagnostic agent.

Examples of diagnostic radionuclides include but are not limited to $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$F, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, or other gamma-, beta-, or positron-emitters.

Examples of paramagnetic ions include, but are not limited to, chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III).

Examples of fluorescent labeling diagnostic agents include, but are not limited to, fluorescein isothiocyanate, rhodamine, phycoerytherin, phycocyanin, allophycocyanin, o-phthaldehyde and fluorescamine, or a chemiluminescent labeling compound selected from the group comprising luminol, isoluminol, an aromatic acridinium ester, an imidazole, an acridinium salt and an oxalate ester, or a bioluminescent compound selected from the group comprising luciferin, luciferase and aequorin.

As noted, in certain embodiments, the antibodies or fragments thereof may be used in combination with one or more therapeutic and/or diagnostic agents. Where the agent is attached to an antibody or fragment thereof to be administered by subcutaneous, intramuscular or transdermal administration, then only non-cytotoxic agents are contemplated. Non-cytotoxic agents may include, without limitation, immunomodulators, cytokines (and their inhibitors), chemokines (and their inhibitors), tyrosine kinase inhibitors, growth factors, hormones and certain enzymes (i.e., those that do not induce local necrosis), or their inhibitors. Where the agent is co-administered either before, simultaneously with or after the subcutaneous, intramuscular or transdermal antibody formulation, then cytotoxic agents may be utilized. An agent may be administered as an immunoconjugate with a second antibody or fragment thereof, or may be administered as a free agent. The following discussion applies to both cytotoxic and non-cytotoxic agents.

Examples of therapeutic agents that can be conjugated (or delivered separately) include, but are not limited to, 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celecoxib, chlorambucil, cisplatinum, Cox-2 inhibitors, CPT-11 SN-38, carboplatin, cladribine, camptothecans, cyclophosphamide, cytarabine, dacarbazine, docetaxel, dactinomycin, daunorubicin, doxorubicin, 2-pyrrolinodoxorubicine (2P-DOX), pro-2P-DOX, cyano-morpholino doxorubicin, doxorubicin glucuronide, epirubicin glucuronide, estramustine, epipodophyllotoxin, estrogen receptor binding agents, etoposide (VP16), etoposide glucuronide, etoposide phosphate, floxuridine (FUdR), 3',5'-O-dioleoyl-FudR (FUdR-dO), fludarabine, flutamide, farnesyl-protein transferase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosourea, plicomycin, procarbazine, paclitaxel, pentostatin, PSI-341, raloxifene, semustine, streptozocin, tamoxifen, paclitaxel, temazolomide, transplatinum, thalidomide, thioguanine, thiotepa, teniposide, topotecan, uracil mustard, vinorelbine, vinblastine, vincristine, a vinca alkaloid, a tyrophostin, canertinib, dasatinib, erlotinib, gefitinib, imatinib, lapatinib, leflunomide, nilotinib, pazopanib, semaxinib, sorafenib, sunitinib, sutent, vatalanib, PCI-32765 (ibrutinib), PCI-45292, GDC-0834, LFM-A13, and RN486.

Examples of toxins include but are not limited to ricin, abrin, alpha toxin, saporin, ribonuclease (RNase), e.g., onconase, DNase I, Staphylococcal enterotoxin-A, pokeweed antiviral protein, gelonin, diphtheria toxin, *Pseudomonas* exotoxin, and *Pseudomonas* endotoxin.

Immunomodulators include, but are not limited to, cytokines, stem cell growth factors, lymphotoxins, hematopoietic factors, colony stimulating factors (CSF), interferons (IFN), erythropoietins, thrombopoietins, and combinations thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons-alpha, -beta, -lamda or -gamma, and stem cell growth factor, such as that designated "S1 factor." Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-bet.; insulin-like growth factor-I and -II; erythropoietin (EPO); osteoinductive factors; interferons such as interferon-alpha, -beta, -lamda and -gamma; colony stimulating factors (CSFs) such as macrophage-CSF (M-CSF); interleukins (ILs) such as IL-1, IL-1alpha., IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-23, IL-25, LIF, kit-ligand or FLT-3, angiostatin, thrombospondin, endostatin, tumor necrosis factor, and lymphotoxin. Chemokines of use include RANTES, MCAF, MIP1-alpha, MIP1-Beta and IP-10.

In certain non-limiting embodiments, therapeutic radionuclides have a decay-energy in the range of 20 to 6,000 keV, such as in the ranges 60 to 200 keV for an Auger emitter, 100-2,500 keV for a beta emitter, and 4,000-6,000 keV for an alpha emitter. Maximum decay energies of useful beta-particle-emitting nuclides may be, but are not limited to, 20-5,000 keV, 100-4,000 keV, or 500-2,500 keV. Also included are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides may be <1,000 keV, <100 keV, or <70 keV. Also included are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213, Th-227 and Fm-255. Decay energies of useful alpha-particle-emitting radionuclides include 2,000-10,000 keV, 3,000-8,000 keV, or 4,000-7,000 keV.

In certain embodiments, the therapeutic agent (e.g., cytotoxic agent) can be conjugated to the antibody as a prodrug in a manner that reduces its activity unless it is detached/cleaved from the antibody (e.g., by hydrolysis, by antibody degradation, or by a cleaving agent). Such a therapeutic agent can be attached to the antibody via a linker such as a cleavable linker. In one embodiment, the cleavable linker is sensitive to cleavage in the intracellular environment of the DCLK1-expressing cancer cell but is not substantially sensitive to the extracellular environment, such that the conjugate is cleaved from the antibody when it is internalized by the DCLK1-expressing cancer cell (e.g., in the endosomal or, for example by virtue of pH sensitivity or protease sensitivity, in the lysosomal environment or in the caveolear environment). The therapeutic agent can also be attached to the antibody with a non-cleavable linker. As indicated, the linker may comprise a cleavable unit. In some such embodiments, the structure and/or sequence of the cleavable unit is selected such that it is cleaved by the action of enzymes present at the target site (e.g., the target cell). In other embodiments, cleavable units that are cleavable by changes in pH (e.g. acid or base labile), temperature or upon irradiation (e.g. photolabile) may also be used.

In some embodiments, the cleavable unit may comprise one amino acid or a contiguous sequence of amino acids. The amino acid sequence may be the target substrate for an enzyme. In some aspects, the cleavable unit is a peptidyl unit and is at least two amino acids long. Cleaving agents can include cathepsins B and D and plasmin (see, e.g., Dubowchik and Walker, 1999, Pharm. Therapeutics 83:67-123). Most typical are cleavable unit that are cleavable by enzymes that are present in DCLK1 expressing cells, i.e., an enzyme cleavable linker. Accordingly, the linker can be cleaved by an intracellular peptidase or protease enzyme, including a lysosomal or endosomal protease. For example, a linker that is cleavable by the thiol-dependent protease cathepsin-B, which is highly expressed in cancerous tissue, can be used (e.g., a linker comprising a Phe-Leu or a Val-Citrulline peptide or a Val-Ala peptide).

In some embodiments, the linker will comprise a cleavable unit is conjugated to the therapeutic agent via an additional functional unit, e.g., a self-immolative spacer unit or a non-self-immolative spacer unit. Anon self-immolative spacer unit is one in which part or all of the spacer unit remains bound to the drug unit after cleavage of a cleavable unit (e.g., amino acid) from the antibody drug conjugate. To liberate the drug, an independent hydrolysis reaction takes place within the target cell to cleave the spacer unit from the drug. With a self-immolative spacer unit, the drug is released without the need for drug for a separate hydrolysis step. In one embodiment, wherein the linker comprises a cleavable unit and a self immolative group, the cleavable unit is cleavable by the action of an enzyme and after cleavage of the cleavable unit, the self-immolative group(s) release the therapeutic agent. In some embodiments, the cleavable unit of the linker will be directly or indirectly conjugated to the therapeutic agent on one end and on the other end will be directly or indirectly conjugated to the antibody. In some such embodiments, the cleavable unit will be directly or indirectly (e.g., via a self-immolative or non-self-immolative spacer unit) conjugated to the therapeutic agent on one end and on the other end will be conjugated to the antibody via a stretcher unit. A stretcher unit links the antibody to the rest of the drug and/or drug linker. In one embodiment, the connection between the antibody and the rest of the drug or drug linker is via a maleimide group, e.g., via a maleimidocaproyl linker. In some embodiments, the antibody will be linked to the drug via a disulfide, for example the disulfide linked maytansinoid conjugates SPDB-DM4 and SPP-DM1.

The connection between the antibody and the linker can be via a number of different routes, e.g., through a thioether bond, through a disulfide bond, through an amide bond, or through an ester bond. In one embodiment, the connection between the anti-DCLK1 antibody and the linker is formed between a thiol group of a cysteine residue of the antibody and a maleimide group of the linker. In some embodiments, the interchain bonds of the antibody are converted to free thiol groups prior to reaction with the functional group of the linker. In some embodiments, a cysteine residue is an introduced into the heavy or light chain of an antibody and reacted with the linker. Positions for cysteine insertion by substitution in antibody heavy or light chains include those described in U.S. Patent Application Publication No. US 2007/0092940 and International Patent Application Publication No. WO 2008/070593.

In some embodiments, the antibody-drug conjugates have the formula: Mab-(LU-D)$_n$, wherein Mab is an anti-DCLK1 antibody, LU is a Linker unit and D is a Drug unit (i.e., the therapeutic or diagnostic agent). The subscript n ranges for example from 1 to 20 (i.e., 1, 2, 3, 4, 5, 6, 7, 8, 9, 10, 11, 12, 13, 14, 15, 16, 17, 18, 19, or 20), or more. Such conjugates comprise an anti-DCLK1 antibody covalently linked to at least one drug via a linker. The LU is connected at one end to the antibody and at the other end to a drug molecule. The skilled artisan will appreciate that in some aspects, the subscript n represents the number of drug-linkers on a singular antibody. In other aspects, n represents the average number of drug-linker molecules per antibody, e.g., the average number of drug-linkers per antibody in a reaction mixture or composition (e.g., pharmaceutical composition), and can be an integer or non-integer value. Accordingly, in some aspects, for compositions (e.g., pharmaceutical compositions), n represents the average drug loading of the antibody-drug conjugates in the composition, and n ranges from 1 to 20. In some embodiments, the present disclosure provides antibody-linker conjugates have the formula: Mab-(LU)$_n$ wherein Mab is an anti-DCLK1 antibody, and LU is a Linker unit for linking a drug to the antibody The subscript n ranges for example from 1 to 20 (i.e., 1, 2, 3, 4, 5, 6, 7, 8, 9, 10, 11, 12, 13, 14, 15, 16, 17, 18, 19, or 20), or more. Such conjugates comprise an anti-DCLK1 antibody covalently linked to one or more linkers, wherein the Linker Unit is connected at one end to the antibody and has a free end for connecting to a drug molecule. In some embodiments, n is from about 1 to about 18 drugs per antibody. In some embodiments, n is 1. In some embodiments, n is 2. In some embodiments, n is from about 2 to about 12 drugs per antibody. In some embodiments, n is from about 2 to about 10, about 2 to about 8, about 2 to 6, about 2 to 5, about 2 to 4, or about 2 to 3 per antibody.

In certain embodiments, a therapeutic and/or diagnostic agent may be covalently attached to an antibody or antibody fragment to form an immunoconjugate. In some embodiments, the therapeutic and/or diagnostic agent may be attached to an antibody or fragment thereof via a carrier moiety. Carrier moieties may be attached, for example to reduced SH groups and/or to carbohydrate side chains. A carrier moiety can be attached at the hinge region of a reduced antibody component via disulfide bond formation. Alternatively, such agents can be attached using a heterobifunctional cross-linker, such as N-succinyl 3-(2-pyridyldithio)propionate (e.g., see Yu et al., Int. J. Cancer 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc., 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the carrier moiety can be conjugated via a carbohydrate moiety in the Fc region of the antibody.

Methods for conjugating functional groups to antibodies via an antibody carbohydrate moiety are well-known to those of skill in the art. See, for example, Shih et al., Int. J. Cancer 41: 832 (1988); Shih et al., Int. J. Cancer 46: 1101 (1990); and U.S. Pat. No. 5,057,313. The general method involves reacting an antibody having an oxidized carbohydrate portion with a carrier polymer that has at least one free amine function. This reaction results in an initial Schiff base (imine) linkage, which can be stabilized by reduction to a secondary amine to form the final conjugate.

Other methods of chemical conjugation of such moieties to biomolecules are well known in the art, and any such known method may be utilized to form an antibody conjugate that functions in accordance with the present disclosure. Such methods of immunoconjugate formation are disclosed, for example, in U.S. Pat. Nos. 4,699,784; 4,824,659; 5,525,338; 5,677,427; 5,697,902; 5,716,595; 6,071,490; 6,187,284; 6,306,393; 6,548,275; 6,653,104; 6,962,702; 7,033,572; 7,147,856; and 7,259,240.

Exemplary antibody-drug conjugates include auristatin based antibody-drug conjugates, i.e., conjugates wherein the therapeutic agent component is an auristatin-type drug. Auristatins bind tubulin, have been shown to interfere with microtubule dynamics and nuclear and cellular division, and have anticancer activity. Typically, the auristatin based antibody-drug conjugate comprises a linker between the auristatin drug and the anti-DCLK1 antibody. The auristatins can be linked to the anti-DCLK1 antibody at any position suitable for conjugation to a linker. As noted, the linker can be, for example, a cleavable linker (e.g., a peptidyl linker) or anon-cleavable linker (e.g., linker released by degradation of the antibody). The auristatin can be auristatin E or a derivative thereof. The auristatin can be, for example, an ester formed between auristatin E and a keto acid. For example, auristatin E can be reacted with paraacetyl benzoic acid or benzoylvaleric acid to produce AEB and AEVB, respectively. Other typical auristatins include MMAF (monomethyl auristatin F), and MMAE (monomethyl auristatin E). The synthesis and structure of exemplary auristatins are described in U.S. Pat. Nos. 7,659,241; 7,498,298; and 7,968,687, and U.S. Published Patent Application Nos. 20090111756, and 20090018086.

The present antibodies or antigen-binding portions thereof can be formulated into compositions for delivery to a mammalian subject. The composition can be administered alone, and/or mixed with a pharmaceutically acceptable vehicle or excipient. Suitable vehicles are, for example, water, saline, dextrose, glycerol, ethanol, or the like, and combinations thereof. In addition, the vehicle can contain minor amounts of auxiliary substances such as wetting or emulsifying agents, pH buffering agents, or adjuvants. The compositions of the present disclosure can also include ancillary substances, such as pharmacological agents, cytokines, or other biological response modifiers.

Furthermore, the compositions can be formulated into compositions in either neutral or salt forms. Pharmaceutically acceptable salts include the acid addition salts (formed with the free amino groups of the active polypeptides) and which are formed with inorganic acids such as, for example, hydrochloric or phosphoric acids, or organic acids such as acetic, oxalic, tartaric, mandelic, and the like. Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, and procaine.

Compositions can be administered in a single dose treatment or in multiple dose treatments on a schedule and over a time period appropriate to the age, weight and condition of the subject, the particular composition used, and the route of administration. In one embodiment, a single dose of the composition according to the disclosure is administered. In other embodiments, multiple doses are administered. The frequency of administration can vary depending on any of a variety of factors, e.g., severity of the symptoms, degree of immunoprotection desired, or whether the composition is used for prophylactic or curative purposes. For example, in certain embodiments, the composition is administered once per month, twice per month, three times per month, every other week, once per week, twice per week, three times per week, four times per week, five times per week, six times per week, every other day, daily, twice a day, or three times a day. The duration of treatment, e.g., the period of time over which the composition is administered, can vary, depending on any of a variety of factors, e.g., subject response. For example, the composition can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

The compositions can be combined with a pharmaceutically acceptable carrier (excipient) to form a pharmacological composition. Pharmaceutically acceptable carriers can contain a physiologically acceptable compound that acts to, e.g., stabilize, or increase or decrease the absorption or clearance rates of the pharmaceutical compositions. Physiologically acceptable compounds can include, e.g., carbohydrates, such as glucose, sucrose, or dextrans, antioxidants, such as ascorbic acid or glutathione, chelating agents, low molecular weight proteins, detergents, liposomal carriers, or excipients or other stabilizers and/or buffers. Other physiologically acceptable compounds include wetting agents, emulsifying agents, dispersing agents or preservatives.

When administered orally, the present compositions may be protected from digestion. This can be accomplished either by complexing the antibody or antigen-binding portion thereof with a composition to render it resistant to acidic and enzymatic hydrolysis or by packaging the antibody or antigen-binding portion thereof in an appropriately resistant carrier such as a liposome, e.g., such as shown in U.S. Pat. No. 5,391,377.

For transmucosal or transdermal administration, penetrants appropriate to the barrier to be permeated can be used in the formulation. Such penetrants are generally known in the art, and include, e.g., for transmucosal administration, bile salts and fusidic acid derivatives. In addition, detergents can be used to facilitate permeation. Transmucosal administration can be through nasal sprays or using suppositories. For topical, transdermal administration, the agents are formulated into ointments, creams, salves, powders and gels. Transdermal delivery systems can also include, e.g., patches. The present compositions can also be administered in sustained delivery or sustained release mechanisms. For example, biodegradeable microspheres or capsules or other biodegradeable polymer configurations capable of sustained delivery of a peptide can be included herein.

For inhalation, the present compositions can be delivered using any system known in the art, including dry powder aerosols, liquids delivery systems, air jet nebulizers, propellant systems, and the like. For example, the pharmaceutical formulation can be administered in the form of an aerosol or mist. For aerosol administration, the formulation can be supplied in finely divided form along with a surfactant and propellant. In another aspect, the device for delivering the formulation to respiratory tissue is an inhaler in which the formulation vaporizes. Other liquid delivery systems include, e.g., air jet nebulizers.

Antibodies or antigen binding portions of the antibodies can be delivered alone or as pharmaceutical compositions by any means known in the art, e.g., systemically, regionally, or locally; by intra-arterial, intrathecal (IT), intravenous (IV), parenteral, intra-pleural cavity, topical, oral, or local administration, as subcutaneous, intra-tracheal (e.g., by aerosol) or transmucosal (e.g., buccal, bladder, vaginal, uterine, rectal, nasal mucosa).

In one aspect, the pharmaceutical formulations comprising compositions or nucleic acids, antibodies or fragments thereof are incorporated in lipid monolayers or bilayers, e.g., liposomes, such as shown in U.S. Pat. Nos. 6,110,490; 6,096,716; 5,283,185; and 5,279,833. In other aspects, embodiments of the disclosure include formulations in which the polypeptides or nucleic acids have been attached to the surface of the monolayer or bilayer of the liposomes. Liposomes and liposomal formulations can be prepared according to standard methods and are also well known in the art, such as U.S. Pat. Nos. 4,235,871; 4,501,728 and 4,837,028.

In one aspect, the compositions are prepared with carriers that will protect the antibody or fragments thereof against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

The subject antibodies and fragments thereof in general may be formulated to obtain compositions that include one or more pharmaceutically suitable excipients, surfactants, polyols, buffers, salts, amino acids, or additional ingredients, or some combination of these. This can be accomplished by known methods to prepare pharmaceutically useful dosages, whereby the active compound is combined in a mixture with one or more pharmaceutically suitable excipients. Sterile phosphate-buffered saline is one example of a pharmaceutically suitable excipient.

Examples of routes of administration of the compositions described herein include parenteral injection, e.g., by subcutaneous, intramuscular or transdermal delivery. Other forms of parenteral administration include intravenous, intraarterial, intralymphatic, intrathecal, intraocular, intracerebral, or intracavitary injection. In parenteral administration, the compositions will be formulated in a unit dosage injectable form such as a solution, suspension or emulsion, in association with a pharmaceutically acceptable excipient. Such excipients are inherently nontoxic and nontherapeutic. Examples of such excipients are saline, Ringer's solution, dextrose solution and Hanks' solution. Nonaqueous excipients such as fixed oils and ethyl oleate may also be used. An alternative excipient is 5% dextrose in saline. The excipient may contain minor amounts of additives such as substances that enhance isotonicity and chemical stability, including buffers and preservatives.

Formulated compositions comprising antibodies can be used for subcutaneous, intramuscular or transdermal administration. Compositions can be presented in unit dosage form, e.g., in ampoules or in multi-dose containers, with an added preservative. Compositions can also take such forms as suspensions, solutions or emulsions in oily or aqueous vehicles, and can contain formulatory agents such as suspending, stabilizing and/or dispersing agents. Alternatively, the compositions can be in powder form for constitution with a suitable vehicle, e.g., sterile pyrogen-free water, before use.

The compositions may be administered in solution. The formulation thereof may be in a solution having a suitable pharmaceutically acceptable buffer such as phosphate, Tris (hydroxymethyl) aminomethane-HCl or citrate, and the like. Buffer concentrations should be in the range of 1 to 100 mM. The formulated solution may also contain a salt, such as sodium chloride or potassium chloride in a concentration of 50 to 150 mM. An effective amount of a stabilizing agent such as mannitol, trehalose, sorbitol, glycerol, albumin, a globulin, a detergent, a gelatin, a protamine or a salt of protamine may also be included.

Exemplary, non-limiting ranges for a therapeutically or prophylactically effective amount of an antibody or antigen-binding portion thereof, such as for an anti-DCLK1 antibody, or an anti-DCLK1 antibody-drug conjugate (e.g., wherein the conjugated drug is an auristatin), include but are not limited to 0.001 mg/kg of the subject's body weight to 100 mg/kg of the subject's body weight, more typically 0.01 mg/kg to 50 mg/kg, 0.1 mg/kg to 50 mg/kg, 0.1 mg/kg to 40 mg/kg, 1 mg/kg to 30 mg/kg, or 1 mg/kg to 20 mg/kg, or 2 mg/kg to 30 mg/kg, 2 mg/kg to 20 mg/kg, 2 mg/kg to 15 mg/kg, 2 mg/kg to 12 mg/kg, or 2 mg/kg to 10 mg/kg, or 3 mg/kg to 30 mg/kg, 3 mg/kg to 20 mg/kg, 3 mg/kg to 15 mg/kg, 3 mg/kg to 12 mg/kg, or 3 mg/kg to 10 mg/kg or 10 mg to 1500 mg, as a fixed dosage.

The composition is formulated to contain an effective amount of the present antibody or antigen-binding portion thereof (or conjugate), wherein the amount depends on the animal to be treated and the condition to be treated. In certain embodiments, the present antibody or antigen-binding portion thereof (or drug conjugate thereof) is administered at a dose ranging from about 0.001 mg to about 10 g, from about 0.01 mg to about 10 g, from about 0.1 mg to about 10 g, from about 1 mg to about 10 g, from about 1 mg to about 9 g, from about 1 mg to about 8 g, from about 1 mg to about 7 g, from about 1 mg to about 6 g, from about 1 mg to about 5 g, from about 10 mg to about 10 g, from about 50 mg to about 5 g, from about 50 mg to about 5 g, from about 50 mg to about 2 g, from about 0.05 µg to about 1.5 mg, from about 10 µg to about 1 mg protein, from about 30 µg to about 500 µg, from about 40 pg to about 300 pg, from about 0.1 µg to about 200 mg, from about 0.1 µg to about 5 µg, from about 5 µg to about 10 µg, from about 10 µg to about 25 µg, from about 25 µg to about 50 µg, from about 50 µg to about 100 µg, from about 100 µg to about 500 µg, from about 500 µg to about 1 mg, from about 1 mg to about 2 mg. The specific dose level for any particular subject depends upon a variety of factors including the activity of the specific peptide, the age, body weight, general health, sex, diet, time of administration, route of administration, and rate of excretion, drug combination and the severity of the particular disease undergoing therapy.

The dosage of an administered antibody for humans will vary depending upon such factors as the patient's age, weight, height, sex, general medical condition and previous medical history. In certain non-limiting embodiments, the recipient is provided with a dosage of antibody or antibody fragment (or drug conjugate thereof) that is in the range of from about 1 mg to 1000 mg as a single infusion or single or multiple injections, although a lower or higher dosage also may be administered. The dosage may be in the range of from about 25 mg to 100 mg of the antibody (or fragment) per square meter ($m^2$) of body surface area for a typical adult, although a lower or higher dosage also may be administered. Examples of dosages of antibodies that may be administered to a human subject further include, for example, 1 to 500 mg, 1 to 70 mg, or 1 to 20 mg, although higher or lower doses may be used. Dosages may be repeated as needed, for example, once per week for 4-10 weeks, or once per week for 8 weeks, or once per week for 4 weeks. It may also be given less frequently, such as every other week for several months, or more frequently, such as twice weekly or by continuous infusion.

In some embodiments, the effective amount of an anti-DCLK1 antibody or binding fragment thereof (or drug conjugate thereof) sufficient to inhibit cancer cell or cancer stem cell growth by any degree described herein is in a concentration of about 1 nM, 5 nM, 10 nM, 25 nM, 50 nM, 75 nM, 100 nM, 150 nM, 200 nM, 250 nM, 300 nM, 350 nM, 400 nM, 500 nM, 550 nM, 600 nM, 700 nM, 800 nM, 900 nM, 1 µM, 2 µM, 3 µM, 4 µM, 5 µM, 6 µM, 7 µM, 8 µM, 9 µM, 10 µM, 15 µM, 20 µM, 25 µM, 30 µM, 35 µM, 40 µM, 45 µM, 50 µM, 60 µM, 70 µM, 75 µM, 80 µM, 90 µM, 100 µM, 125 µM, 150 µM, 175 µM, 200 µM, 250 µM, 300 µM, 350 µM, 400 µM, 500 µM, 600 µM, 700 µM, 750 µM, 800 µM, 900 µM, 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 100 mM, 110 mM, 120 mM, 130 mM, 140 mM, 150 mM, 160 mM, 170 mM, 180 mM, 190 mM, 200 mM, 250 mM, 300 mM, 400 mM, 500 mM, 600 mM, 700 mM, 800 mM, 900 mM, 1000 mM, 1 M, 1.1 M, 1.2 M, 1.3 M, 1.4 M, 1.5 M, 1.6 M, 1.7 M, 1.8 M, 1.9 M, 2M, 3M, 4M, 5M, 6M, 7M, 8 M, 9 M, 10 M, 15 M, 20 M, 25 M, 30 M, 35 M, 40M, 45 M, 50 M, 75 M, 100 M, or any range in between any two of the aforementioned concentrations, including said two concentrations as endpoints of the range, or any number in between any two of the aforementioned concentrations.

In some methods, the patient is administered the antibody or binding fragment thereof (or antibody drug conjugate) every one, two, three or four weeks, for example. The dosage depends on the frequency of administration, condition of the patient and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, topical, intranasal or intramuscular. Administration can also be localized directly into a tumor. Administration into the systemic circulation by intravenous or subcutaneous administration is typical. Intravenous administration can be, for example, by infusion over a period such as 30-90 min or by a single bolus injection.

The frequency of administration depends on the half-life of the antibody or antibody-drug conjugate in the circulation, the condition of the patient and the route of administration among other factors. The frequency can be daily, weekly, monthly, quarterly, or at irregular intervals in response to changes in the patient's condition or progression of the cancer being treated. An exemplary frequency for intravenous administration is between twice a week and quarterly over a continuous course of treatment, although more or less frequent dosing is also possible. Other exemplary frequencies for intravenous administration are between once weekly or once monthly over a continuous course of treatment, although more or less frequent dosing is also possible. For subcutaneous administration, an exemplary dosing frequency is daily to monthly, although more or less frequent dosing is also possible.

The number of dosages administered depends on the nature of the cancer (e.g., whether presenting acute or chronic symptoms) and the response of the disorder to the treatment. For acute disorders or acute exacerbations of a chronic disorder between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

In certain non-limiting embodiments, pharmaceutical compositions for parenteral administration are sterile, substantially isotonic, and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, such as (but not limited to) in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use. The concentration of antibody in a liquid formulation can be e.g., 0.01-10 mg/ml, such as 1.0 mg/ml.

As noted above, treatment with antibodies, or binding fragments thereof, of the present disclosure can be combined with chemotherapy, radiation, stem cell treatment, surgery other treatments effective against the disorder being treated.

Useful classes of other agents that can be administered with humanized antibodies to DCLK1 include, for example, antibodies to other receptors expressed on cancerous cells, antitubulin agents (e.g., auristatins), DNA minor groove binders (e.g., PBDs), DNA replication inhibitors, alkylating agents (e.g., platinum complexes such as cis-platin, mono (platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, and the like.

In some embodiments the antibodies comprise a sequence that is 80%, 81%, 82%, 83%, 84%, 85%, 86%, 87%, 88%, 89%, 90%, 91%, 92%, 93%, 94%, 95%, 96% 97%, 98%, 99%, or 100% identical to the sequence of the variable heavy chain and/or variable light chain sequences described herein. In some embodiments the antibodies or antibody fragments comprise a sequence that is 100% identical to the above variable heavy chain and variable light chain sequences over a span of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, or 118 residues.

In certain embodiments, the percent identity of two amino acid sequences (or two nucleic acid sequences) can be determined, for example, by aligning the sequences for optimal comparison purposes (e.g., gaps can be introduced in the sequence of a first sequence). The amino acids or nucleotides at corresponding positions are then compared, and the percent identity between the two sequences is a function of the number of identical positions shared by the sequences (i.e., % identity=(no. of identical positions ÷ total no. of positions)×100). The actual comparison of the two sequences can be accomplished by well-known methods, for example, using a mathematical algorithm. A specific, non-limiting example of such a mathematical algorithm is described in Karlin et al., Proc. Natl. Acad. Sci. USA, 90:5873-5877 (1993), which is incorporated herein by reference in its entirety. Such an algorithm is incorporated into the BLASTN and BLASTX programs (version 2.2) as described in Schaffer et al., Nucleic Acids Res., 29:2994-3005 (2001), which is incorporated herein by reference in its entirety. When utilizing BLAST and Gapped BLAST programs, the default parameters of the respective programs (e.g., BLASTN) can be used. In one embodiment, the database searched is a non-redundant (NR) database, and parameters for sequence comparison can be set at: no filters; Expect value of 10; Word Size of 3; the Matrix is BLOSUM62; and Gap Costs have an Existence of 11 and an Extension of 1.

Several embodiments also encompass variants of the above described antibodies, including any one of the anti-DCLK-1 antibodies designated as CBT-15A and CBT-15G produced and described herein, comprising one or more amino acid residue substitutions in the variable light ($V_L$) domain and/or variable heavy ($V_H$) domain thereof. Several also encompass variants of the above described antibodies with one or more additional amino acid residue substitutions in one or more $V_L$ CDRs and/or one or more $V_H$ CDRs. The antibody or binding fragments thereof generated by introducing substitutions in the $V_H$ domain, $V_H$ CDRs, $V_L$ domain and/or UL CDRs described herein can be tested in vitro and in vivo, for example, for its ability to bind to DCLK1 (by, e.g., immunoassays including, but not limited to ELISAs and BIAcore).

The present disclosure also encompasses nucleic acids which encode the presently disclosed antibodies or antigen-binding portions thereof that specifically bind to DCLK1 isoforms 2 and 4. The nucleic acid may be expressed in a cell to produce the presently disclosed antibody or antigen-binding portion thereof. For example, the isolated nucleic acid of the present disclosure comprises a sequence encoding a peptide that is at least about 70%, at least about 75%, at least about 80%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% identical to an amino acid sequence disclosed herein. A nucleic acid encoding the present antibody or antigen-binding portion thereof may be introduced into an expression vector that can be expressed in a suitable expression system, followed by isolation or purification of the expressed antibody or antigen-binding portion thereof. Optionally, a nucleic acid encoding the present antibody or antigen-binding portion thereof can be translated in a cell-free translation system, e.g., see U.S. Pat. No. 4,816,567.

Anti-DCLK1 antibodies or antigen binding portions thereof can be produced by host cells transformed with DNA encoding light and heavy chains (or CDR portions thereof) of a desired antibody. Antibodies can be isolated and purified from these culture supernatants and/or cells using standard techniques. For example, a host cell may be transformed with DNA encoding the light chain, the heavy chain, or both, of an antibody. Recombinant DNA technology may also be used to remove some or all of the DNA encoding either or both of the light and heavy chains that is not necessary for binding, e.g., the constant region.

As used herein, the term "cancer stem cell(s)" refers to a cell that can proliferate extensively or indefinitely and give rise to a large proportion of cancer cells in a cancer. In some aspects, the large proportion of cancer cells represents a majority of the cancer cells in a given cancer. For purposes of illustration, but not limitation, a cancer stem cell can be a founder of a tumor or a progenitor of the cancer cells that comprise the majority of a cancer's mass. In some aspects, cancer stem cells refer to cells that divide to form one or more tumors when implanted into an immunocompromised individual, in the absence of any additional mutation to the cells or introduction of exogenous cell proliferation-inducing or carcinogenic agents. In some aspects cancer stem cells divide to yield additional cancer stem cells as well as terminally differentiated cancer cells or cancer tissue.

As used with respect to blocking cancer cell growth, the term "effective amount" refers to an amount of anti-DCLK1 antibody sufficient to reduce the growth of cancer cells by any degree. Any assay known in the art can be used to measure cancer cell growth. For example, cancer cell growth can be measured by colony count, total cell count, or volume/size of a cell population, colony, or tumor. In several embodiments, cancer cell growth can be measured by the tumor sphere growth assay. As used with respect to blocking cancer stem cell growth, the term "effective amount" refers to an amount of anti-DCLK1 antibody sufficient to reduce the growth of cancer stem cells by any degree. Any assay known in the art can be used to measure cancer stem cell growth. For example, cancer stem cell growth can be measured by colony count, total cell count, or volume/size of a cell population or colony. In several embodiments, cancer stem cell growth can be measured by the tumor sphere growth assay.

In certain embodiments, an effective amount of an anti-DCLK1 antibody or binding fragment thereof can block cancer cell or cancer stem cell growth as measured by a reduction of at least 5%, at least 10%, at least 15%, at least 20%, at least 30%, at least 40%, at least 50%, at least 60%, at least 70%, at least 80%, at least 90%, at least 95%, at least 96%, at least 97%, at least 98%, at least 99%, or 100% in the cancer cell or cancer stem cell population or tumorsphere growth or other appropriate measure of cell or tumor growth, or any percentage in between any of the aforementioned numbers.

For example, in some embodiments, an effective amount of an anti-DCLK1 antibody or binding fragment thereof can block cancer cell or cancer stem cell growth as measured by a reduction of at least about 5%-95%, at least about 5%-75%, at least about 5% to 50%, at least about 10% to 95%, at least about 10% to 75%, at least about 10% to 50%, at least about 10% to 25%, at least about 20 to 95%, at least about 20%-80%, at least about 20%-60%, at least about 20%-50%, at least about 25%-90%, at least about 25%-75%, or at least about 30%-50% in the cancer cell or cancer stem cell population or tumorsphere growth, or other appropriate measure.

In other embodiments, the effective amount of an anti-DCLK1 antibody or binding fragment thereof can block or inhibit cancer cell or cancer stem cell growth as measured by at least about a 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5, 5.0, 10, 25, 50, 75, 100, 200, 500, or 1000-fold reduction in the cancer cell or cancer stem cell population or tumorsphere growth, or any fold-reduction in between any of the aforementioned numbers.

In some embodiments, the inhibited cell is a tumor cell, including but not limited to a colorectal tumor cell (i.e., colon, rectum, intestinal, or stomach tumor cell), a breast cancer cell, a lung cancer cell, a renal cancer cell, or a pancreatic tumor cell. In some embodiments, the tumor cell can express elevated levels of DCLK1 protein. In some embodiments, the anti-DCLK1 antibody or binding fragment thereof provided herein inhibits growth of the tumor cell, for example, by reducing the number and/or frequency of cancer cells or cancer stem cells.

Some embodiments of the present disclosure include methods of treating subjects having such cancers by administering a therapeutically effective amount of an anti-DCLK1 antibody or binding fragment thereof as provided herein. In some embodiments, the cancer is selected from pancreatic cancer, colorectal cancer, lung cancer, renal cancer, and breast cancer, such as triple negative breast cancer.

Some embodiments include methods of treating a disease comprising administering a therapeutically-effective amount of an anti-DCLK1 antibody or binding fragment thereof as provided herein to a subject in need of such treatment, in combination with at least one additional therapeutic agent. The therapeutic agent may be conjugated to the antibody or binding fragment thereof, directly or via a linker as discussed elsewhere herein. In some embodiments, the additional therapeutic agent comprises a chemotherapeutic agent. In some embodiments, the additional therapeutic agent comprises a biologic agent. Some embodiments include administering an anti-DCLK1 antibody or binding fragment thereof as provided herein in combination with a chemotherapeutic agent and a biologic agent. Some embodiments of the methods provided herein include determining the level of DCLK1 protein expression in a tumor or cancer.

Some embodiments of the methods provided herein include identifying a subject for treatment with an anti-DCLK1 antibody or binding fragment thereof as provided herein. Some embodiments include determining if the subject has a tumor or circulating cells comprising an elevated expression level of DCLK1 as compared to the expression of the same DCLK1 protein in normal tissue. Some embodiments include selecting a subject for treatment if the tumor or circulating cells have an elevated level of DCLK1 expression.

Some embodiments provided herein include kits. In some kit embodiments, a kit can include an antibody or binding fragment thereof, such as a humanized antibody or humanized binding fragment thereof, as described herein. In some embodiments, the antibody or binding fragment thereof is lyophilized. In some embodiments, the antibody or binding fragment thereof is in aqueous solution, or other carrier as described herein. In some embodiments, the kit includes a pharmaceutical carrier for administration of the antibody. In some embodiments, the kit also includes a chemotherapeutic agent. Certain embodiments of the present disclosure include kits containing components suitable for treatments or diagnosis. Exemplary kits may contain at least one anti-DCLK1 antibody or binding fragment thereof as described herein. A device capable of delivering the kit components by injection, for example, a syringe for subcutaneous injection, may be included. Where transdermal administration is used, a delivery device such as hollow microneedle delivery device may be included in the kit. Exemplary transdermal delivery devices are known in the art, such as a hollow Microstructured Transdermal System (e.g., 3M Corp.), and any such known device may be used. The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Alternatively, the antibody or fragment may be delivered and stored as a liquid formulation. Other containers that may be used include, but are not limited to, a pouch, tray, box, tube, or the like. Kit components may be packaged and maintained sterilely within the containers. Another component that can be included is instructions for the use of the kit for treatment of certain diseases or conditions or for the diagnosis of such.

Experimental

Having generally described embodiments drawn to anti-DCLK1 antibodies or antigen-binding fragments thereof against DCLK1, hybridomas or other cell lines expressing such antibodies or antigen-binding fragments thereof, and nucleic acids, and vectors and host cells comprising nucleic acids, which encode such antibodies and binding fragments, and methods of blocking cancer stem cell growth with such antibodies and antigen-binding fragments, a further understanding can be obtained by reference to certain specific examples which are provided for purposes of illustration only and are not intended to be limiting.

Methods

Construction of Human DCLK1 Isoform 2 cDNA Sequence

For the DCLK1 isoform 2 construct we utilized a 364 bp gBlock synthetic DNA (IDT) containing a 5'-ScaI and 3'-EcoRI restriction enzyme digestion sites. This gBlock also contains a part of human DCLK1 isoform 1 sequence shared with isoform 2, with the addition of the unique DCLK1 isoform 2 C-terminal sequence (NCBI Reference Sequence: XM_005266592.2). The vector containing DCLK1 isoform 1 and the gBlock were digested with EcoRI and ScaI Both digested vector and gBlock fragment were gel purified and DCLK1 isoform 2 was constructed by ligating the digested vector with the synthetic DNA fragment. The ligated cDNA product was confirmed by automatic sequencing. The DCLK1 isoform 2 vector was then further constructed into Lentivirus construct as described previously (Weygant N, Qu D, Berry W L, May R, Chandrakesan P, Owen D B, et al. Small molecule kinase inhibitor LRRK2-IN-1 demonstrates potent activity against colorectal and pancreatic cancer through inhibition of doublecortin-like kinase 1. Molecular cancer. 2014; 13(1):103). RCC cell line Caki-2 was infected with Lentivirus containing human DCLK1 cDNA sequence to overexpress DCLK1 Isoform 2/long-α (caki2-dsRed-DCLK1) or red fluorescent protein (RFP) cDNA as control (caki2-dsRed) and selected to 100% expression with puromycin.

Cell Culture

Caki-2 and ACHN human clear cell renal carcinoma cells were obtained directly from the American Type Culture Collection (ATCC) where they were tested and authenticated via morphology, karyotyping, and PCR to rule out interspecies and intraspecies contamination. Cells were cultured in RPMI medium containing 10% fetal bovine serum (FBS) (Sigma) at 37° C. and 5% $CO_2$.

siRNA-Mediated Knockdown of DCLK1

$10^5$ Caki-2 or ACHN cells were seeded into 6 cm dishes and allowed to attach overnight. Lipofectamine 3000 (Invitrogen) was complexed with 25 nM of commercially validated siRNA targeting human DCLK1 coding region (siDCLK; Santa Cruz Biotechnology sc-45618) or 25 nM scrambled sequence (siSCR) not matching any known genes. After 72 h of transfection, RNA and protein were collected to confirm knockdown.

Quantitative Real-Time RT-PCR

Total RNA was isolated from cells using Tri Reagent according to the manufacturer's instructions. Reverse transcription was performed using SuperScript II and random hexanucleotide primers (Invitrogen). Then complementary DNA was used to perform real-time polymerase chain reaction (PCR) on an iCycler IQ5 Thermal Cycler (BioRad) using SYBR Green (Molecular Probes). To detect specific transcripts, gene-specific primers and JumpStart™ Taq DNA polymerase (Sigma) were used in the reaction. β-actin was used to normalize the threshold value and quantitative changes in mRNA were assessed as fold-change relative to control. The Student's t-test was used to determine statistical significance.

Western Blotting

Lysates from ACHN or CAKI2 cells were subjected to Western blot analysis. The concentration of total proteins was determined by BCA protein assay (Pierce, Rockford, Ill.). 40 µg of protein lysates were size separated on a 4%-20% SDS polyacrylamide gel and transferred onto a PVDF membrane. The membrane was blocked in 1% caseine for 30 minutes and probed with primary antibody α-DCLK1 (ABCAM, ab31704), HIF-1α (ABCAM, ab2185), Vimentin (Santa Cruz, S.C.-7557), ALDH1A1 (ABCAM, ab52492), β-Actin (ABCAM, ab8226) overnight at 4° C. The membrane was then washed 3 times with TBST and probed with species-appropriate secondary antibody (cw800-conjugated) for 30 mins at room temperature protected from light. Finally, proteins were detected using a LICOR Odyssey Infrared Imager and density quantification was performed in Image Studio Lite (LICOR) where appropriate.

Proliferation/Drug Resistance Assay

Cells (5000/well) were seeded into a 96-well tissue culture plate in quadruplicate. The cells were cultured in the presence of sorafenib, sunitinib, everolimus, temsirolimus with DMSO as a vehicle at 100, 50, 25, 12.5, 6.25, 3.13, 1.56, 0.78, 0.39, 0.20, and 0.10 µM, or vehicle (sorafenib, sunitinib); and 300, 150, 75, 37.5, 18.8, 9.38, 4.69, 2.34, 1.17, 0.59, and 0.29 µM, or vehicle (everolimus, temsirolimus). 48 or 72 h after incubation, 10 µL of MTT (RND Systems) was added to each well and cells were incubated at 37° C. for 4 h. When dark crystalline precipitate became visible, 50 µL DMSO containing 266 mM $NH_4OH$ was added to the wells. In order to fully dissolve the precipitated MTT crystals, the plate was placed on a shaker at low speed for 1 min and a microplate reader was used to read the $OD_{570}$ for each well. Finally, results were averaged and normalized to DMSO (vehicle) control-treated wells.

2D Colony Formation Assay

Cells (100/well) were seeded into 6-well plates with fresh cell culture media containing 10% FBS and either DMSO or sunitinib at 0.5 or 5 µM. After 72 h treatment, the media was refreshed and the cells were allowed to grow for 9-15 days. Following the period of colony formation, dishes were washed with PBS and fixed with glacial acetic acid/methanol solution (1:3). Following fixation, 0.5% crystal violet was used to stain the colonies and excess stain was removed by gently washing with tap water. After drying, colonies were counted under a stereomicroscope using a 1 $cm^2$ grid. Four squares from four quadrants were counted for each plate. In order to obtain the relative colony formation, the results were normalized to DMSO for each cell line. Stained colonies were then imaged and analyzed using ImageJ.

3D Colony Formation Assay

Reduced growth-factor matrigel (Corning) was mixed with the cell suspensions containing RPMI medium (volume 1:1). 100 µL of the mixture was pipetted into 96-well plates at a density of 50 cells/well. After matrigel solidification, 50 µL RPMI medium with 10% fetal calf serum was added to each well. The plates were then incubated at 37° C. under 5% $CO_2$. The media was refreshed once a week and the cells were monitored for colony formation. For drug response, after drug treatment for 72 h, the cells were trypsinized and seeded following the protocols mentioned above and media was refreshed as described above. The cells were allowed to grow 10-15 days to form colonies, defined as consisting of more than 15 cells, and plates were washed with PBS and fixed with formalin. After that, the colonies in each well were counted manually.

Flow Cytometry

To assess cell cycle status, cells were trypsinized, centrifuged at 4° C., washed with cold PBS, and then fixed in 70% ethanol on ice for >2 h. Following fixation the cells were washed with PBS again and incubated with propidium iodide (50 µg/ml) and treated with RNAse A. In another experiment to analyze the expression of DCLK1, cells were trypsinized, centrifuged, washed, and then 5 µL activated ALDEFLUOR and 5 µL anti-DCLK1 antibody conjugated with respective fluorochromes were added and allowed to incubate for 60 min at 37° C. Following incubation the cells were washed with ALDEFLUOR buffer. Data was collected on FACS Calibur and analyzed in ModFit LT or Flowing Software. To analyze the expression level of ALDH, cells were resuspended in ALDEFLUOR assay buffer containing ALDH substrate, BAA (Bodipy-aminoacetaldehyde) (50 mg dry reagent), with or without 5 ml of the specific ALDH inhibitor diethylaminobenzaldehyde (DEAB 1.5 mM in 95% ethanol stock solution), as a negative control. After 60 mins incubation at 37° C., data was collected by FACS Calibur. For DCLK1 extracellular-domain based cell sorting, cells were trypsinized and washed as described above. After washing cells were incubated with anti-DCLK1 antibody conjugated with fluorochrome for 60 min on ice and sorted using BD Biosciences FACSAria III. Sorted cells were kept on ice and seeded directly into ECM.

Monoclonal Antibodies

As noted above, DCLK1 comprises four different primary human isoforms generated from two promoters termed alpha and beta. All isoforms have a shared kinase domain and autophosphorylation region. The alpha promoter produces two doublecortin-binding 82 kDa isoforms with differing C-terminal regions. The beta promoter produces two shortened primarily kinase domain 52 kDa isoforms with equivalent differing C-terminal regions. Through the use of sequence analysis and homology modeling the shared extracellular C-terminal region of isoforms 2 and 4 was identified, and a set of immunogens against this region were prepared to generate multiple antibodies. The sequences of the immunogens are shown in Table 3.

TABLE 3

Peptide immunogens from C-terminal region of DCLK1 isoforms 2 and 4 for antibody generation.

| Immunogen No. | Amino acid sequence | SEQ ID NO: |
|---|---|---|
| 1 | RRRNQDVRSRYKAQ | 3 |
| 2 | ELNSESEDYSPS | 4 |
| 3 | DVRSRYKAQPA | 5 |
| 4 | PELNSESEDYSPSSS | 6 |
| 5 | RSRYKAQPAPPELNS | 7 |
| 6 | DVRSRYKAQPAPPE | 8 |
| 7 | RYKAQPAPPELNSES | 9 |
| 8 | DYSPSSSETVRSPNSPF | 10 |
| 9 | EDYSPSSSETVRSPN | 11 |
| 10 | ESEDYSPSSSETVR | 12 |

The immunogen sequences were linked to KLH to form KLH-linked. Balb/c mice were injected subcutaneously with these KLH-linked peptides and boosted 4 weeks later. Immunized mouse spleens were removed after boosting and fused with myeloma cells. Clones were screened by ELISA against the specific peptides and purified DCLK1 protein for selection.

Figure 2:
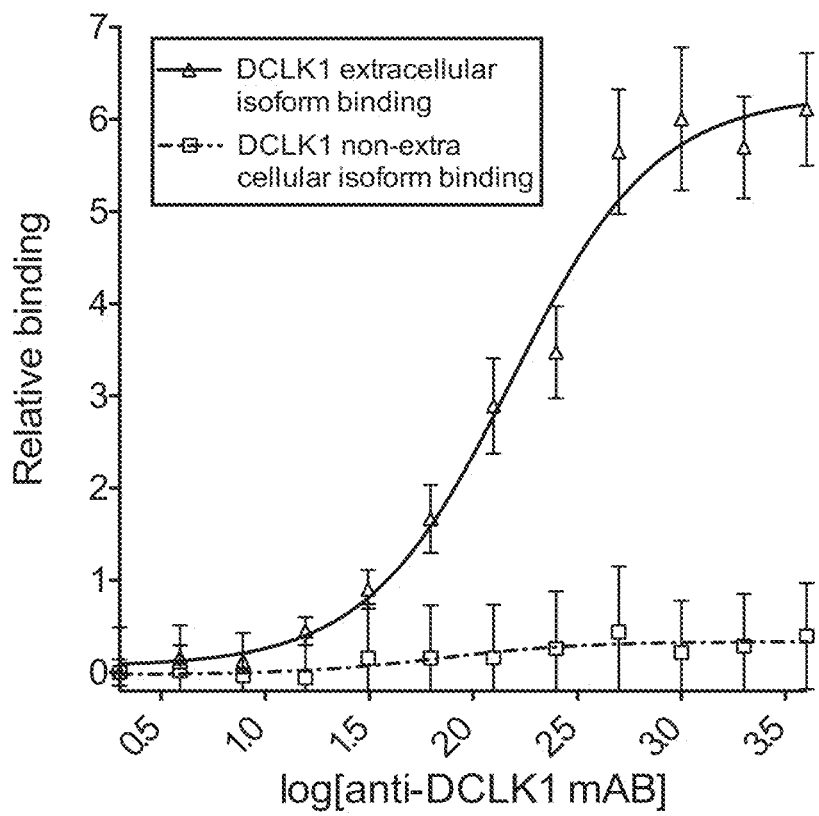
FIG. 2 shows ELISA results demonstrating that CBT-15 mABs selectively detect extracellular DCLK1 isoform 4 (upper line) and non-selectively bind intracellular DCLK1 isoform 1 (lower line).
Figure 3:
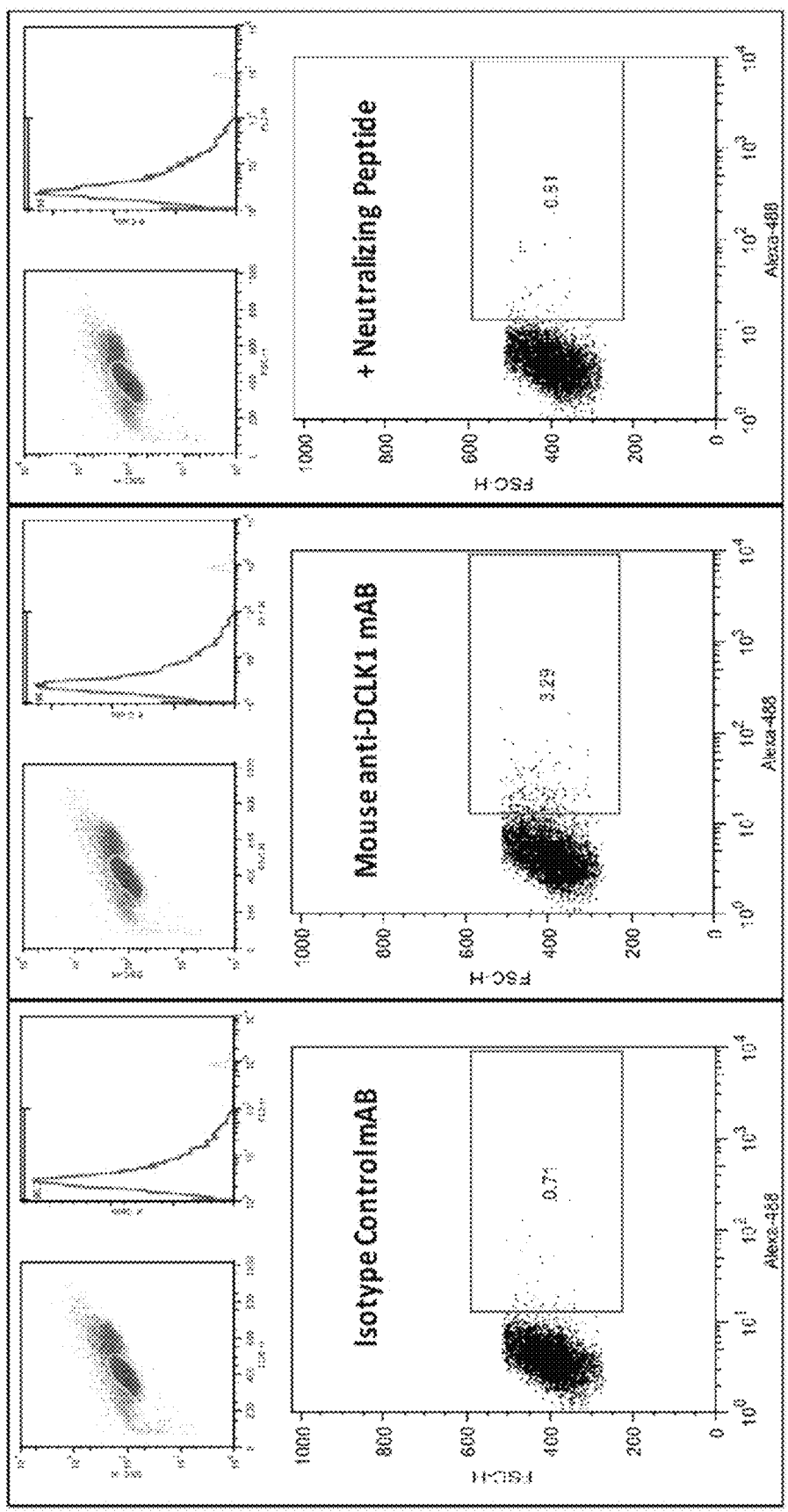
FIG. 3 shows fluorescence-activated cell sorting (FACS) analysis plots demonstrating that CBT-15 monoclonal antibodies detect a small subpopulation of AsPC-1 human pancreatic cells expressing extracellular DCLK1.

The resulting monoclonal antibodies produced from this screening process included an Immunoglobulin A species (CBT-15A) and an Immunoglobulin G213 species (CBT-15G). Following purification of the resulting antibodies, their affinity for DCLK1 was confirmed by Western blotting against DCLK1 isoform 4 purified protein (FIG. 1). ELISA performed with both DCLK1 isoform 4 and DCLK1 isoform 1 purified protein showed that CBT-15 monoclonal antibodies raised from immunogen no. 8 (SEQ ID NO:10), were highly selective for the DCLK1 extracellular domain present in DCLK1 isoform 4 as compared to the non-extracellular domains present in DCLK1 isoform 1 (FIG. 2). The ability of these antibodies to bind extracellular DCLK1 was further apparent in FACS sorting experiments. Live AsPC-1 human pancreatic cancer cells were stained with isotype control, CBT-15A antibodies, or CBT-15A antibodies plus neutralizing peptide at 10 µg/mL on ice in non-permeablizing conditions. FACS sorting demonstrated that CBT-15A could sort the live extracellular DCLK1+ population in this pancreatic cancer cell line that was previously shown to have cancer stem cell like characteristics (FIG. 3). Together these findings demonstrated that monoclonal antibodies raised against immunogen no. 8 (SEQ ID NO:10) of the extracellular DCLK1 C-terminus are capable of selectively targeting this domain in vitro.

After confirming the ability of the CBT-15 mABs to bind to extracellular DCLK1, a cell line secreting a chimera variation of the CBT-15G (the chimera referred to herein as CBT-15X) was prepared as follows:

1. RNA was purified from monoclonal hybridoma cells secreting CBT-15G antibody.

2. cDNA was created using a primer downstream of the last variable region for mouse heavy chain constant and light chain kappa constant and the heavy chain and light chain variable cDNA and amino acid sequences for CBT-15G were identified (see below).

3. Each RT-reaction was subject to PCR using a degenerate primer sets (USBIO, 11904-10A) to amplify all likely rearrangements.

4. To create the human/mouse IgG chimeric antibody, PCR fragments from the above reaction were inserted into pFUSEss-CHIg-hG1 to express DCLK1 heavy chain and pFUSEss-CLIg-hK to express DCKL1 light chain kappa.

Retained specific binding affinity of the CBT-15X chimera for DCLK1 was confirmed by Western blot against DCLK1 purified protein (FIG. 1).

In Vitro PBMC-Killing Assay

ACHN cells were seeded into a 96-well plate at $5 \times 10^4$ cells per well and allowed to attach overnight at 37° C. CBT-15 mAB or isotype control mAB were added to the ACHN wells at concentrations of 100 µg/mL in quadruplicate and incubated at 37° C. for 72 h. After mAB treatment, the media was replaced and $1.25 \times 10^5$ primary human PBMC cells (ATCC) were co-incubated with the ACHN cells for 72 h. Finally, luminescent CaspaseGlo® 3/7 activity (Promega) assay was performed according to the manufacturer's protocol as a surrogate measure of apoptosis.

Xenograft Tumor Study

ACHN cells ($5 \times 10^5$) were injected subcutaneously into the flanks of male athymic nude mice and allowed to grow until the tumor reached an average volume of 100 mm³. Once this volume was reached, CBT-15 mAB or isotype control mAB were delivered intraperitoneally at 25 mg/kg biweekly and tumor volume measurements were taken every other day. Horizontal and vertical tumor diameter was measured on each injection date with calipers and tumor volume was calculated using the formula: tumor volume=$0.5 \times \text{length} \times \text{width}^2$. At the end of the injection period mice were killed by $CO_2$ asphyxiation and tumors were excised, weighed, and measured. All animal experiments were performed in accordance with standards set forth by the University of Oklahoma Health Sciences Center's Institutional Animal Care and Use Committee.

Immunohistochemistry

Immunohistochemistry was performed as previously described (19) for PD-L1 and DCLK1 using a commercially available renal cancer microarray (US Biomax, KD2085). Staining results were quantified by experienced clinical pathologists.

Statistical Analyses

All statistical analyses were performed using SPSS Statistics 19, Graphpad Prism 6.0, and Microsoft Excel. One-way ANOVA and the Student's T-test were used to determine statistical significance. For all analyses p<0.05 was considered to be statistically significant.

Results

The following light chain and heavy chain variable cDNA and amino acid sequences for CBT-15A were determined:

```
Heavy chain variable cDNA sequence of CBT-15A:
                                          (SEQ ID NO: 13)
GACGTGAAGCTCGTGGAGTCTGGGGGAGGCTTAGTGAAGCTTGGAGGGTC

CCTGAAACTCTCCTGTGCAGCCTCTGGATTCACTTTCAGTAGCTATTACA

TGTCTTGGGTTCGCCAGACTCCAGAGAAGAGGCTGGAGTTGGTCGCAGCC

ATTAATAGTAATGGTGGTAGCACCTACTATCCAGACACTGTGAAGGGCCG

ATTCACCATCTCCAGAGACAATGCCAAGAACACCCTGTACCTGCAAATGA

GCAGTCTGAAGTCTGAGGACACAGCCTTGTATTACTGTGCAAGACATGGG

GGTAACTACTGGTACTTCGATGTCTGGGGCGCAGGGACCACGGTCACCGT

CTCCTCA.

Heavy chain variable amino acid sequence of
CBT-15A:
                                          (SEQ ID NO: 14)
DVKLVESGGGLVKLGGSLKLSCAASGFTFSSYYMSWVRQTPEKRLELVAA

INSNGGSTYYPDTVKGRFTISRDNAKNTLYLQMSSLKSEDTALYYCARHG

GNYWYFDVWGAGTTVTVSS.

Light chain variable cDNA sequence of CBT-15A:
                                          (SEQ ID NO: 15)
GACATTGTGATGTCACAGTCTCCATCCTCCCTAGCTGTGTCAGTTGGAGA

GAAGGTTACTATGAGCTGCAAGTCCAGTCAGAGCCTTTTATATAGTAGCA

ATCAAAAGAACTACTTGGCCTGGTACCAGCAGAAACCAGGGCAGTCTCCT

AAACTGCTGATTTACTGGGCATCCACTAGGGAATCTGGGGTCCCTGATCG

CTTCACAGGCAGTGGATCTGGGACAGATTTCACTCTCACCATCAGCAGTG

TGAAGGCTGAAGACCTGGCAGTTTATTACTGTCAGCAATATTATAGCTAT

CCGTACACGTTCGGAGGGGGGACCAAGCTGGAAATAAAA.

Light chain variable amino acid sequence of
CBT-15A:
                                          (SEQ ID NO: 16)
DIVMSQSPSSLAVSVGEKVTMSCKSSQSLLYSSNQKNYLAWYQQKPGQSP

KLLIYWASTRESGVPDRFTGSGSGTDFTLTISSVKAEDLAVYYCQQYYSY

PYTFGGGTKLEIK.

Heavy chain variable complementarity determining
regions (VH CDRs) of CBT-15A:
VH CDR1:
                                          (SEQ ID NO: 17)
GFTFSSYY.

VH CDR2:
                                          (SEQ ID NO: 18)
INSNGGST.

VH CDR3:
                                          (SEQ ID NO: 19)
ARHGGNYWYFDV.

Light chain variable complementarity determining
regions (VL CDRs) of CBT-15A:
VL CDR1:
                                          (SEQ ID NO: 20)
QSLLYSSNQKNY.

VL CDR2:
                                          (SEQ ID NO: 21)
WAS.

VL CDR3:
                                          (SEQ ID NO:22)
QQYYSYPYT.
```

Heavy chain and Light chain variable cDNA and amino acid sequences for CBT-15G were also determined:

```
Heavy chain variable cDNA sequence of CBT-15G:
                                          (SEQ ID NO: 23)
GAGGTCCAGCTGCAGCAGTCTGGGACTGCGCTGGCAAGGCCTGGGGCTTC

CGTGAAGATGTCCTGCAAGGCTTCTGGCTACAGCTTTACCAGCTACTGGA

TGCACTGGGTAAAACAGAGGCCTGGACAGGGTCTAGAATGGATTGGTGCT

ATTTATCCTGGAAAAAGTGATACTAGCTACAACCAGAAGTTCAAGGGCAA

GGCCAAACTGACTGCAGTCACATCCGCCAGCACTGCCTACATGGAGCTCA

GCAGCCTGACAAATGAGGACTCTGCGGTCTATTACTGTACAAGATATGGT

AAGGGTGCTATGGACTACTGGGGTCAAGGAACCTCAGTCACCGTCTCCTC

A.

Heavy chain variable amino acid sequence of
CBT-15G:
                                          (SEQ ID NO: 24)
EVQLQQSGTALARPGASVKMSCKASGYSFTSYWMHWVKQRPGQGLEWIGA

IYPGKSDTSYNQKFKGKAKLTAVTSASTAYMELSSLTNEDSAVYYCTRYG

KGAMDYWGQGTSVTVSS.

Light chain variable cDNA sequence of CBT-15G:
                                          (SEQ ID NO: 25)
GACATTGTGCTGACCCAATCTCACAAATTCATGTCCACATCAGTAGGAGA

CAGGGTCACCATCACCTGCAAGGCCAGTCAGGATGTGAATACTGCTGTAG

CCTGGTATCAAAAAAAACCAGGGCAATCTCCTAAACTGCTGATTTACTGG

GCATCCACCCGGCTCACTGGAGTCCCTGATCGCTTCACAGGCAGTGGATC

TGGGACAGATTATACTCTCACCATCAGCAGTGTGCAGGCTGAAGACCTGG

CACTTTATTACTGTCAGCAACATTATAGTACTCCGTACACGTTCGGAGGG

GGGACCAAGCTGGAAATAAAA.

Light chain variable amino acid sequence of
CBT-15G:
                                          (SEQ ID NO: 26)
DIVLTQSHKFMSTSVGDRVTITCKASQDVNTAVAWYQKKPGQSPKLLIYW

ASTRLTGVPDRFTGSGSGTDYTLTISSVQAEDLALYYCQQHYSTPYTFGG

GTKLEIK.

Heavy chain variable complementarity determining
regions (VH CDRs) of CBT-15G:
VH CDR1:
                                          (SEQ ID NO: 27)
SYWMH.
```

```
VH CDR2:
                                        (SEQ ID NO: 28)
AIYPGKSDTSYNQKFKG.

VH CDR3:
                                        (SEQ ID NO: 29)
YGKGAMDY.

Light chain variable complementarity determining
regions (VL CDRs) of CBT-15G:
VL CDR1:
                                        (SEQ ID NO: 30)
KASQDVNTAVA.

VL CDR2:
                                        (SEQ ID NO: 31)
WASTRLT.

VL CDR3:
                                        (SEQ ID NO: 32)
QQHYSTPYT.
```

Accordingly, in some embodiments, an anti-DCLK1 antibody provided in the present disclosure comprises a variable heavy chain CDR1 comprising GFTFSSYY (SEQ ID NO:17), a variable heavy chain CDR2 comprising INSNGGST (SEQ ID NO:18), and a variable heavy chain CDR3 comprising ARHGGNYWYFDV (SEQ ID NO:19). In some embodiments, an anti-DCLK1 antibody provided herein comprises a variable light chain CDR1 comprising QSLLYSSNQKNY (SEQ ID NO:20), a variable light chain CDR2 comprising WAS (SEQ ID NO:21), and a variable light chain CDR3 comprising QQYYSYPYT (SEQ ID NO:22). In some embodiments, 1, 2, 3, 4, 5, or 6 of the CDR sequences include 1, 2, or 3 amino acid substitutions. In some embodiments, the amino acid substitutions are conservative amino acid substitutions.

In some embodiments, an anti-DCLK1 antibody provided herein comprises a variable heavy chain CDR1 comprising SYWMH (SEQ ID NO:27), a variable heavy chain CDR2 comprising AIYPGKSDTSYNQKFKG (SEQ ID NO:28), and a variable heavy chain CDR3 comprising YGKGAMDY (SEQ ID NO:29). In some embodiments, an anti-DCLK1 antibody provided herein comprises a variable light chain CDR1 comprising KASQDVNTAVA (SEQ ID NO:30), a variable light chain CDR2 comprising WASTRLT (SEQ ID NO:31), and a variable light chain CDR3 comprising QQHYSTPYT (SEQ ID NO:32). In some embodiments, 1, 2, 3, 4, 5, or 6 of the CDR sequences include 1, 2, or 3 amino acid substitutions. In some embodiments, the amino acid substitutions are conservative amino acid substitutions.

In some embodiments, an anti-DCLK1 antibody provided herein comprises an antibody, or binding fragment thereof, which comprises a heavy chain variable region having at least 80% or at least 90% sequence identity (or other % identity disclosed herein) to a specific heavy chain variable region sequence (e.g., SEQ ID NO:14 or SEQ ID NO:24) described herein, and/or a light chain variable region having at least 80% or at least 90% sequence identity (or other % identity disclosed herein) to a specific light chain variable region sequence (e.g., SEQ ID NO:16 or SEQ ID NO:26) described herein.

DCLK1 Overexpression Drives the Expression of Stemness-Supporting Markers

Figure 4:
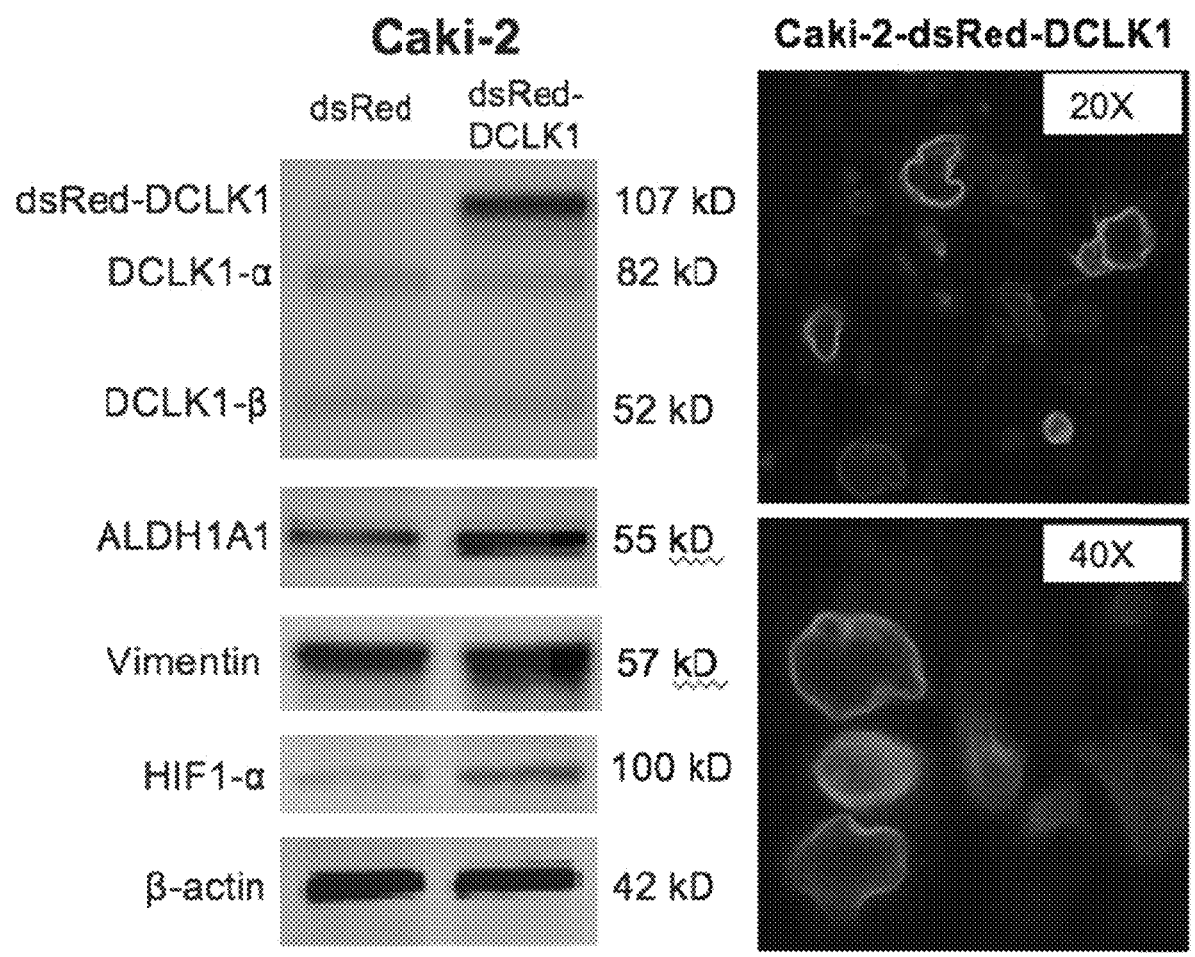
FIG. 4 shows that overexpression of DCLK1 isoform 2 in Caki-2 human renal cancer cells is localized to the microtubules and results in upregulation of markers hypoxia-inducible transcription factor-1α (HIF-1α), Aldehyde dehydrogenase1A1 (ALDH1A1), and Vimentin protein expression.
Figure 5:
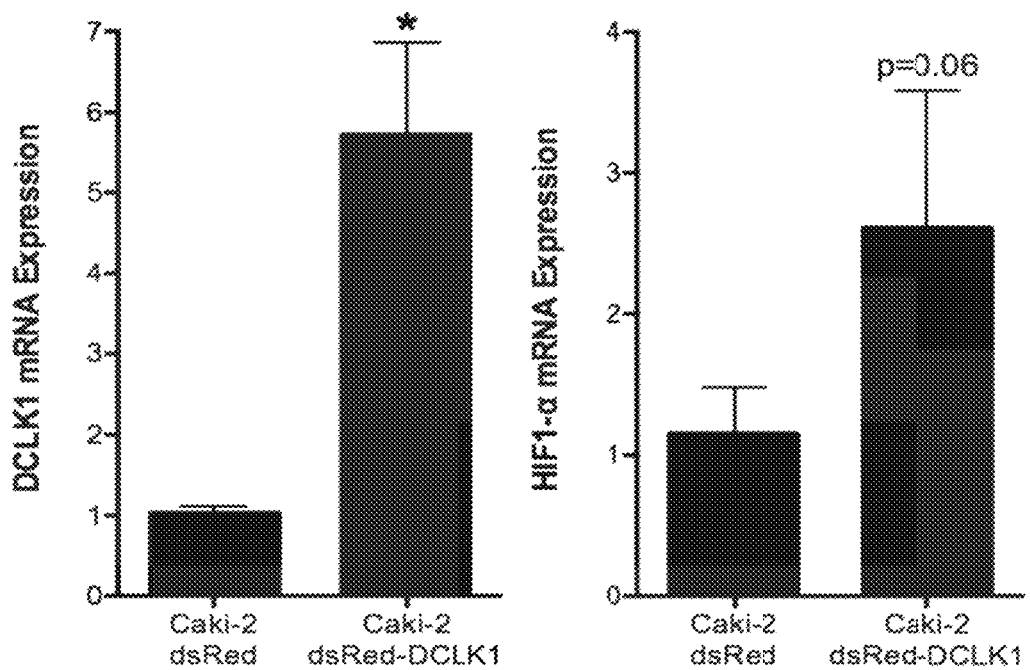
FIG. 5 is a graph showing that when DCLK1 isoform 2 is overexpressed, HIF-1α mRNA is also overexpressed in Caki-2 human renal cancer cells.

In order to assess DCLK1's role in renal cancer progression, we overexpressed DCLK1 (isoform 2; DCLK1-long-α) in Caki-2 RCC cells via lentiviral infection (Caki-2-dsRed-DCLK1). Overexpression was confirmed by real-time PCR and Western blotting revealing a >5 fold increase in DCLK1 mRNA level and comparable increase in protein expression compared to vector control infected cells (Caki-2-dsRed; FIGS. 4-5). The alpha-promoter driven isoforms of DCLK1 have doublecortin microtubule-binding domains and are often associated with microtubules, which are important in cell cycle regulation (Lin P T, Gleeson J G, Corbo J C, Flanagan L, Walsh C A. DCAMKL1 encodes a protein kinase with homology to doublecortin that regulates microtubule polymerization. J Neurosci. 2000; 20(24):9152-61). Fluorescence microscopy revealed this microtubule/cytoskeletal-associated expression in the dsRed-tagged DCLK1-overexpressing cells (FIG. 4).

According to previous studies, including our own, the mesenchymal marker vimentin, may prognosticate overall survival in patients with RCC. Moreover, we previously demonstrated that targeted knockdown of DCLK1 dramatically reduces the expression of vimentin in RCC. In agreement with these previous findings, overexpression of DCLK1 induced expression of vimentin protein (FIG. 4). HIF-1α is implicated in renal cancer development and stemness, mediates EMT through activation of histone deacetylase 3 (HDAC3) in both epithelial and mesenchymal cells, and maintains the generation of cancer stem cells by driving anaerobic glycolysis. Previously, we showed that DCLK1 is induced under hypoxia and that siRNA-mediated DCLK1 knockdown decreases HIF-1α expression. In the present work, HIF-1α mRNA and protein were shown to be upregulated by DCLK1 overexpression (FIGS. 4-5). Aldehyde dehydrogenase (ALDH/ALDH1A1) is one of only a few putative RCC stem cell markers linked to increased tumorigenicity and decreased recurrence-free and overall survival in patients. High ALDH activity also predicts increased invasiveness and metastatic potential in multiple tumor types including esophageal, breast, ovarian, and others and drug resistance in Wilms' tumors. We previously demonstrated that DCLK1 knockdown in RCC significantly reduced the expression of ALDH. In agreement with these findings, ALDH protein expression was significantly upregulated in Caki-2 cells overexpressing DCLK1 (FIG. 4), suggesting that ALDH may be a key DCLK1 effector protein in RCC.

Figure 6:
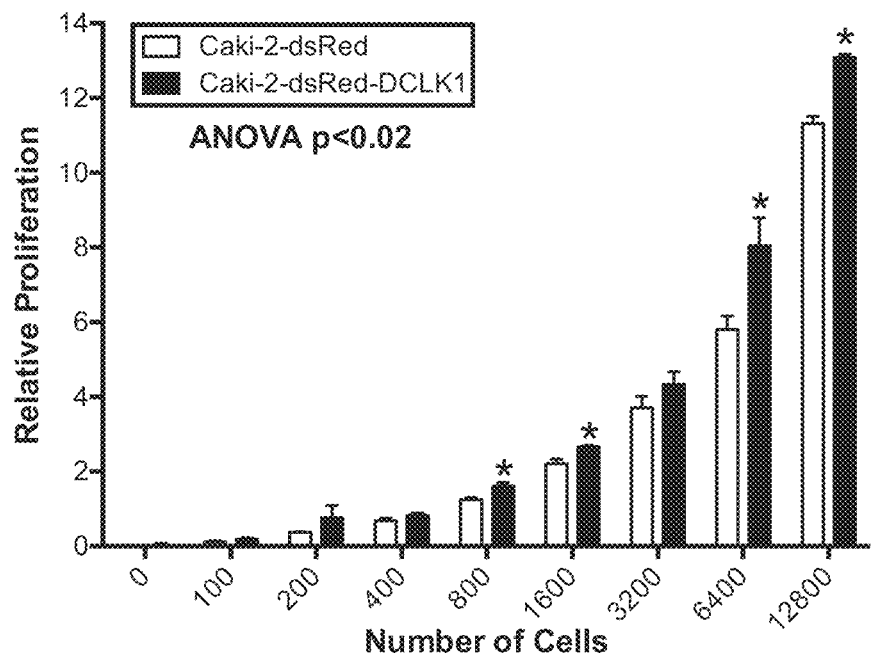
FIG. 6 is a graph showing that overexpression of DCLK1 isoform 2 results in significantly increased Caki-2 cell proliferation.
Figure 7:
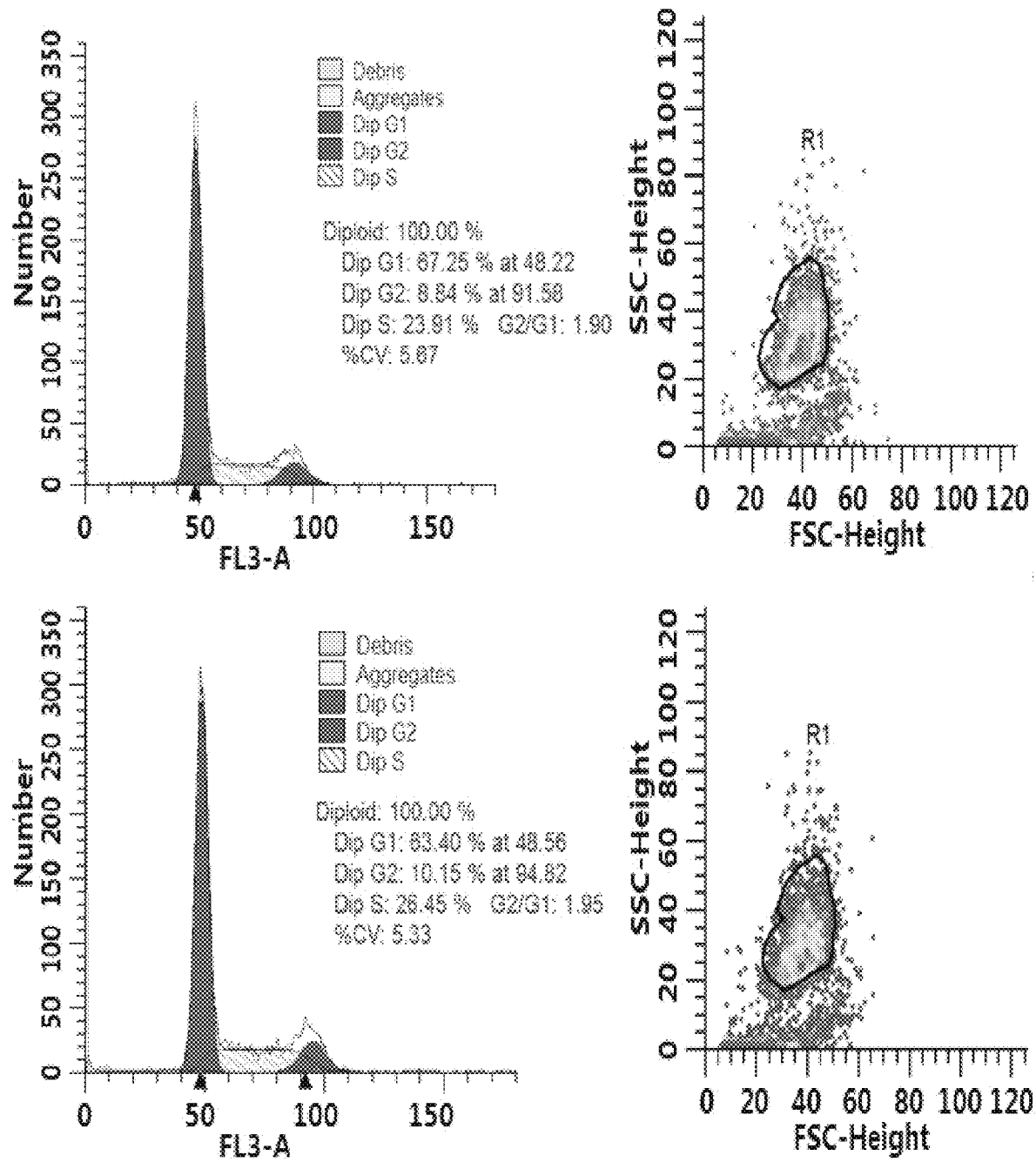
FIG. 7 is a plot showing that overexpression of DCLK1 isoform 2 does not alter Caki-2 cell cycle status.

DCLK1 Overexpression Increases RCC Proliferation but has No Effect on Cell Cycle Dynamics Previous studies directly implicated DCLK1 expression and activity in cell proliferation and cell cycle dynamics in other tumors (Weygant N, Qu D, Berry W L, May R, Chandrakesan P, Owen D B, et al. Small molecule kinase inhibitor LRRK2-IN-1 demonstrates potent activity against colorectal and pancreatic cancer through inhibition of doublecortin-like kinase 1. Molecular cancer. 2014; 13:103; Sureban S M, May R, Weygant N, Qu D, Chandrakesan P, Bannerman-Menson E, et al. XMD8-92 inhibits pancreatic tumor xenograft growth via a DCLK1-dependent mechanism. Cancer letters. 2014; 351(1):151-61). To determine whether overexpression of DCLK1 affects proliferation in RCC, we seeded Caki2-dsRed-DCLK1 and Caki2-dsRed cells in quadruplicate and allowed them to attach and proliferate for 24 h. MTT uptake demonstrated that DCLK1 overexpression significantly increases proliferation (P<0.038) in the Caki-2 cell line (FIG. 6). To determine if overexpression had any effect on RCC cell cycle dynamics, we performed FACS-based cell cycle analysis. We found no notable changes between control and DCLK1-overexpressing cells (FIG. 7). These findings support a role for DCLK1 in cell proliferation consistent with our previous study in RCC (Weygant N, Qu D, May R, Tierney R M, Berry W L, Zhao L, et al. DCLK1 is a broadly dysregulated target against epithelial-mesenchymal transition, focal adhesion, and stemness in clear cell renal carcinoma. Oncotarget. 2015; 6(4):2193-205).

Figure 8A:
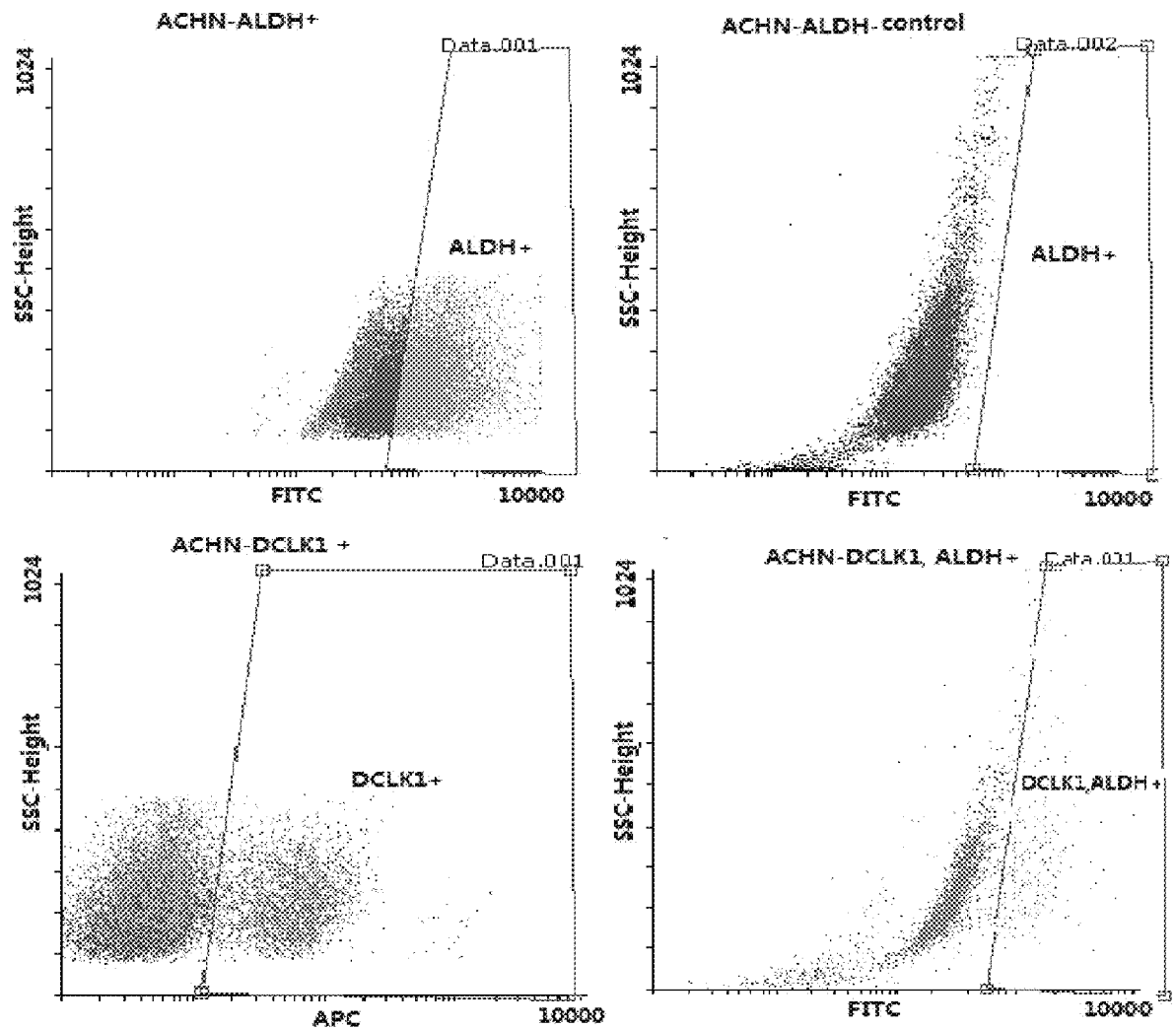
FIG. 8A is a plot showing that a subset of ACHN human renal cancer cells are positive for DCLK1 isoforms 2 or 4 and another subset is positive for ALDH, and that a minority subset (0.5%) of the cell population is positive for both markers.
Figure 8B:
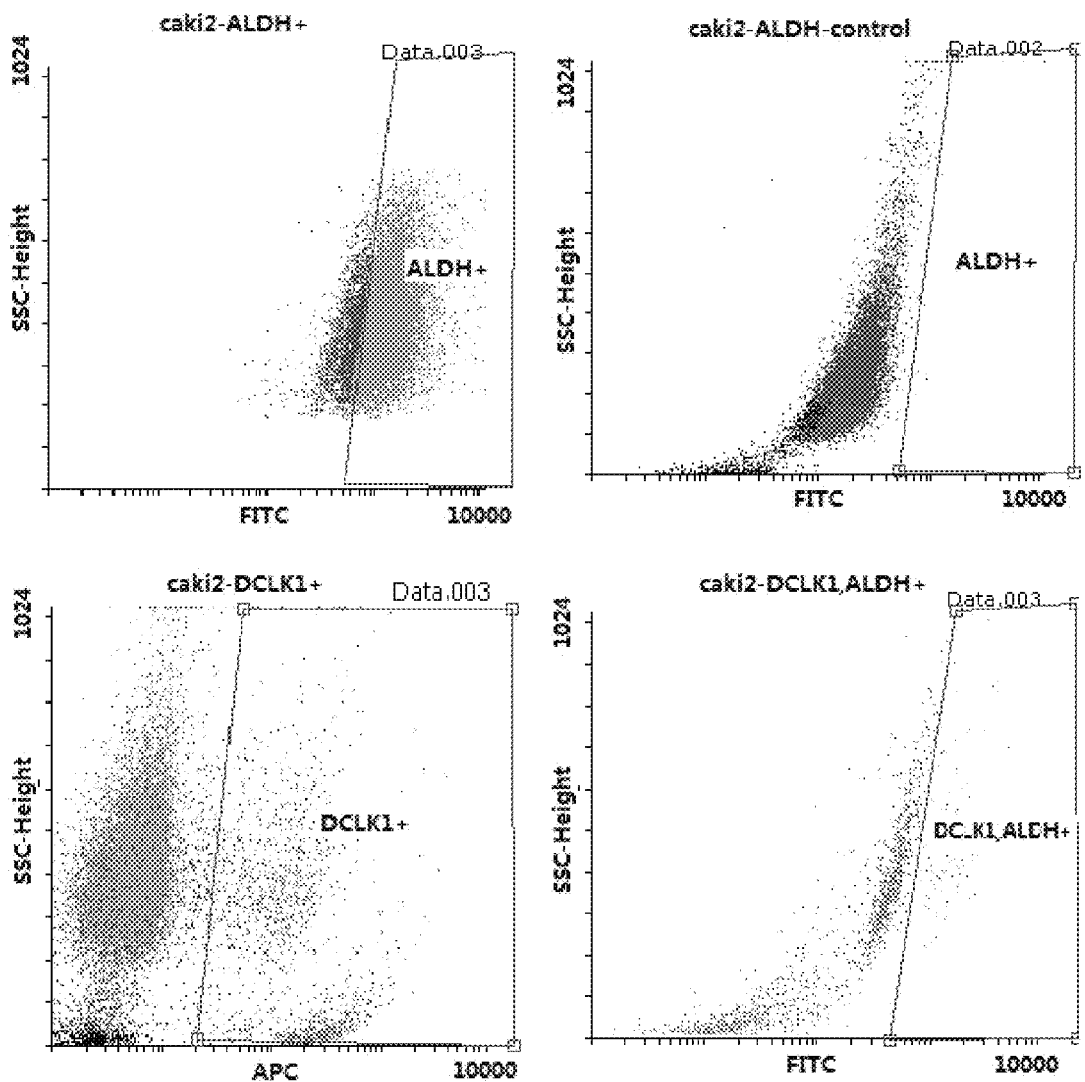
FIG. 8B shows that a subset of Caki-2 human renal cancer cells are positive for DCLK1 isoforms 2 or 4 and another subset is positive for ALDH, and that a minority subset (1.5%) of the cell population is positive for both markers.
Figure 9:
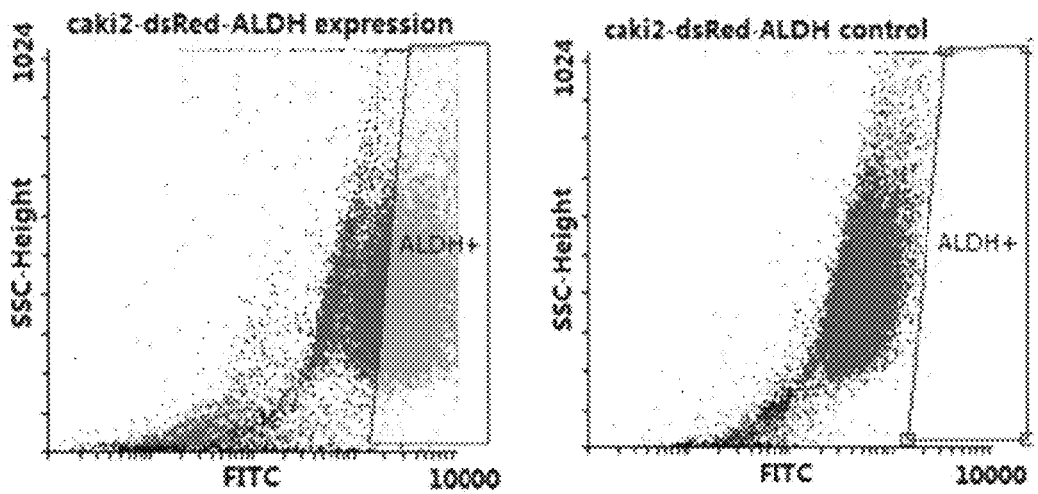
FIG. 9 is a plot showing that overexpression of DCLK1 isoform 2 in Caki-2 human renal cancer cells leads to an increase in the ALDH+ cell population.
Figure 9:
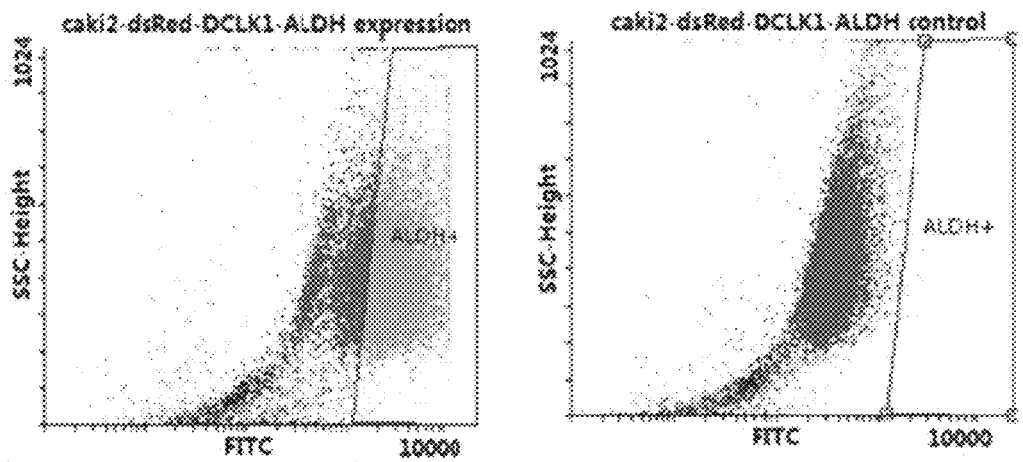

DCLK1 Upregulation in RCC Results in ALDH Cancer Stem Cell Marker Over Expression Given the importance of ALDH in RCC and our findings regarding DCLK1-driven modulation of ALDH expression, we assessed the relationship between these proteins by FACS. Using Aldefluor reagent and DCLK1 antibody we found a large percentage of ALDH+ cells (73.73% in ACHN and 55.12% in Caki-2) and much smaller percentage of DCLK1+ cells (7.47% in ACHN and 17.87% in Caki-2) as well as fractional ALDH/DCLK1 double-positive populations in both Caki-2 (1.51%) and ACHN (0.54%) cell lines (FIGS. 8A-8B). Further FACS analysis demonstrated that DCLK1 overexpression in Caki-2 cells increases the number of ALDH+ cells by approximately 7% (FIG. 9). These findings demonstrate the existence of small subpopulations of ALDH/DCLK1++ cells in renal cancer cell lines and link DCLK1 to both ALDH expression and the propagation of ALDH+ cells.

Figure 10:
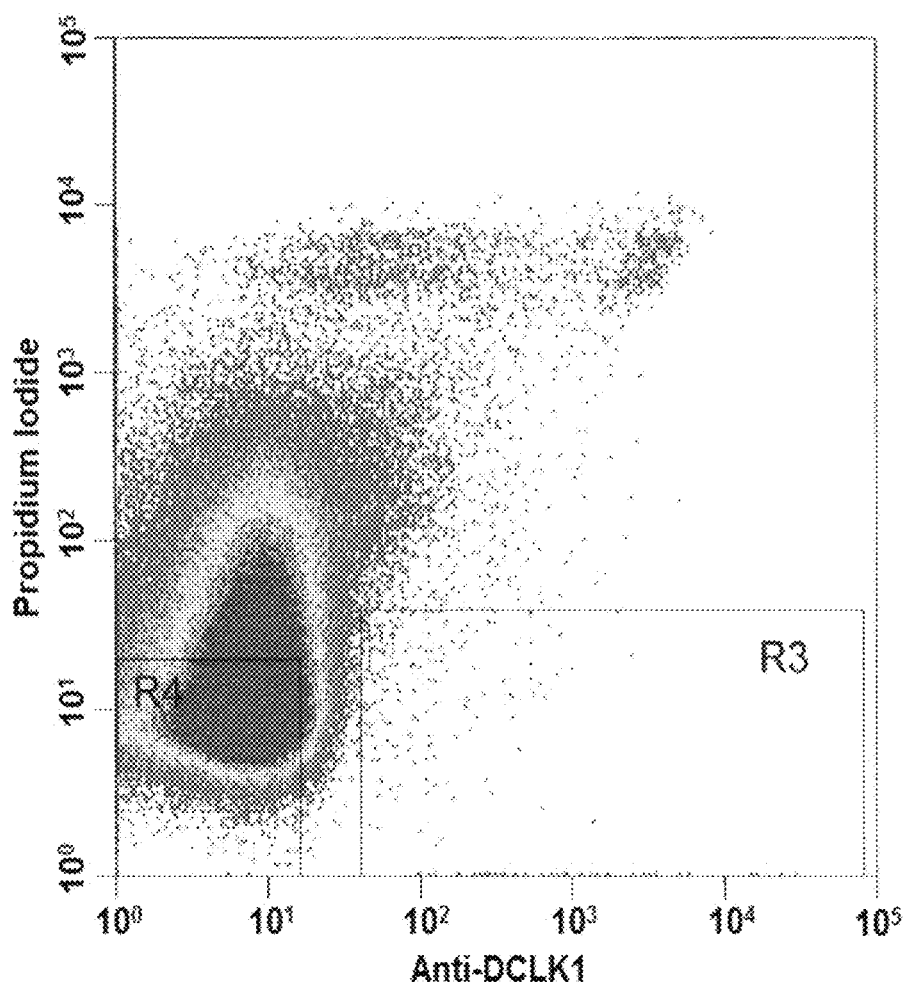
FIG. 10 shows that DCLK1 isoform 2 or 4 is expressed extracellularly in ACHN human renal cancer cells.
Figure 11:
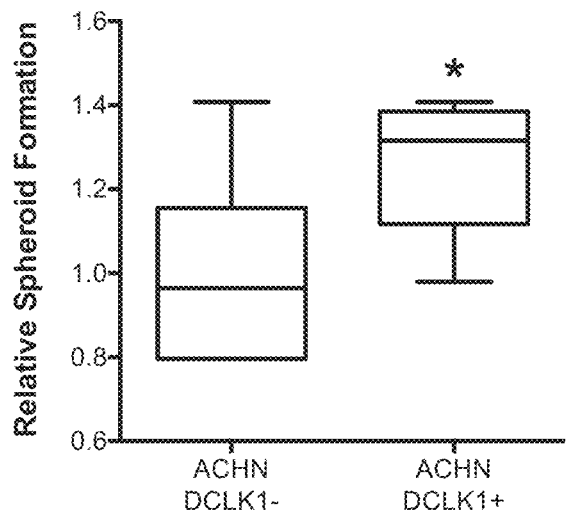
FIG. 11 in a graph showing that ACHN human renal cancer cells with extracellular DCLK1 isoforms 2 or 4 are better able to form spheroids than those without extracellular DCLK1 isoforms 2 or 4.

The ACHN RCC Line Contains an Extracellular DCLK1+ Subpopulation with Increased Clonogenic Capacity Extracellular markers of cancer-stem or stem-like cells are highly desirable for the development of targeted therapies. We hypothesized that some of the minority subpopulation of DCLK1+ cells observed in our FACS experiments might express extracellular DCLK1. To evaluate this hypothesis, we sorted DCLK1+ cells under non-permeabilizing conditions from the ACHN cell line by FACS using fluorophore-conjugated primary antibody targeting the extracellular domain of DCLK1 and fluorophore-conjugated isotype control to exclude cells with non-specific staining (FIG. 10). Following FACS, cells were immediately seeded into extracellular matrix for three-dimensional colony formation assay. Following two weeks of growth, ACHN-DCLK1+ cells formed significantly more spheroids (>25%) compared to ACHN-DCLK1-cells (FIG. 11). This finding demonstrates that extracellular DCLK1 is present in a population of RCC cells with enhanced clonogenic capacity and provides evidence of a role for DCLK1 in supporting RCC stemness and as an RCC stem cell marker.

DCLK1 Expression Regulates Functional Sternness in Renal Cancer Cells

Figure 12:
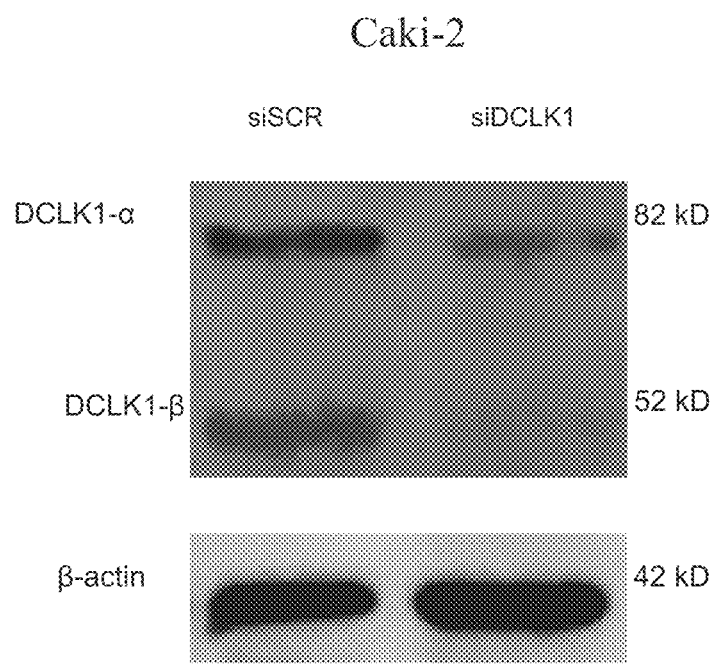
FIG. 12 is a blot confirmation of DCLK1 protein knockdown in Caki-2 human renal cancer cells.
Figure 13:
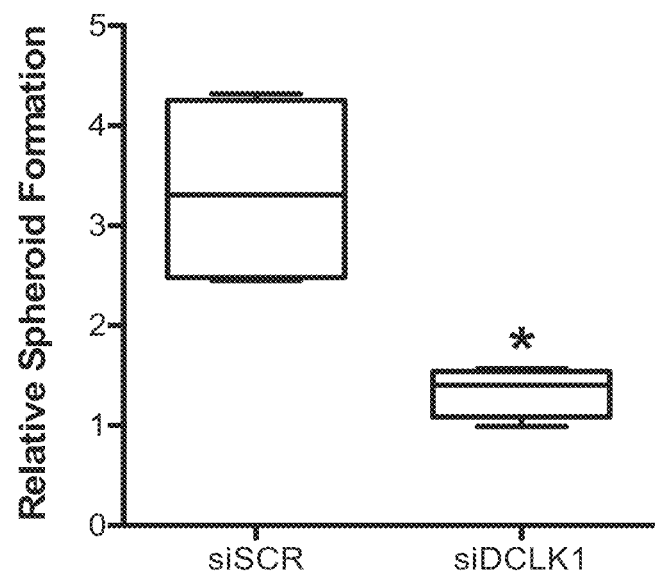
FIG. 13 shows that following DCLK1 knockdown, the ability for Caki-2 human renal cancer cells to form spheroids is significantly impaired.
Figure 13:
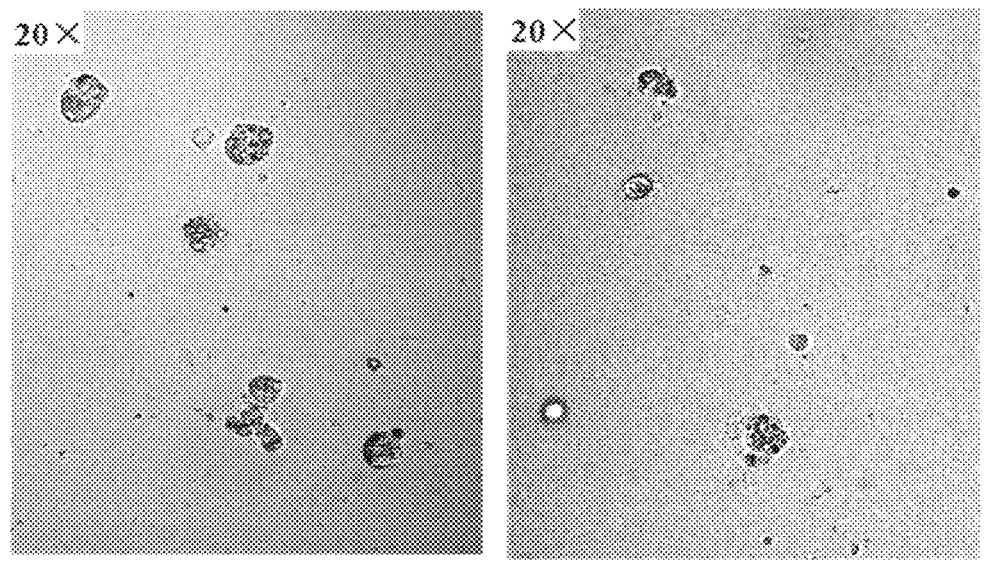
Figure 14:
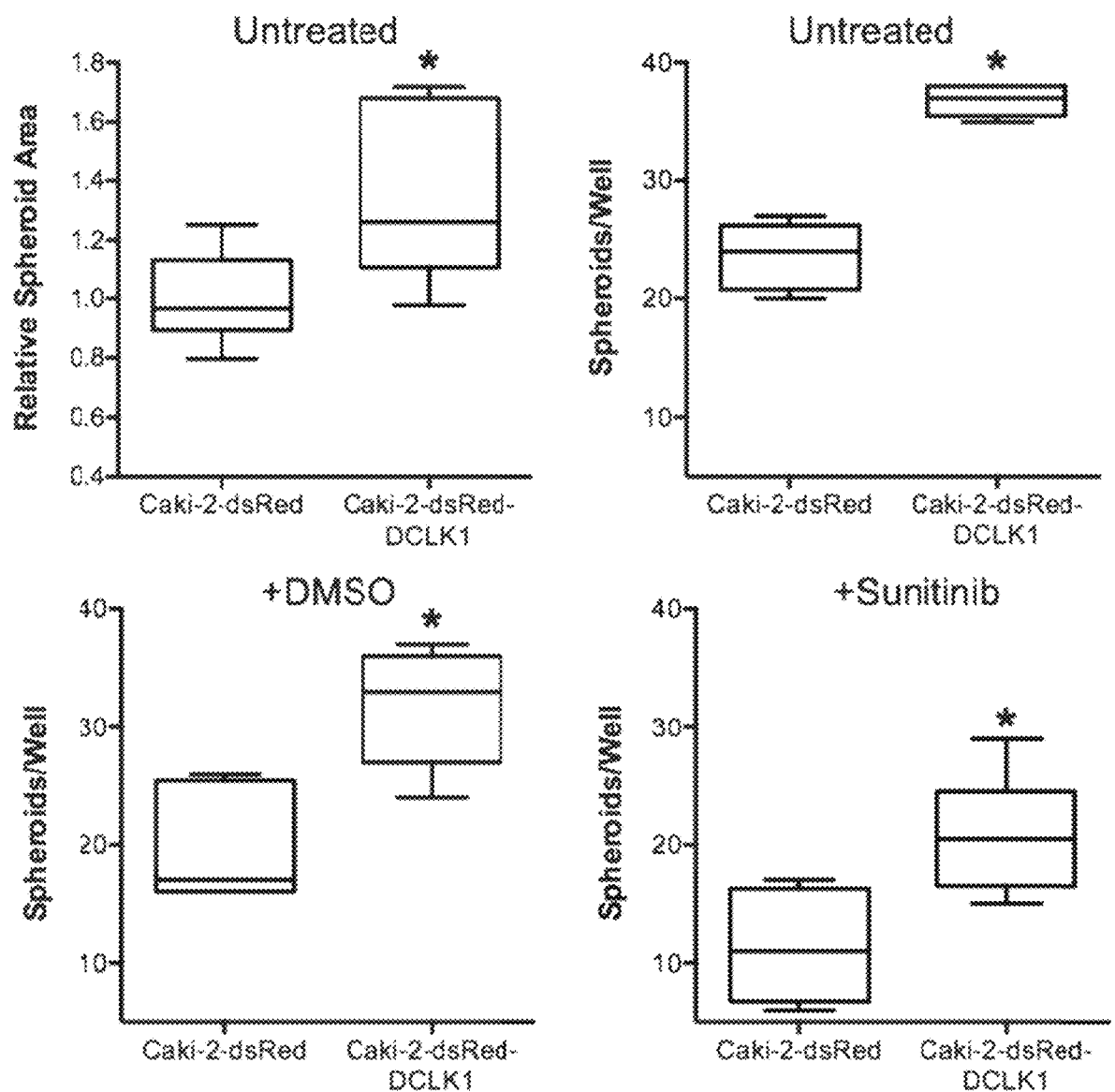
FIG. 14 graphically shows that sunitinib pretreatment of Caki-2 human renal cancer cells overexpressing DCLK1 isoform 2 only slightly impacts the cells' ability to form spheroids.
Figure 15:
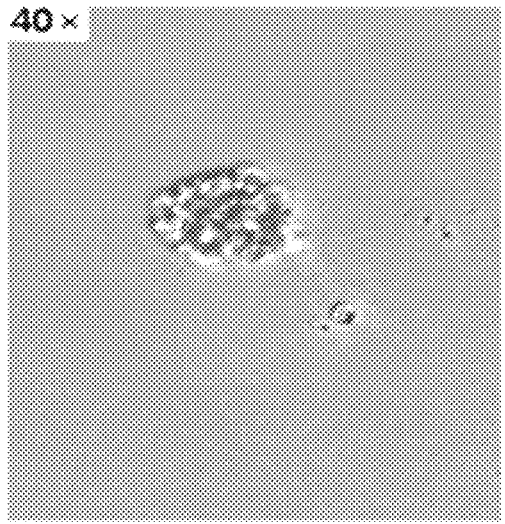
FIG. 15 shows representative micrographic images of control or DCLK1 isoform 2-overexpressing Caki-2 spheroids.
Figure 15:
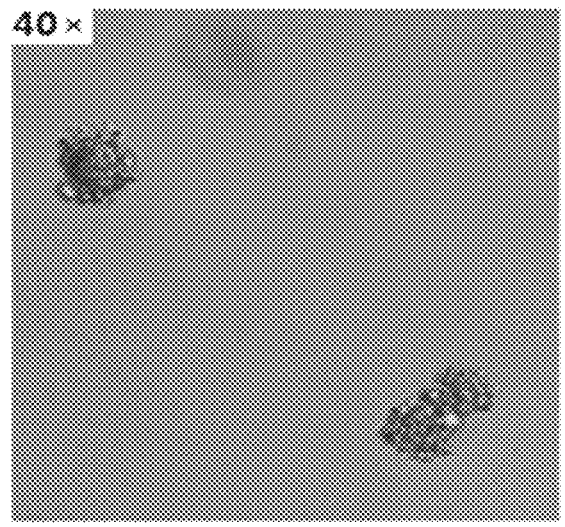
Figure 15:
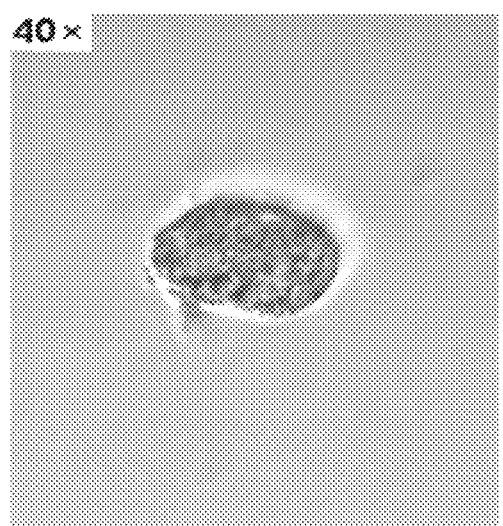
Figure 15:
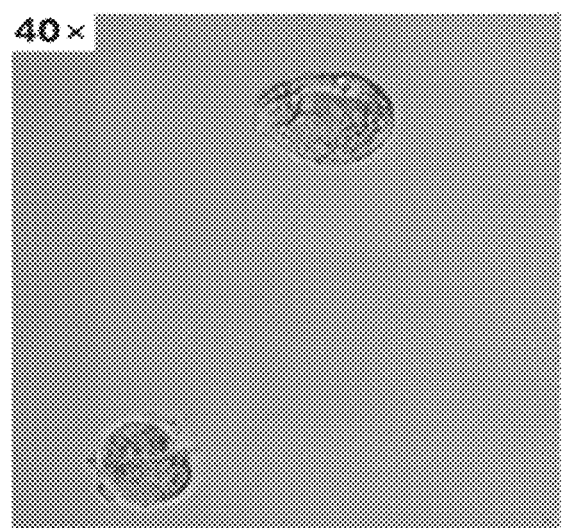

Spheroid and colony formation capacity in response to drug treatment is a distinct characteristic of stem cells or stem-like cells. We previously reported that targeting DCLK1 with siRNA can inhibit three-dimensional colony formation in RCC. To expand on these findings we knocked down DCLK1 expression in the Caki-2 cell line using specific siRNAs against DCLK1 (siDCLK1) or scrambled sequence siRNA with no target (siSCR) for 72 h. After confirming successful DCLK1 knockdown (FIG. 12), the cells were subjected to 72 h treatment with 0.5 µM sunitinib and assessed for viability by trypan blue exclusion. The cells were then seeded into growth-factor reduced matrigel to assess colony formation ability following drug treatment. We observed a >50% decrease in the number of spheroids formed in Caki-2 cells (FIG. 13) treated with siDCLK1 compared to siSCR following 2 weeks of colony formation. To further assess DCLK1's role in RCC functional sternness, three-dimensional colony formation assay was performed with Caki-2-dsRed-DCLK1 and Caki2-dsRed cells either untreated or treated with DMSO or 0.5 µM sunitinib for 72 h as described above. Following 2 weeks of growth there was a dramatic increase in the number of colonies formed from the DCLK1-overexpressing cells in all three groups (FIG. 14). Using image-processing technology to assess spheroid area as previously described (Weygant N, Qu D, May R, Tierney R M, Berry W L, Zhao L, et al. DCLK1 is a broadly dysregulated target against epithelial-mesenchymal transition, focal adhesion, and sternness in clear cell renal carcinoma. Oncotarget. 2015; 6(4):2193-205), we found a significant increase in the mean size of three-dimensional colonies in DCLK1-overexpressing cells (FIG. 15). Immunostaining of the untreated spheroids revealed strong expression of ALDH in colonies formed from Caki-2-dsRed-DCLK1 cells but faint to low level expression in those formed from Caki-2-dsRed control cells, as predicted by our earlier FACs studies. Together these findings demonstrate that DCLK1 is an important regulator of RCC anchorage-independent growth, colony formation and self-renewal ability. Furthermore, these findings support a role of DCLK1 as a marker and regulator of stem-like cells in RCC.

Figure 16:
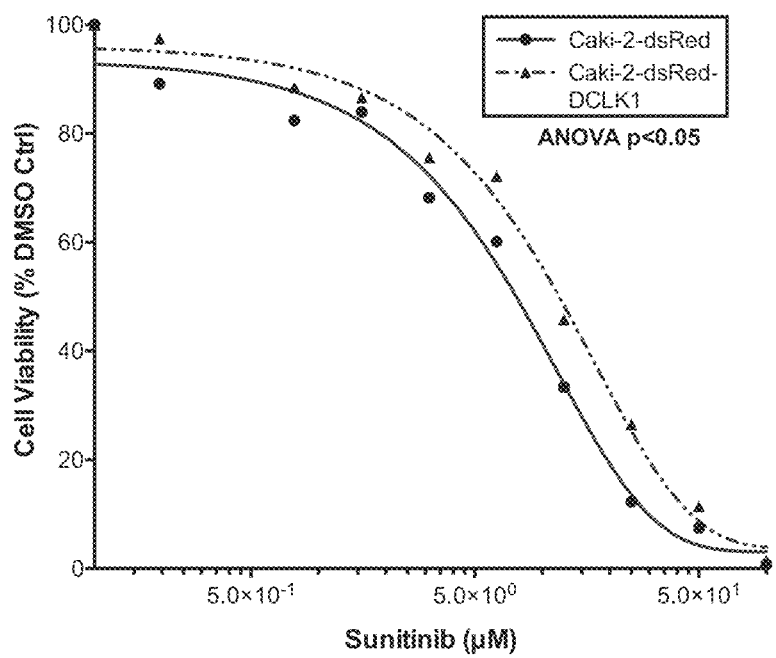
FIG. 16 is a graph showing that DCLK1 isoform 2-overexpressing Caki-2 cells are resistant to sunitinib.
Figure 17:
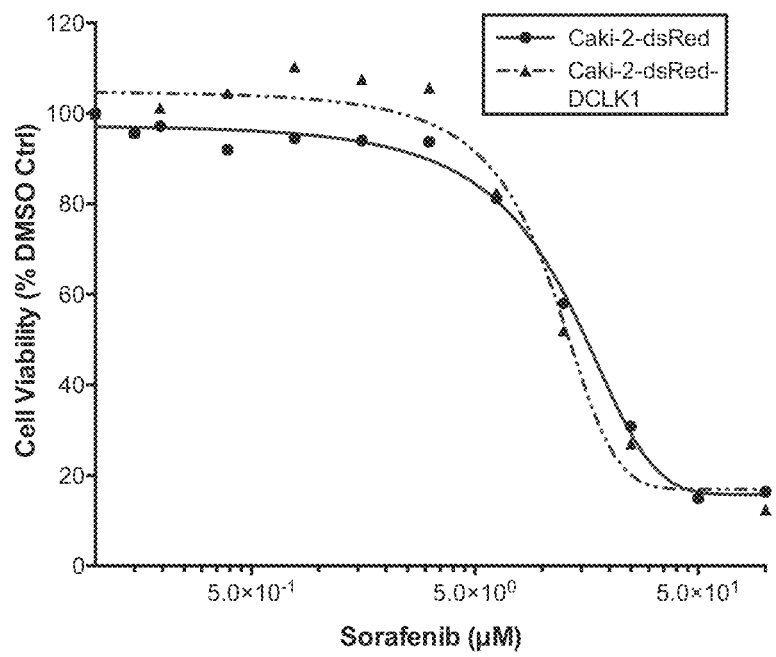
FIG. 17 is a graph showing that DCLK1 isoform 2-overexpressing Caki-2 cells are not resistant to sorafenib.
Figure 18:
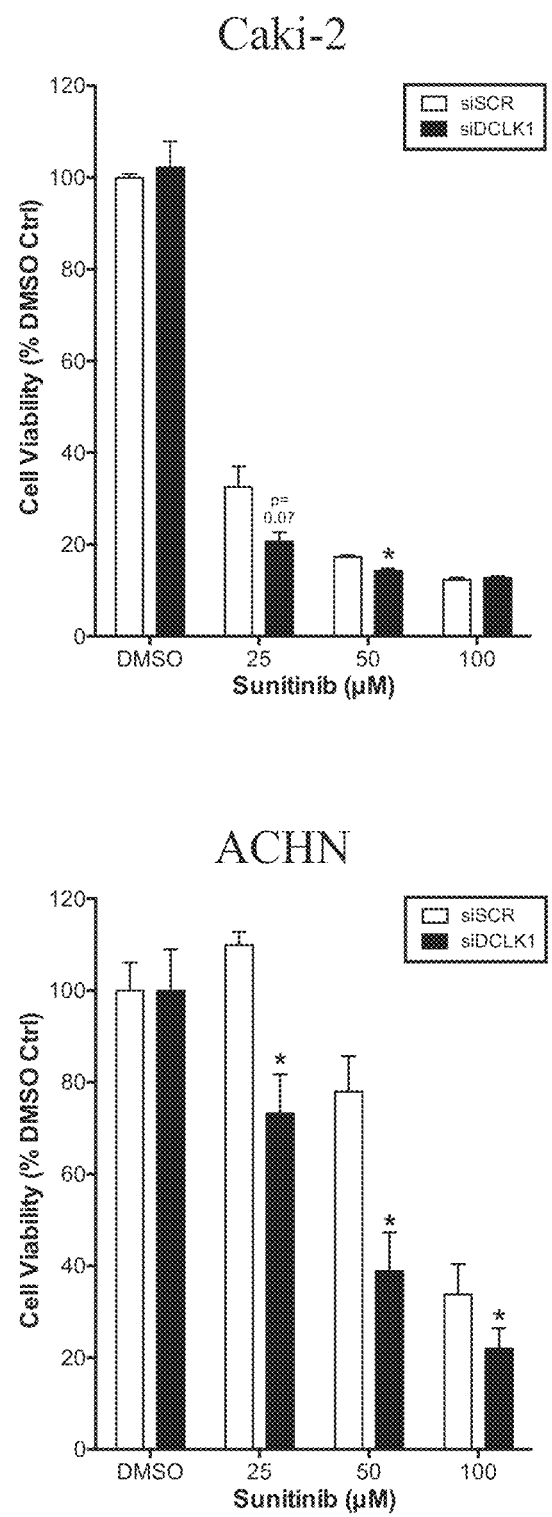
FIG. 18 is a graph showing that downregulation of DCLK1 with anti-DCLK1 siRNA (siDCLK1) and scrambled sequence siRNA (siSCR) results in sensitization to sunitnib in Caki-2 and ACHN human renal cancer cells.
Figure 19:
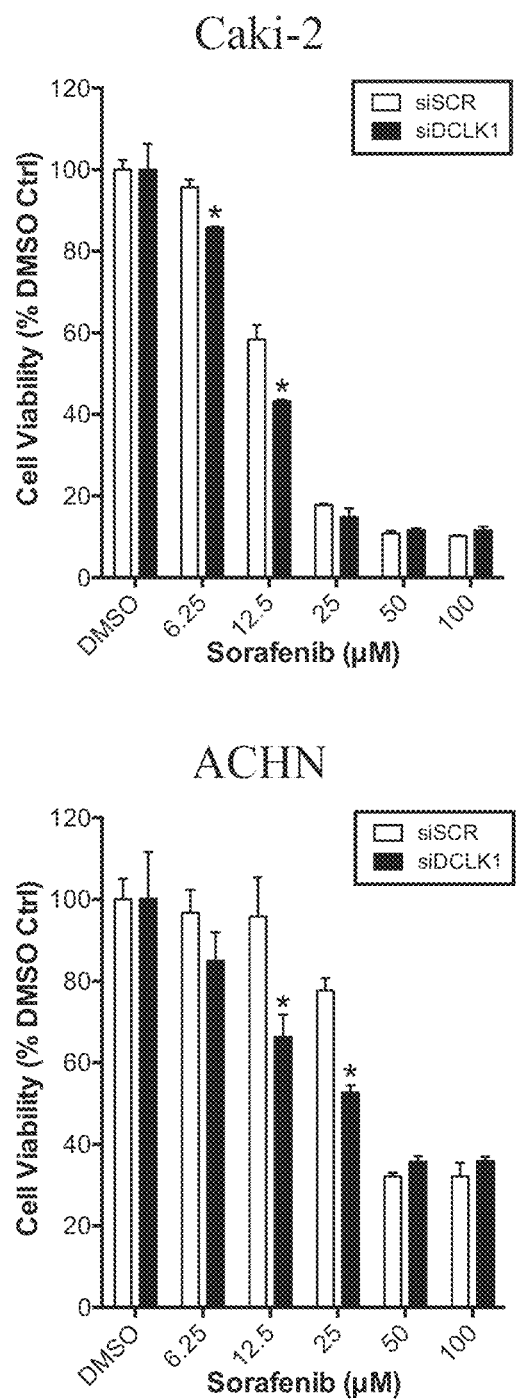
FIG. 19 shows that downregulation of DCLK1 anti-DCLK1 siRNA (siDCLK1) and scrambled sequence siRNA (siSCR) results in sensitization to sorafenib in Caki-2 and ACHN human renal cancer cells.

DCLK1 Modulates the Response of RCC Cells to FDA-Approved RTK and mTOR Inhibitors The high level of expression of vascular endothelial growth factor (VEGF) and its receptors in RCC supports its highly vascular nature making VEGF and its receptors therapeutic targets. Currently, sunitinib and sorafenib, small molecule inhibitors of receptor tyrosine kinases (RTKs), have been approved by the FDA for advanced RCC. We previously showed preliminary evidence suggesting that DCLK1 may be an important factor in regulating the response to RTK inhibitors in RCC (Weygant N, Qu D, May R, Tierney R M, Berry W L, Zhao L, et al. DCLK1 is a broadly dysregulated target against epithelial-mesenchymal transition, focal adhesion, and sternness in clear cell renal carcinoma. Oncotarget. 2015; 6(4):2193-205). Given the tight relationship between sternness and the response to targeted therapies and its importance in patient survival, we further investigated DCLK1's role in this process. Caki-2 cells overexpressing DCLK1 were seeded into 96-well plates, allowed to attach overnight, and then treated with increasing concentrations of sunitinib or sorafenib. Relative cell viability was then evaluated by MTT assay. We found that overexpressing DCLK1 significantly decreased the sensitivity of Caki-2 cells to sunitinib (FIG. 16), but did not elicit significant resistance to sorafenib compared to dsRed vector control cells (FIG. 17). In contrast, ACHN and Caki-2 cells pre-treated with 25 nM siDCLK1 for 72 h were remarkably sensitized to both sunitinib and sorafenib compared to siSCR controls (FIGS. 18-19).

The intracellular serine/threonine kinase mTOR is involved in a wide range of pathways and plays an essential role in cellular metabolism and cancer progression. Several mTOR inhibitors such as everolimus and temsirolimus have been approved as treatment for some cancers including advanced kidney cancer. Since the expression of DCLK1 regulates cell survival in response to RTK inhibitors, we then investigated whether overexpressing DCLK1 desensitizes RCC to mTOR inhibitors. Following the same protocol as above, we found that overexpression of DCLK1 in Caki-2 cells significantly decreases sensitivity to everolimus and temsirolimus. These results illustrate that DCLK1 regulates resistance to the major types of FDA-approved inhibitors in RCC, and that RCCs expressing high levels of DCLK1 may be more susceptible to sorafenib than sunitinib. Finally, these findings suggest that targeting DCLK1 may improve RCC patients' response to currently approved drugs.

DCLK1 and PD-L1 are Co-Expressed in RCC Tumors

Figure 20:
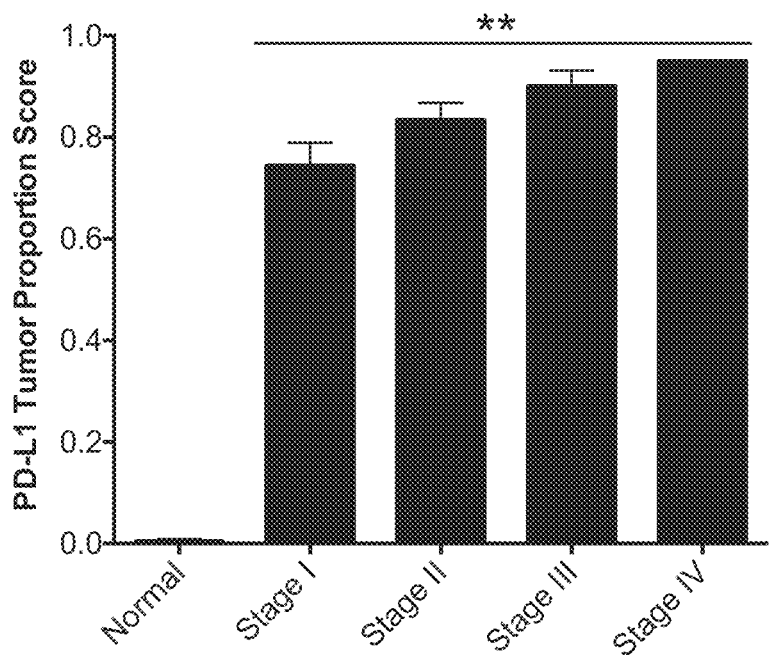
FIG. 20 is a graph showing that programmed death-ligand 1 (PD-L1) expression is associated with renal cancer stage in patient tumor tissue.
Figure 21:
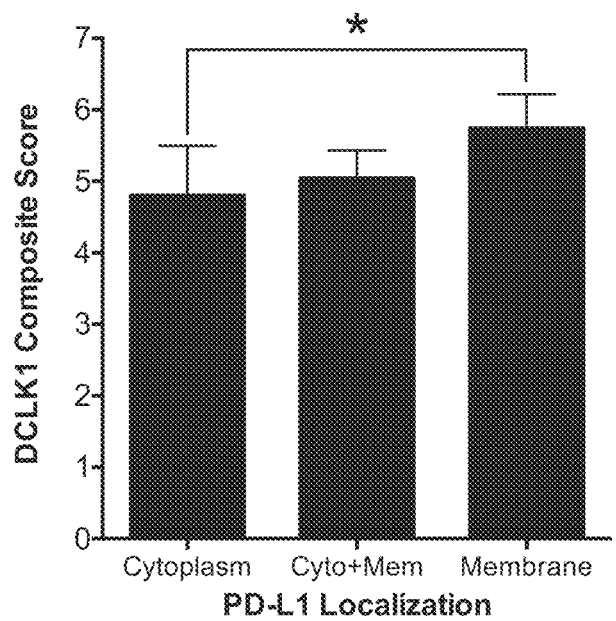
FIG. 21 shows that DCLK1 expression is associated with the expression of membrane PD-L1 in renal cancer tissue from patients.

Programmed death-ligand-1 (PD-L1/CD274) is an immune checkpoint marker known to be expressed on the cell surface of various tumors, including kidney cancer. Its expression negatively regulates the immune response by binding to its receptor, programmed death-1 (PD-1) on tumor specific T cells leading to cell apoptosis and allowing tumor cells to escape from cytolysis induced by activated T cells. While kidney cancer responds poorly to chemotherapy and radiotherapy, studies focusing on immunotherapeutic and immune check point strategies, including the PD-L1/PD-1 interaction have shown promising results (Sznol M, Chen L. Antagonist antibodies to PD-1 and B7-H1 (PD-L1) in the treatment of advanced human cancer. Clinical cancer research: an official journal of the American Association for Cancer Research. 2013; 19(5):1021-34; Pardoll D M. The blockade of immune checkpoints in cancer immunotherapy. Nature reviews Cancer. 2012; 12(4):252-64; Brahmer J R, Tykodi S S, Chow L Q, Hwu W J, Topalian S L, Hwu P, et al. Safety and activity of anti-PD-L1 antibody in patients with advanced cancer. The New England journal of medicine. 2012; 366(26):2455-65; Topalian S L, Drake C G, Pardoll D M. Targeting the PD-1/B7-H1(PD-L1) pathway to activate anti-tumor immunity. Current opinion in immunology. 2012; 24(2):207-12). In order to determine if DCLK1 and PD-L1 are co-expressed in RCC, we performed immunohistochemistry using a high-density tissue microarray and had the results quantified by experienced pathologists. PD-L1 was strongly upregulated in RCC in a stage dependent fashion similar to what we have previously reported for DCLK1(19) (FIG. 20). Moreover, we found that tumors with membrane-localized PD-L1 demonstrated significantly higher DCLK1 expression levels compared to tumors with cytoplasmic PD-L1 (FIG. 21).

Figure 22:
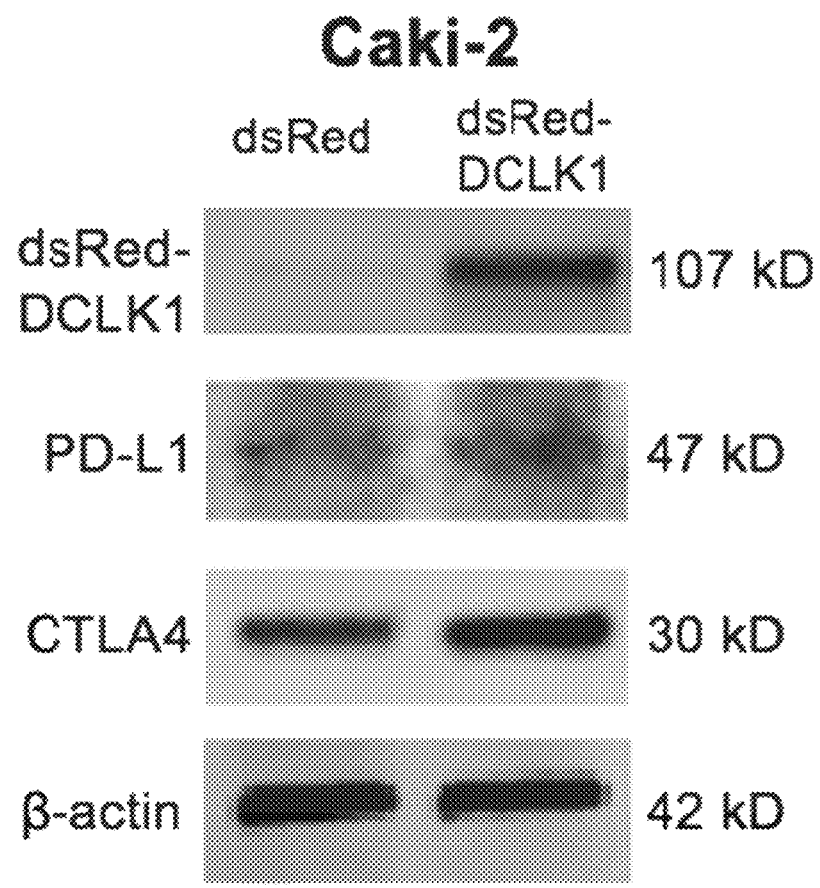
FIG. 22 is a blot showing that overexpression of DCLK1 isoform 2 in Caki-2 human renal cancer cells leads to overexpression of immune checkpoint markers PD-L1 and cytotoxic T-lymphocyte-associated protein 4 (CTLA4).
Figure 23:
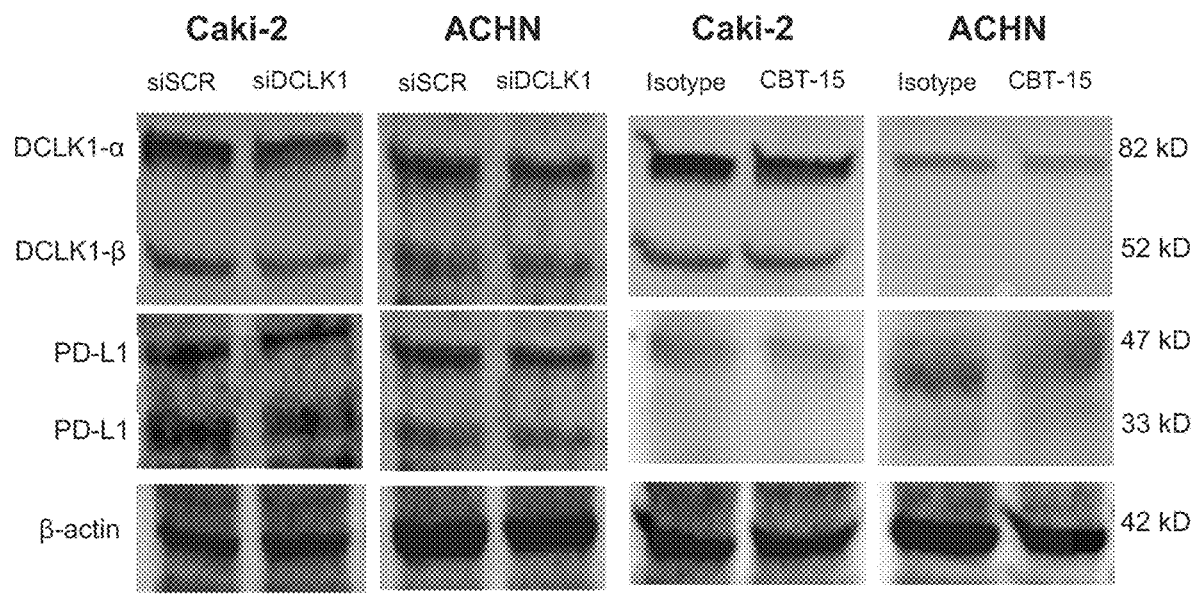
FIG. 23 is a series of western blots showing that DCLK1 siRNA or CBT-15A antibody partially downregulate PD-L1 expression in Caki-2 and ACHN human renal cancer cells.

Targeting DCLK1 Inhibits Immune Checkpoint in RCC Cells Leading to Increased PBMC-Driven Apoptosis Given our tissue microarray data, the hypothesized link between immune checkpoint and cancer stem cells, and emerging data linking immune checkpoint to the EMT-phenotype supported by DCLK1, we evaluated whether targeted DCLK1 knockdown may sensitize RCC to immunotherapy. In these experiments, overexpression of DCLK1 upregulated PD-L1 by >2 fold and CTLA4 >1.5 fold in Caki-2 cells (FIG. 22). In contrast, targeting DCLK1 with 72 h treatment of 25 nM siRNA or 100 μg/mL of monoclonal antibody CBT-15A significantly decreased protein level expression of PD-L1 (FIG. 23) but had no effect on CTLA4 (data not shown) in ACHN and Caki-2 RCC cells.

Figure 24A:
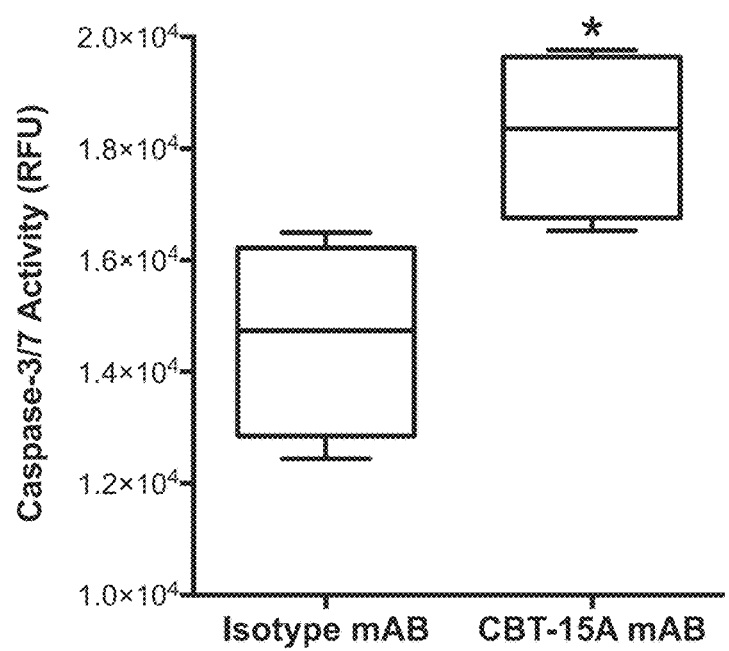
FIG. 24A shows that CBT-15A mAB treatment sensitizes ACHN renal cell carcinoma (RCC) cells to peripheral blood mononuclear cell (PBMC) mediated apoptosis as measured by caspase-3/7 activity.
Figure 24B:
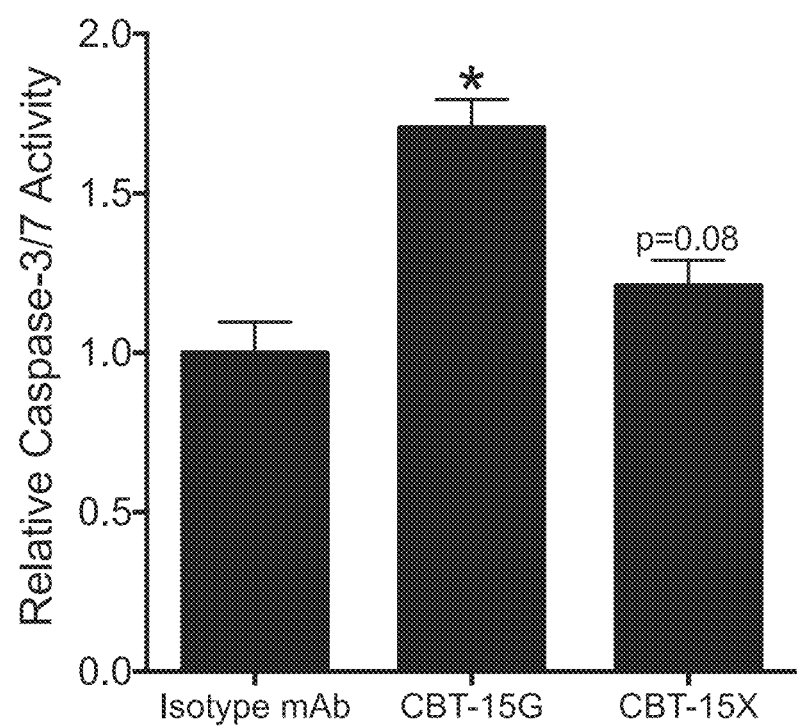
FIG. 24B is a graph showing that CBT-15G and CBT-15X mABs increase immune cell mediated cell killing in vitro in pancreatic cancer cells as measured by caspase-3/7 activity.

To further assess the functional relevance of these findings we seeded ACHN renal and AsPC-1 pancreatic cancer cells into 96 wells and subjected them to antibody-dependent cell-mediated cytotoxicity assay. Briefly, $10^4$ cancer cells were seeded into each well after 48 hours pretreatment with either isotype control or CBT-15 monoclonal antibody. Human peripheral blood monocytes were then seeded into each well at $10^5$ cells per well and co-cultured for 72 h. After 72 h Caspase-3/7 Glo assay was performed to assess apoptosis. Relative to control treatment, Caspase-3/7 activity was significantly increased in CBT-15A treated renal cancer cells and CBT-15G treated pancreatic cancer cells, and also increased in CBT-15X treated pancreatic cancer cells (FIGS. 24A-24B). These findings demonstrated the potential for DCLK1-targeted monoclonal antibodies to be utilized as immunotherapy against renal and pancreatic cancer.

CBT-15 DCLK1-Targeted Antibodies can be Used as Immunotherapy Against Cancer

To demonstrate the efficacy of CBT-15 monoclonal antibodies, tumor xenografts were established from human renal adenocarcinoma (ACHN) and human pancreatic adenocarcinoma (SW1990 and AsPC-1) cell lines. $0.5 \times 10^6$ cells were injected into the flanks of 8 week-old athymic nude mice and the resulting tumors were allowed to grow to an average volume 100 mm$^3$. Upon reaching this volume we began delivering CBT-15 or isotype control mAB at 25 mg/kg biweekly. Tumor volume measurements were taken approximately every other day. At the end of 4 weeks from the start of injections animals were culled and tumors were excised, measured, and weighed.

Figure 25:
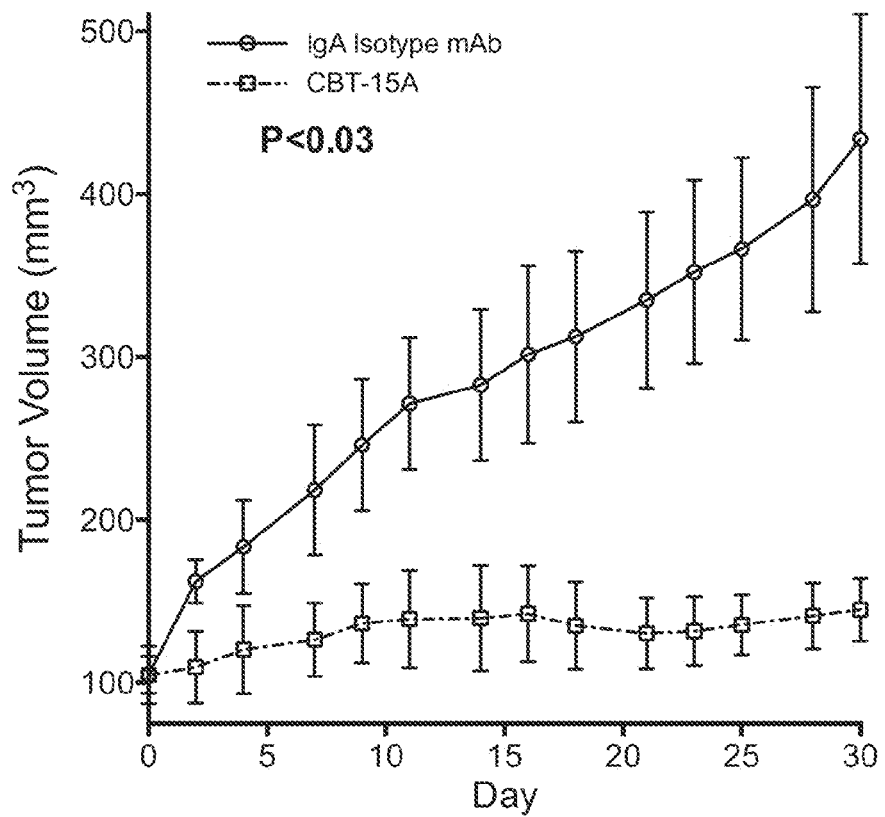
FIG. 25 demonstrates the inhibitory effect of CBT-15A mAB on ACHN human renal tumor xenograft growth in mice (p<0.03). Graph shows tumor volume growth over time. Lower panel shows photographs of the excised renal tumor xenografts which were used to measure tumor volume. CBT-15A mAB substantially reduced tumor growth.
Figure 25:
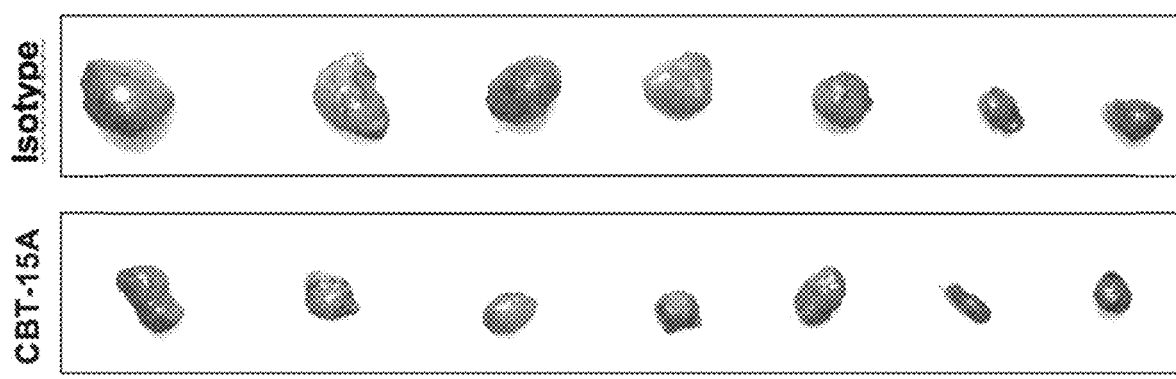
Figure 26:
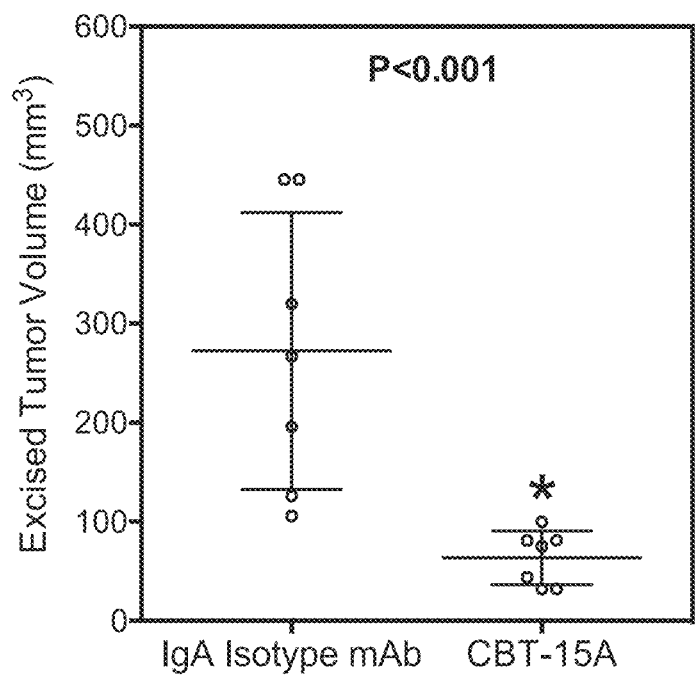
FIG. 26 shows tumor volume of excised tumors of FIG. 25 (p<0.001).
Figure 27:
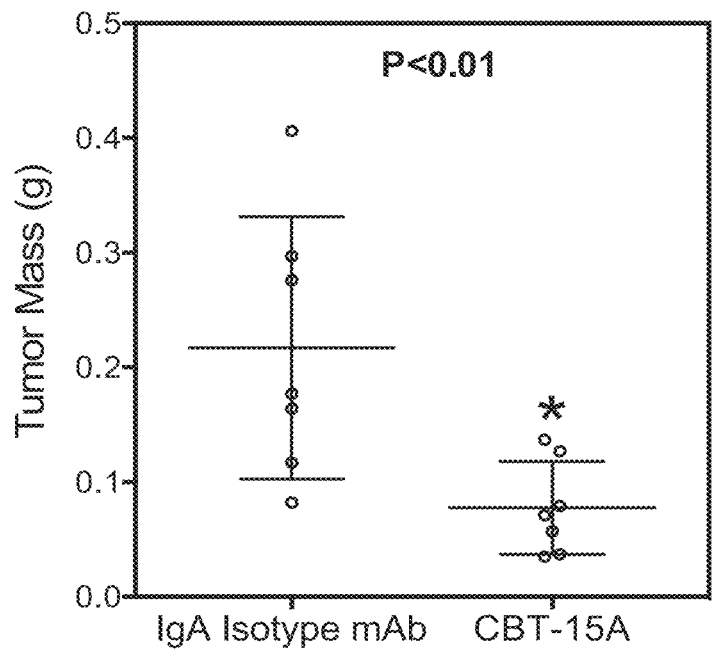
FIG. 27 shows tumor mass of excised tumors of FIG. 25 (p<0.001).

Treatment with CBT-15A mAb strongly inhibited kidney cancer ACHN xenograft growth compared to isotype mAB (FIG. 25; p<0.03). This was confirmed by measuring excised tumor volumes (FIG. 26; p<0.001) and weights (FIG. 27; p<0.01) at the end of treatment. CBT-15A mAb caused a significant decrease in excised tumor volume and tumor weight These findings demonstrate, for the first time, the potent in vivo efficacy of DCLK1-targeted agents against renal cancer.

Figure 28:
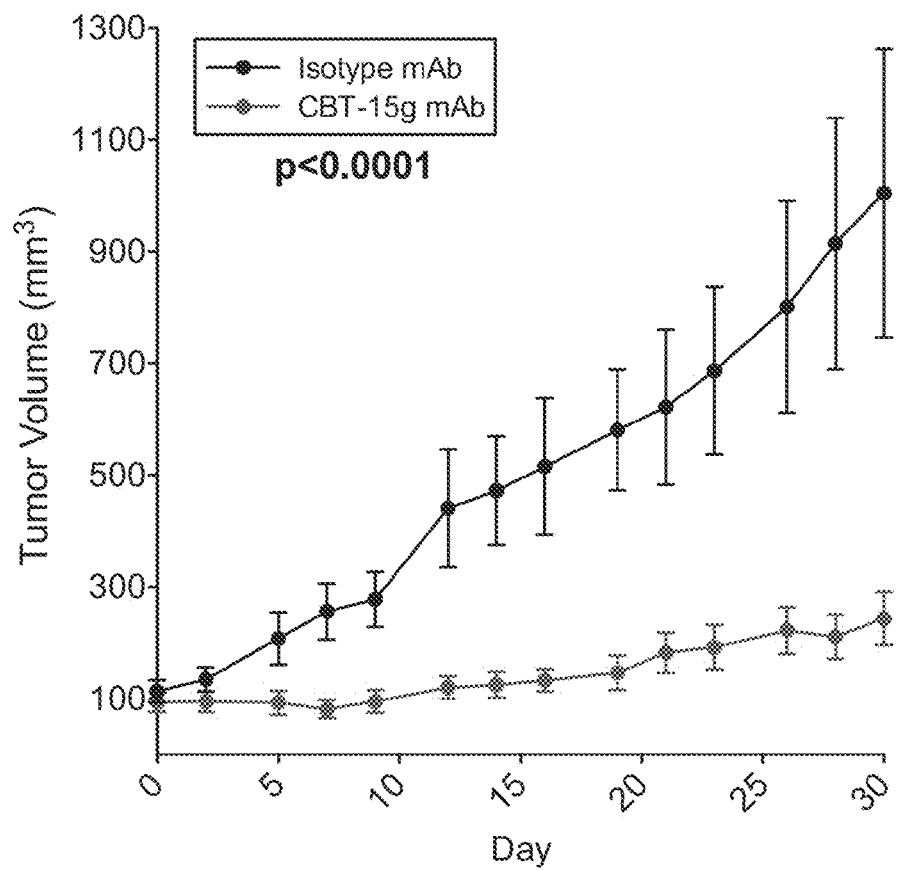
FIG. 28 demonstrates the inhibitory effect of CBT-15G mAB on pancreatic cancer SW1990 tumor xenograft growth in mice (p<0.0001). Graph shows tumor volume growth over time. Lower panel shows photographs of excised renal tumor xenografts. CBT-15G mAB substantially reduced tumor growth.
Figure 28:
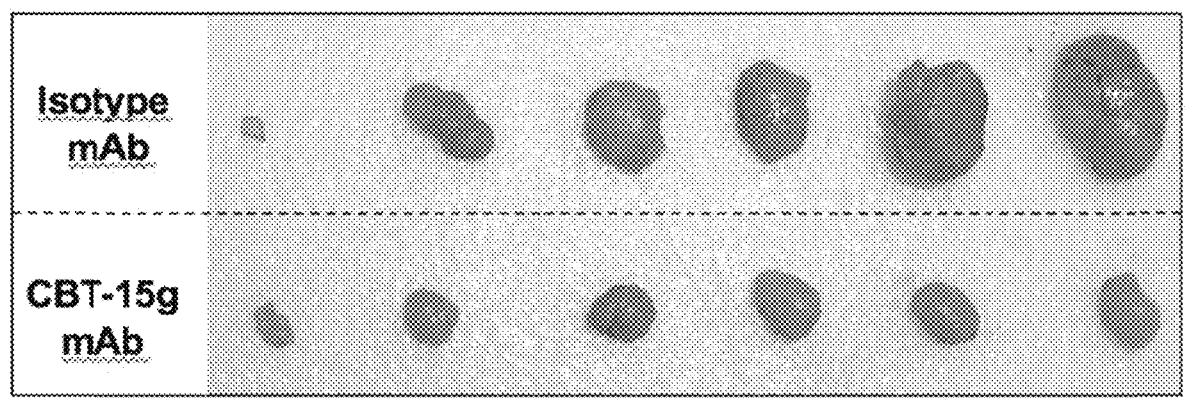
Figure 29:
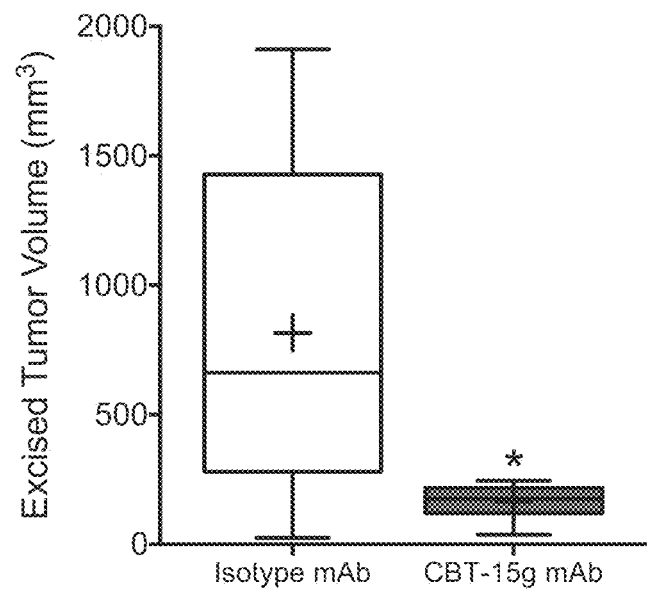
FIG. 29 shows tumor volume of excised tumors of FIG. 28 (p<0.001).
Figure 30:
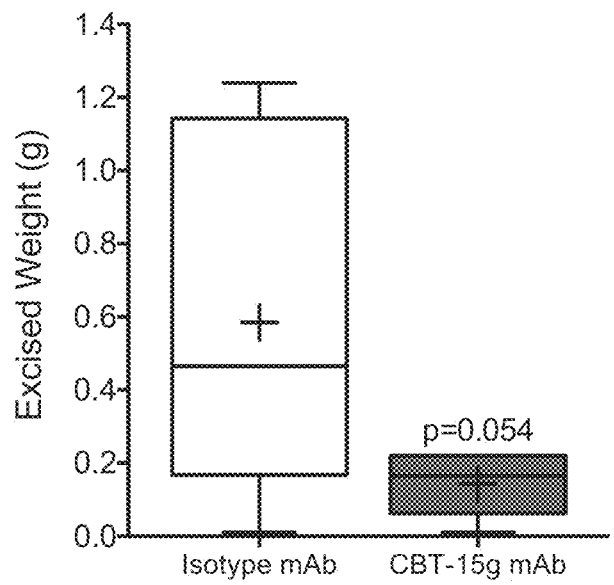
FIG. 30 shows tumor mass of excised tumors of FIG. 28 (p<0.054).

Treatment with CBT-15G mAb strongly inhibited pancreatic cancer SW1990 xenograft tumorigenesis resulting in a significant decrease in excised tumor volume and a decrease in tumor weight (FIGS. 28-30).

Figure 31:
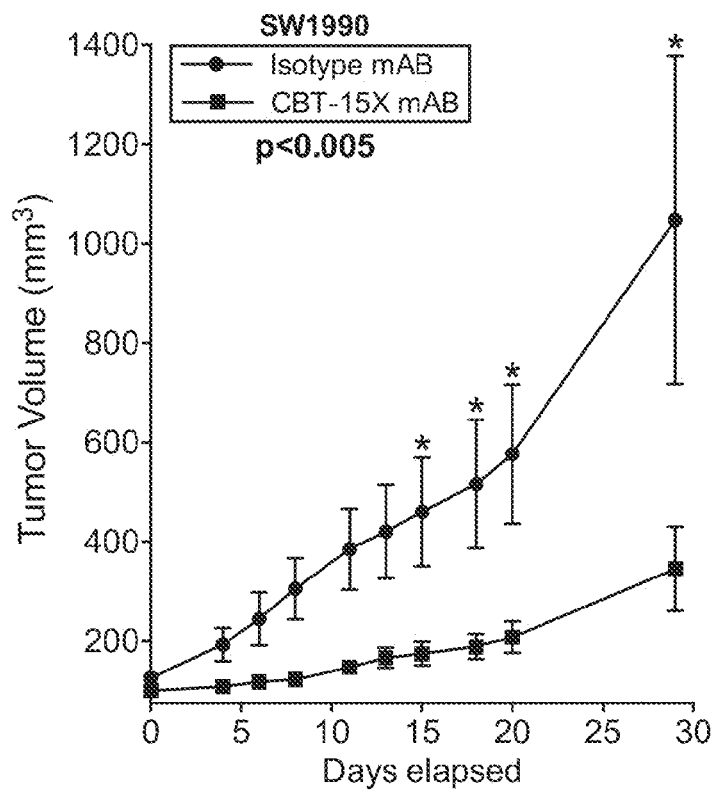
FIG. 31 demonstrates the inhibitory effect of chimeric CBT-15X mAB on pancreatic cancer SW1990 tumor xenograft growth in mice (p<0.005). Graph shows tumor volume growth over time. Lower panel shows photographs of excised renal tumor xenografts. CBT-15X mAB substantially reduced tumor growth.
Figure 31:
Figure 32:
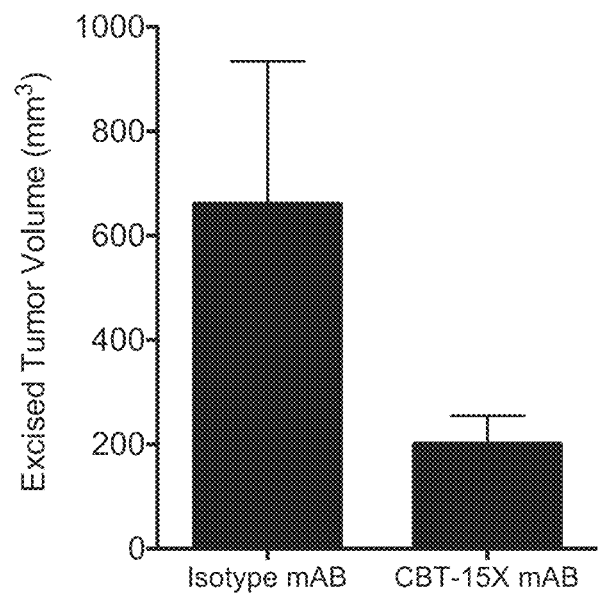
FIG. 32 is a graph showing tumor volume of excised tumors of FIG. 31 (p<0.05).
Figure 33:
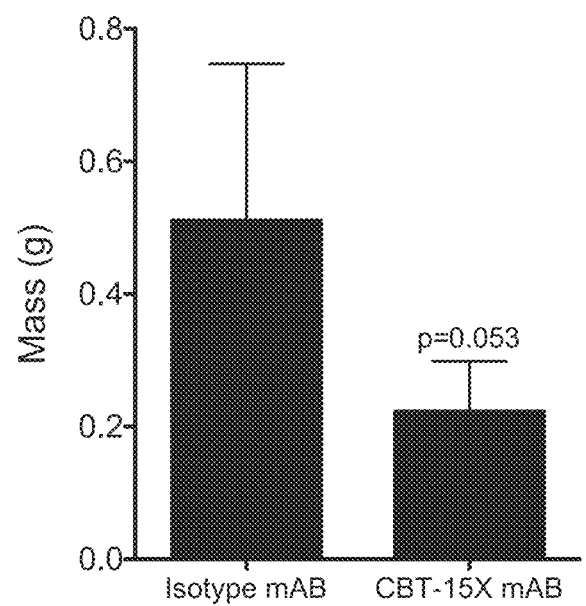
FIG. 33 is a graph showing tumor mass of excised tumors of FIG. 31 (p<0.05).

Treatment with CBT-15X mAb strongly inhibited pancreatic cancer SW1990 xenograft tumorigenesis resulting in a significant decrease in excised tumor volume and a decrease in tumor weight (FIGS. 31-33).

Figure 34:
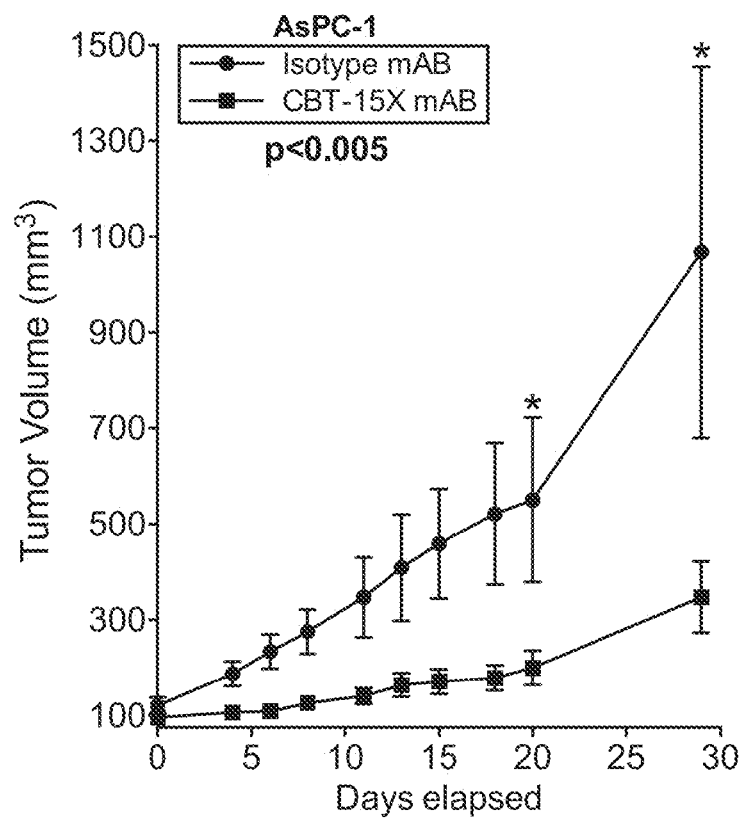
FIG. 34 demonstrates the inhibitory effect of chimeric CBT-15X mAB on pancreatic cancer AsPC-1 tumor xenograft growth in mice (p<0.005). Graph shows tumor volume growth over time. Lower panel shows photographs of excised renal tumor xenografts. CBT-15X mAB substantially reduced tumor growth.
Figure 34:
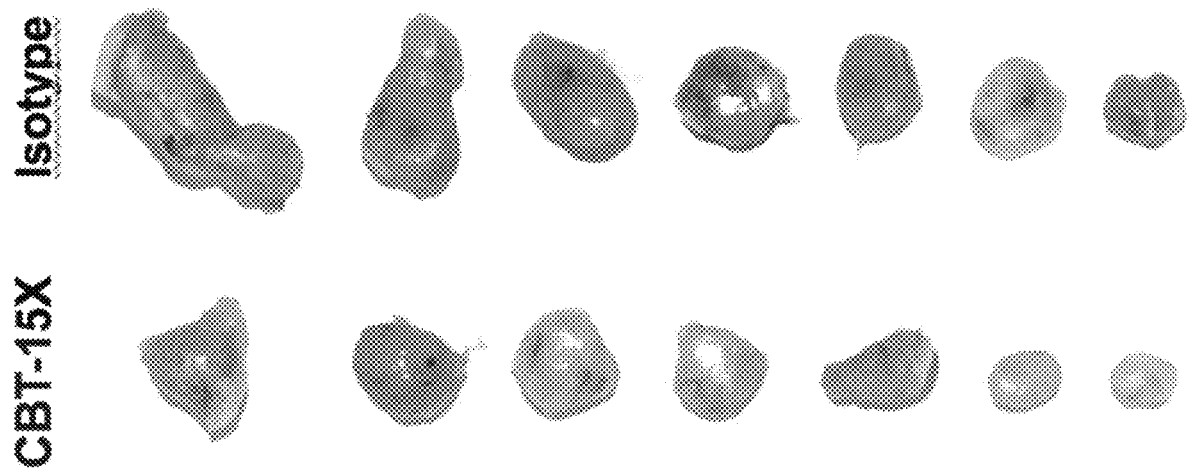
Figure 35:
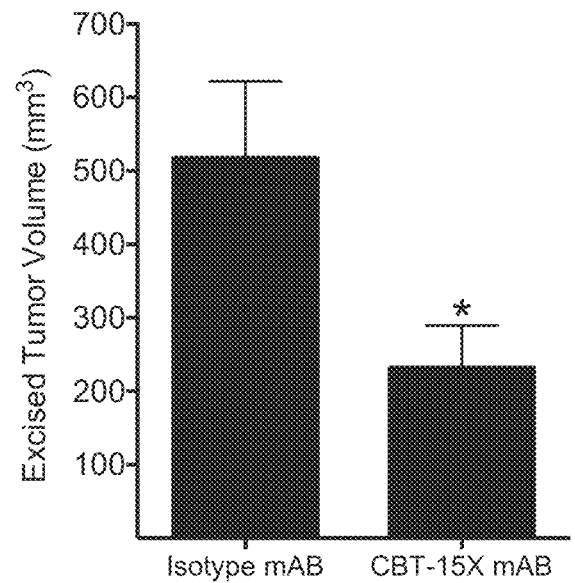
FIG. 35 shows tumor volume of excised tumors of FIG. 34 (p<0.05).
Figure 36:
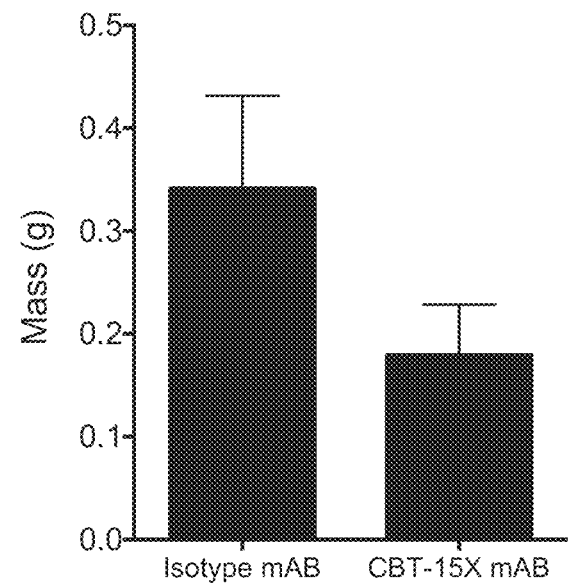
FIG. 36 shows tumor mass of excised tumors of FIG. 34 (p<0.05).

Treatment with CBT-15X mAb strongly inhibited pancreatic cancer AsPC-1 xenograft tumorigenesis resulting in a significant decrease in excised tumor volume and a decrease in tumor weight (FIGS. 34-36).

These findings demonstrate that extracellular DCLK1-targeted monoclonal antibodies are highly effective against cancers, such as renal and pancreatic, which express DCLK1 isoforms 2 and 4.

Renal cancer is highly invasive, results in poor survival, and is tightly associated with cancer stem cell characteristics. Renal cell cancer is characterized by slow-growth, a hypoxic microenvironment, and devastating resistance to drug and radiation therapy. These characteristics are consistent with the presence of tumor stem or stem-like cells. We recently reported that tumor stem cell-specific marker, DCLK1, is epigenetically dysregulated and overexpressed in clear cell renal cell carcinoma (RCC) and that its downregulation inhibits migration/invasion, focal adhesion, and stemness in this disease. The present disclosure expands on these findings and demonstrates that DCLK1 mediates functional stemness leading to resistance to FDA-approved drugs, is linked to the ALDH RCC tumor stem cell marker, and that its extracellular expression marks cells with enhanced clonogenic capacity in RCC. Moreover, we show that DCLK1 mediates expression of immune checkpoint markers CTLA4 and PD-L1, and that treatment with novel DCLK1-targeted monoclonal antibodies (CBT-15A and CBT-15G) can sensitize RCC cells to immune-cell mediated apoptosis. Finally, CBT-15 mABs strongly suppress tumorigenesis in RCC xenografts, providing the first in vivo evidence for targeting DCLK1 in RCC.

It will be understood from the foregoing description that various modifications and changes may be made in the various embodiments of the present disclosure without departing from their true spirit. The description provided herein is intended for purposes of illustration only and is not intended to be construed in a limiting sense, except where specifically indicated. Thus, while the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the present disclosure, it being understood that the particulars shown are by way of example and for purposes of illustrative discussion of particular embodiments only and are presented in the cause of providing what is believed to be a useful and readily understood description of procedures as well as of the principles and conceptual aspects of the inventive concepts. Changes may be made in the formulation of the various components and compositions described herein, the methods described herein or in the steps or the sequence of steps of the methods described herein without departing from the spirit and scope of the present disclosure. All patents, published patent applications, and non-patent publications referenced in any portion of this application are herein expressly incorporated by reference in their entirety to the same extent as if each individual patent or publication was specifically and individually indicated to be incorporated by reference.

What is claimed is:

1. An antibody or an antigen-binding portion thereof, comprising:
   a heavy chain variable region comprising three complementarity determining regions, VH CDR1, VH CDR2, and VH CDR3, selected from the group consisting of (1) the amino acid sequences set forth in SEQ ID NOS: 17, 18, and 19, respectively, and (2) the amino acid sequences set forth in SEQ ID NOS: 27, 28, and 29, respectively; and
   a light chain variable region comprising three complementarity determining regions, VL CDR1, VL CDR2 and VL CDR3, selected from the group consisting of (1) the amino acid sequences set forth in SEQ ID NOS: 20, 21, and 22, respectively, and (2) the amino acid sequences set forth in SEQ ID NOS: 30, 31, and 32, respectively; and
   wherein the antibody or antigen-binding portion thereof specifically binds to Doublecortin-like kinase 1 (DCLK1) isoform 2 or 4.

2. The antibody or antigen-binding portion thereof of claim 1, wherein a dissociation constant ($K_D$) of the antibody or antigen-binding portion thereof is less than about $10^{-9}$ M.

3. The antibody or antigen-binding portion thereof of claim 1, wherein the antibody or antigen-binding portion thereof is murine, chimeric, or humanized.

4. The antibody or antigen-binding portion thereof of claim 1, wherein the heavy chain variable region comprises an amino acid sequence selected from the group consisting of SEQ ID NO:14 and SEQ ID NO:24, and the light chain variable region comprises an amino acid sequence selected from the group consisting of SEQ ID NO:16 and SEQ ID NO:26.

5. The antibody or antigen-binding portion thereof of claim 1, wherein the heavy chain variable region comprises an amino acid sequence having at least about 90% identity to an amino acid sequence selected from the group consisting of SEQ ID NO:14 and SEQ ID NO:24, and the light chain variable region comprises an amino acid sequence having at least about 90% identity to an amino acid sequence selected from the group consisting of SEQ ID NO:16 and SEQ ID NO:26.

6. The antibody or antigen-binding portion thereof of claim 1, wherein the antigen-binding portion thereof is selected from the group comprising scFv, di-scFv, Fab, Fab', F(ab')$_2$, F(ab)$_2$, disulfide linked Fv, diabody, and minibody fragments.

7. The antibody or antigen-binding portion thereof of claim 1, wherein the antibody or antigen-binding portion thereof comprises at least one constant domain selected from the group comprising an IgG constant domain and an IgA constant domain.

8. The antibody or antigen-binding portion thereof of claim 1, wherein the antibody or antigen-binding portion thereof specifically binds to an epitope of DCLK1 comprising the amino acid sequence set forth in SEQ ID NO:10.

9. The antibody or antigen-binding portion thereof of claim 1, wherein:
the antibody or antigen-binding portion thereof is conjugated to a therapeutic agent or diagnostic agent, and optionally wherein the therapeutic agent or diagnostic agent is conjugated to the antibody or antigen-binding portion thereof via an enzyme cleavable linker.

10. The antibody or antigen-binding portion thereof of claim 1, wherein the antibody or antigen-binding portion thereof has inhibitory activity against growth of a neoplastic cell in vivo, and wherein the neoplastic cell is selected from the group comprising tumor stem cells, lung tumor cells, breast tumor cells, pancreatic tumor cells, renal tumor cells, stomach tumor cells, esophageal tumor cells, small intestinal tumor cells, colon tumor cells, and rectal tumor cells.

11. A composition, comprising:
the antibody or antigen-binding portion thereof of claim 1; and
at least one pharmaceutically-acceptable carrier.

12. A method of treating a DCLK1-associated disease or condition in a subject in need of such therapy, the method comprising the step of:
administering to a subject an effective amount of the antibody or antigen-binding portion thereof of claim 1.

13. The method of claim 12, wherein the DCLK1-associated disease or condition is selected from the group comprising tumor stem cell metastasis, lung cancer, breast cancer, pancreatic cancer, renal cancer, esophageal cancer, stomach cancer, small intestinal cancer, colon cancer, and rectal cancer.

14. An isolated polynucleotide encoding the antibody or antigen-binding portion thereof of claim 1.

15. An expression vector comprising the isolated polynucleotide of claim 14.

16. A host cell comprising the expression vector of claim 15.

17. The method of claim 12, wherein the heavy chain variable region of the antibody or antigen-binding portion thereof comprises an amino acid sequence having at least about 90% identity to SEQ ID NO:14 or SEQ ID NO:24, and the light chain variable region of the antibody or antigen-binding portion comprises an amino acid sequence having at least about 90% identity to SEQ ID NO:16 or SEQ ID NO:26.

18. The method of claim 12, wherein the antibody or antigen-binding portion thereof is selected from the group comprising scFv, di-scFv, Fab, Fab', F(ab')$_2$, F(ab)$_2$, disulfide linked Fv, diabody, and minibody fragments.

19. The method of claim 12, wherein the antibody or antigen-binding portion thereof comprises at least one constant domain selected from the group comprising an IgG constant domain and an IgA constant domain.

20. The method of claim 12, wherein the antibody or antigen-binding portion thereof specifically binds to an epitope of DCLK1 comprising the amino acid sequence set forth in SEQ ID NO:10.

21. An antibody or an antigen-binding portion thereof, comprising:
a heavy chain variable region comprising three complementarity determining regions, VH CDR1, VH CDR2, and VH CDR3, selected from the group consisting of the amino acid sequences set forth in SEQ ID NOS: 17, 18, and 19, respectively; and
a light chain variable region comprising three complementarity determining regions, VL CDR1, VL CDR2 and VL CDR3, selected from the group consisting of the amino acid sequences set forth in SEQ ID NOS: 20, 21, and 22, respectively; and
wherein the antibody or antigen-binding portion thereof specifically binds to Doublecortin-like kinase 1 (DCLK1) isoform 2 or 4.

22. An antibody or an antigen-binding portion thereof, comprising:
a heavy chain variable region comprising three complementarity determining regions, VH CDR1, VH CDR2, and VH CDR3, selected from the group consisting of the amino acid sequences set forth in SEQ ID NOS: 27, 28, and 29, respectively; and
a light chain variable region comprising three complementarity determining regions, VL CDR1, VL CDR2 and VL CDR3, selected from the group consisting of the amino acid sequences set forth in SEQ ID NOS: 30, 31, and 32, respectively; and
wherein the antibody or antigen-binding portion thereof specifically binds to Doublecortin-like kinase 1 (DCLK1) isoform 2 or 4.

* * * * *

UNITED STATES PATENT AND TRADEMARK OFFICE
CERTIFICATE OF CORRECTION

PATENT NO. : 11,655,307 B2
APPLICATION NO. : 16/617074
DATED : May 23, 2023
INVENTOR(S) : Courtney W. Houchen et al.

It is certified that error appears in the above-identified patent and that said Letters Patent is hereby corrected as shown below:

In the Specification
Column 1, Line 59: Delete "sternness" and replace with -- stemness --
Column 25, Line 56: Delete "Anon" and replace with -- A non --
Column 37, Line 12: Delete "Scat" and replace with -- Scal --
Column 39, Line 64: Delete "G213" and replace with -- G2β --
Column 43, Lines 62-63: Delete "Sternness-Supporting" and replace with -- Stemness-Supporting --
Column 44, Line 22: Delete "sternness," and replace with -- stemness, --
Column 45, Line 44: Delete "Sternness" and replace with -- Stemness --
Column 45, Lines 62-63: Delete "sternness," and replace with -- stemness, --
Column 46, Line 6: Delete "sternness" and replace with -- stemness --
Column 46, Line 33: Delete "sternness" and replace with -- stemness --
Column 46, Line 35: Delete "sternness" and replace with -- stemness --

Signed and Sealed this
Twenty-seventh Day of June, 2023

Katherine Kelly Vidal
*Director of the United States Patent and Trademark Office*